United States Patent [19]

Narula et al.

[11] Patent Number: 5,321,007
[45] Date of Patent: Jun. 14, 1994

[54] 2,6-DIMETHYLBICYCLO[3.3.1]NON-6-ENE-3-METHANOL, SUBSTITUTED DERIVATIVES THEREOF, ORGANOLEPTIC UTILITIES THEREOF, PROCESSES FOR PRODUCING SAME, AND PROCESS INTERMEDIATES THEREFOR

[75] Inventors: Anubhav P. S. Narula; Matthew J. McGinnis, both of Hazlet; Leroy P. John, Neshavnic Station, all of N.J.; Franc T. Schiet, New York, N.Y.; Charles E. J. Beck, Summit, N.J.

[73] Assignee: International Flavors & Fragrances Inc., New York, N.Y.

[21] Appl. No.: 141,726

[22] Filed: Oct. 27, 1993

[51] Int. Cl.$^5$ .............................................. A61K 7/46
[52] U.S. Cl. ........................................ 512/12; 512/19; 512/18; 512/3; 252/174.11; 568/820; 568/665; 560/256; 560/260; 549/430
[58] Field of Search ............... 512/3, 18, 19; 568/820, 568/663; 560/256, 200; 549/430; 252/174.11

[56] References Cited

PUBLICATIONS

Chem. Abstr., vol. 103, #196,290g (1985).

Primary Examiner—James H. Reamer
Attorney, Agent, or Firm—Arthur L. Liberman

[57] ABSTRACT

Described are 2,6-dimethylbicyclo[3.3.1]non-6-ene-3-methanol and substituted derivatives thereof defined according to the generic structure:

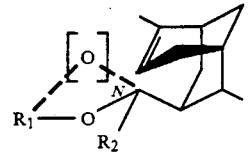

wherein each of the dashed lines represents a carbon-oxygen covalent bond or no bond; N is 0 or 1; $R_1$ represents hydrogen, $C_1$-$C_2$ lower alkyl, lower alkenyl, lower alkylenyl, $C_1$-$C_2$ acyl, alkoxycarbonyl, magnesium halo or lithium; and $R_2$ represents methyl or hydrogen as well as uses thereof (wherein $R_1$ is not magnesium halo or lithium) for augmenting or enhancing the aroma of consumable materials selected from the group consisting of perfume compositions, perfumed articles, colognes, deodorizing articles, deodorizing compositions and malodor maskants.

23 Claims, 51 Drawing Sheets

GLC PROFILE FOR EXAMPLE I.

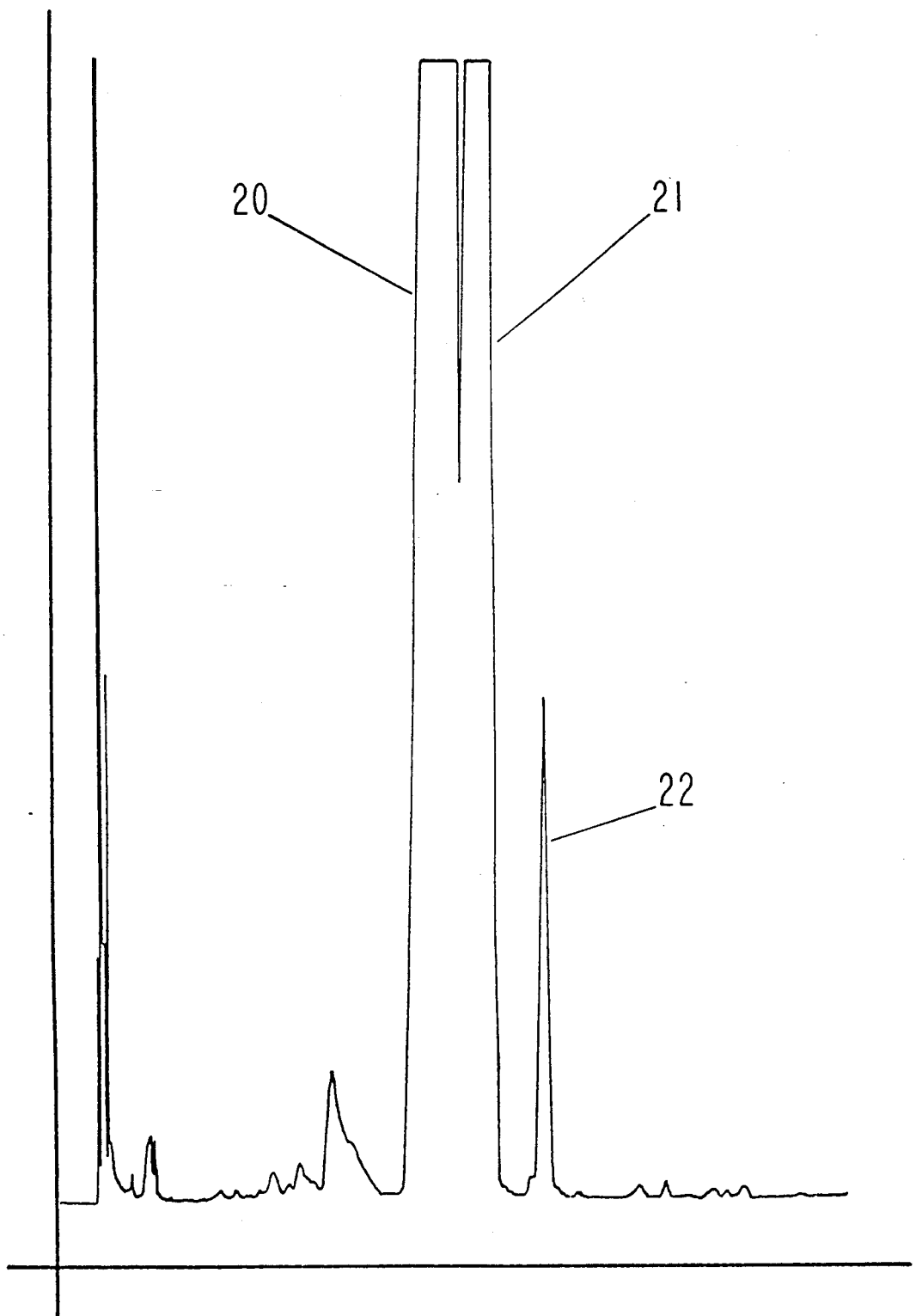

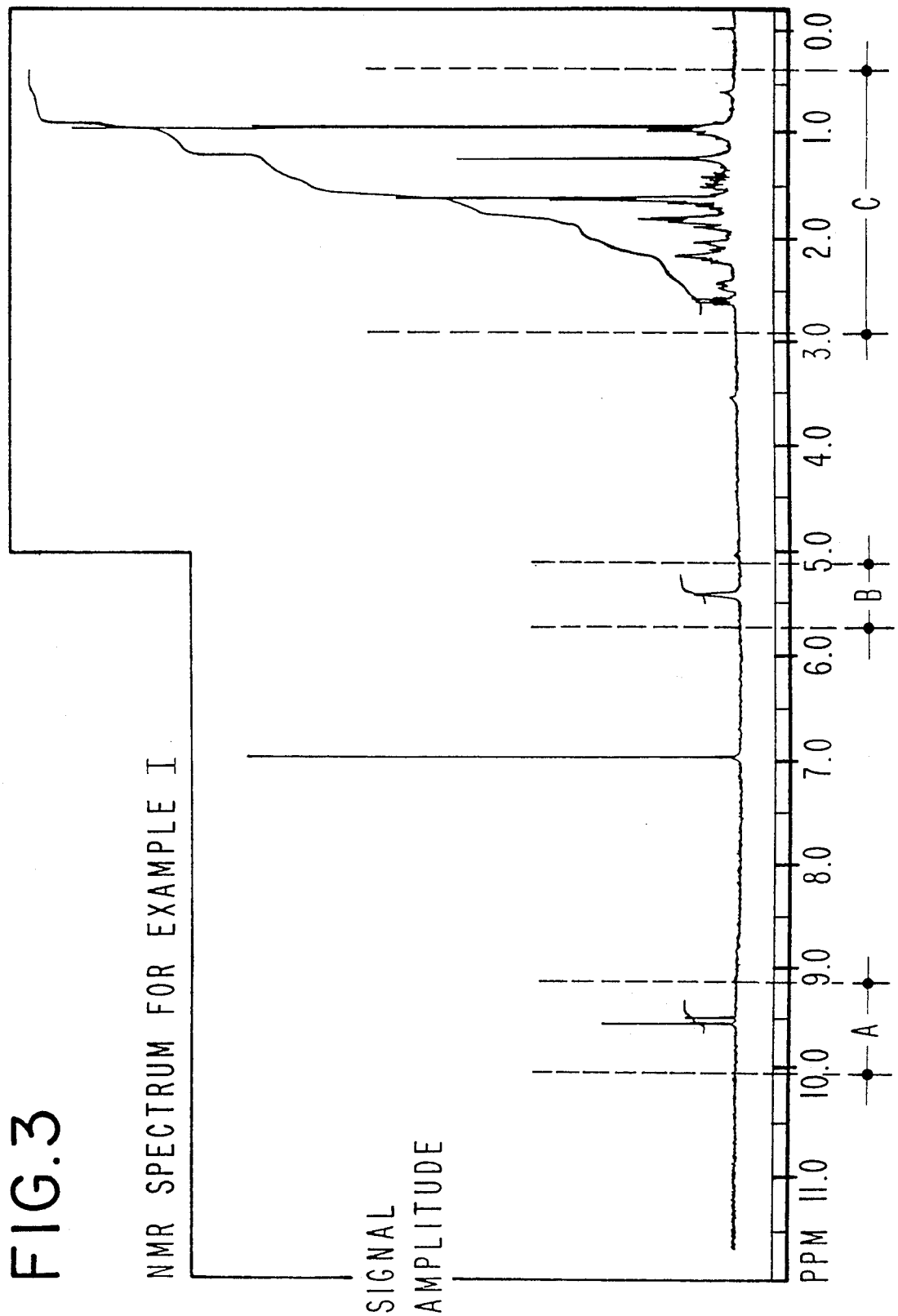
FIG. 3 NMR SPECTRUM FOR EXAMPLE I

FIG. 3-A
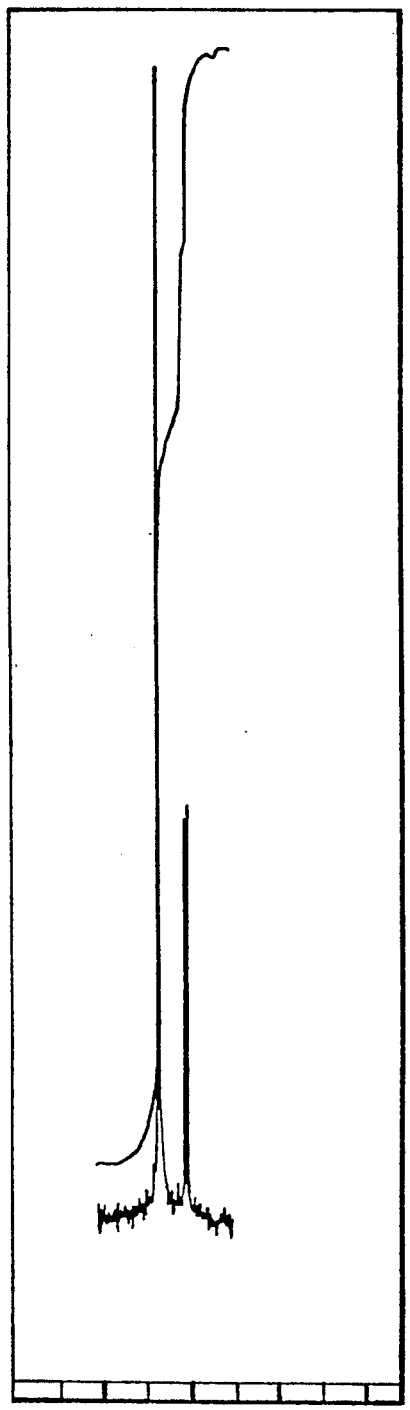
9.6
PPM
FIG. 3-B
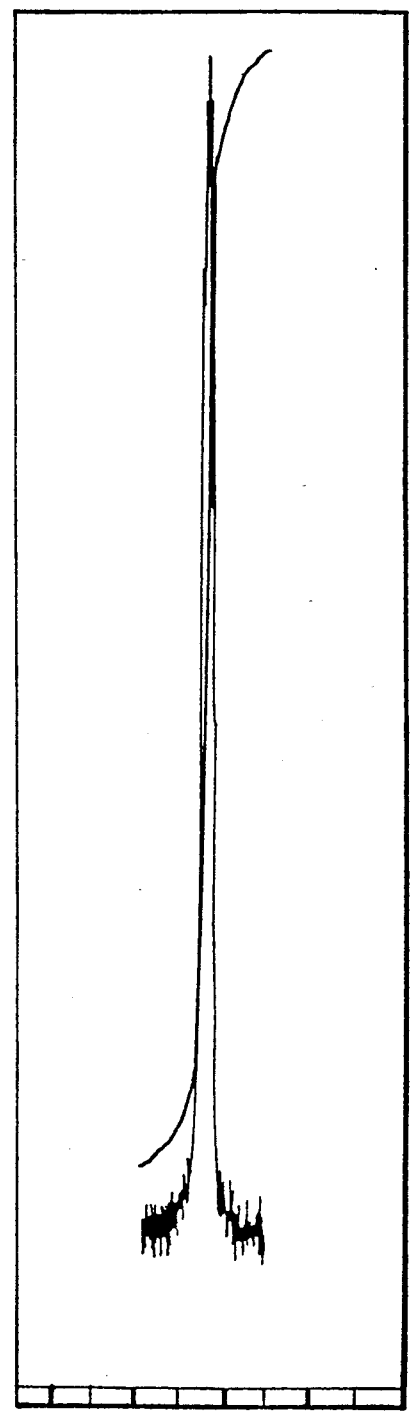
5.4
PPM

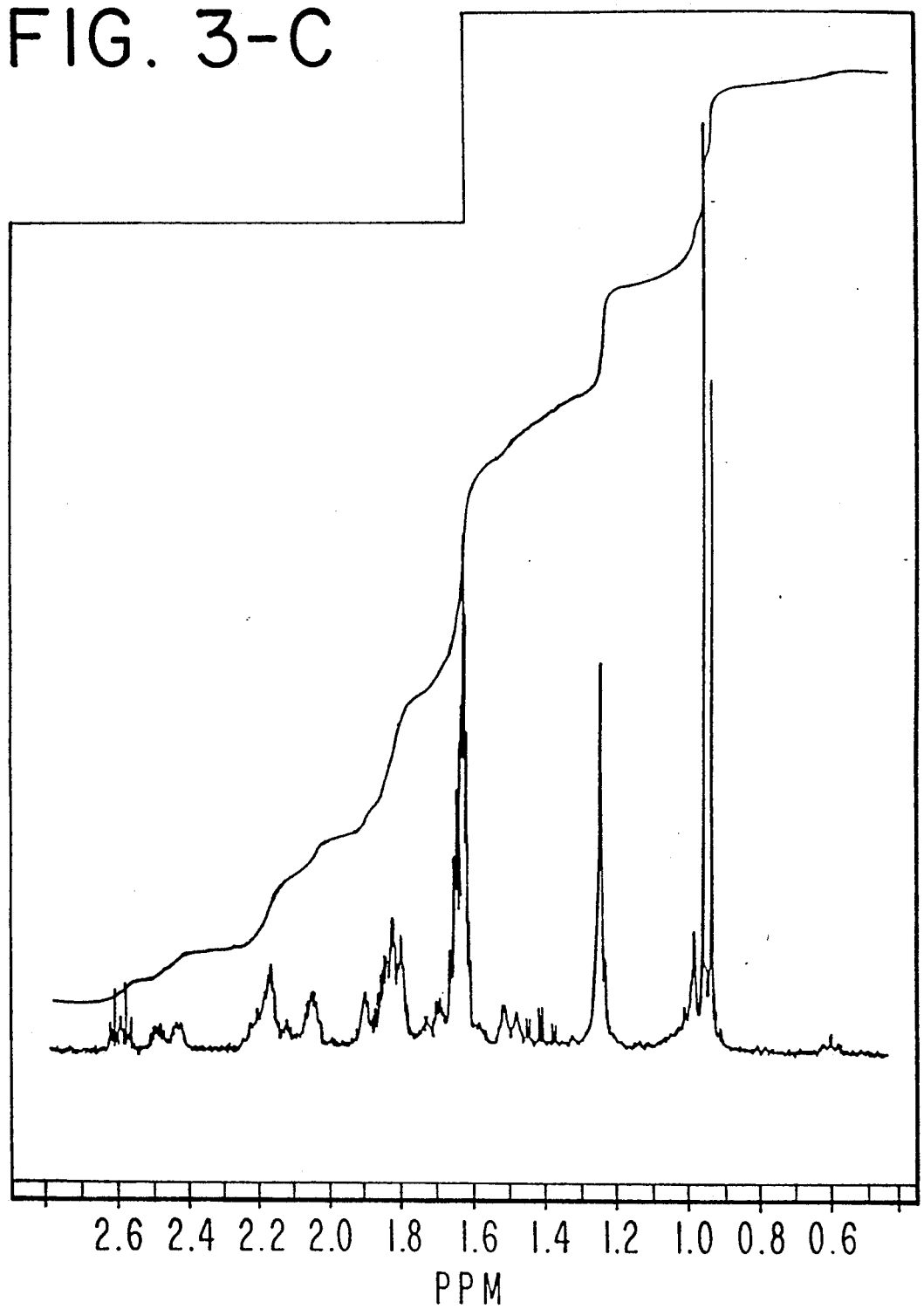
FIG. 3-C

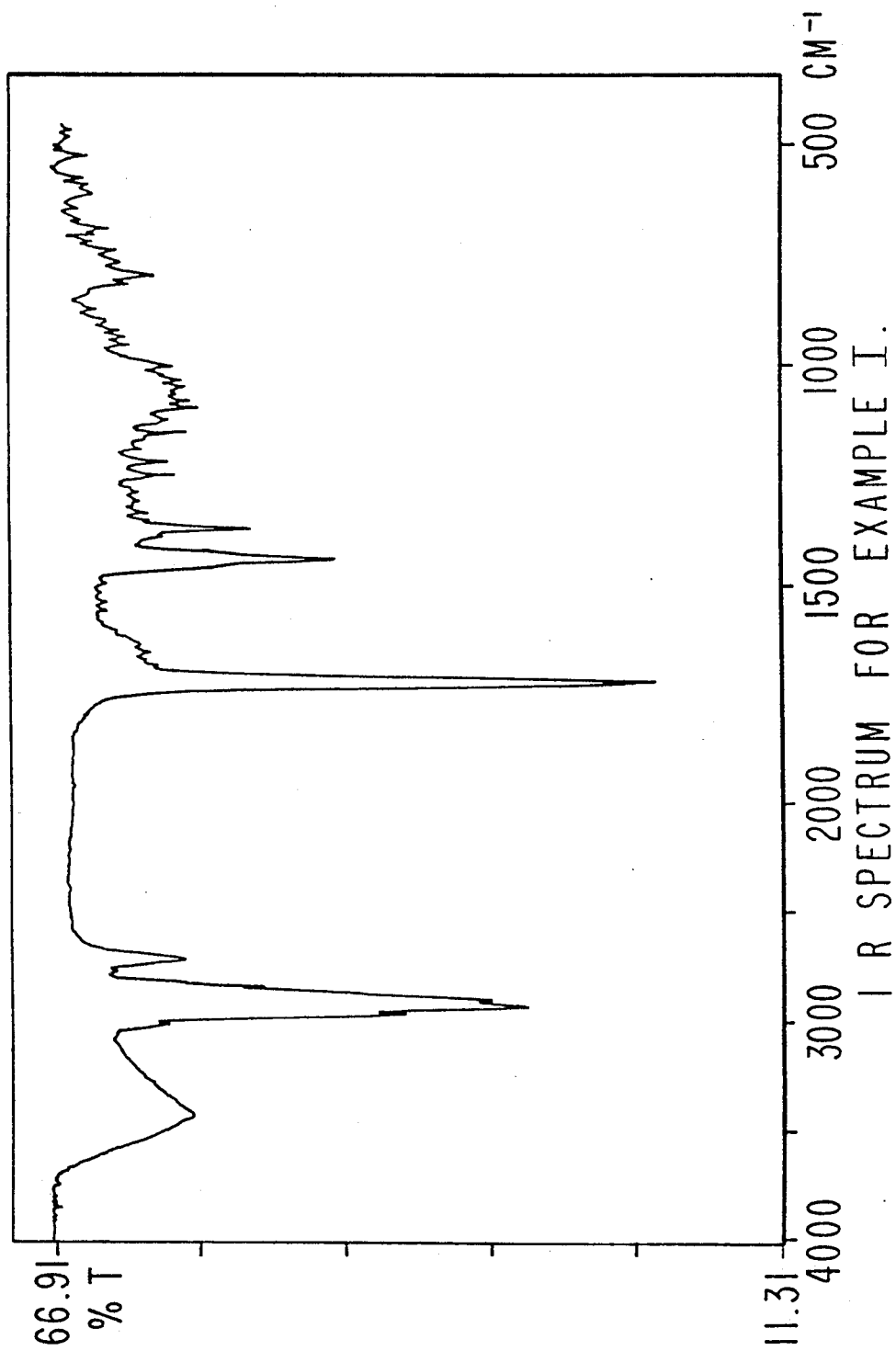

GLC PROFILE FOR EXAMPLE II.

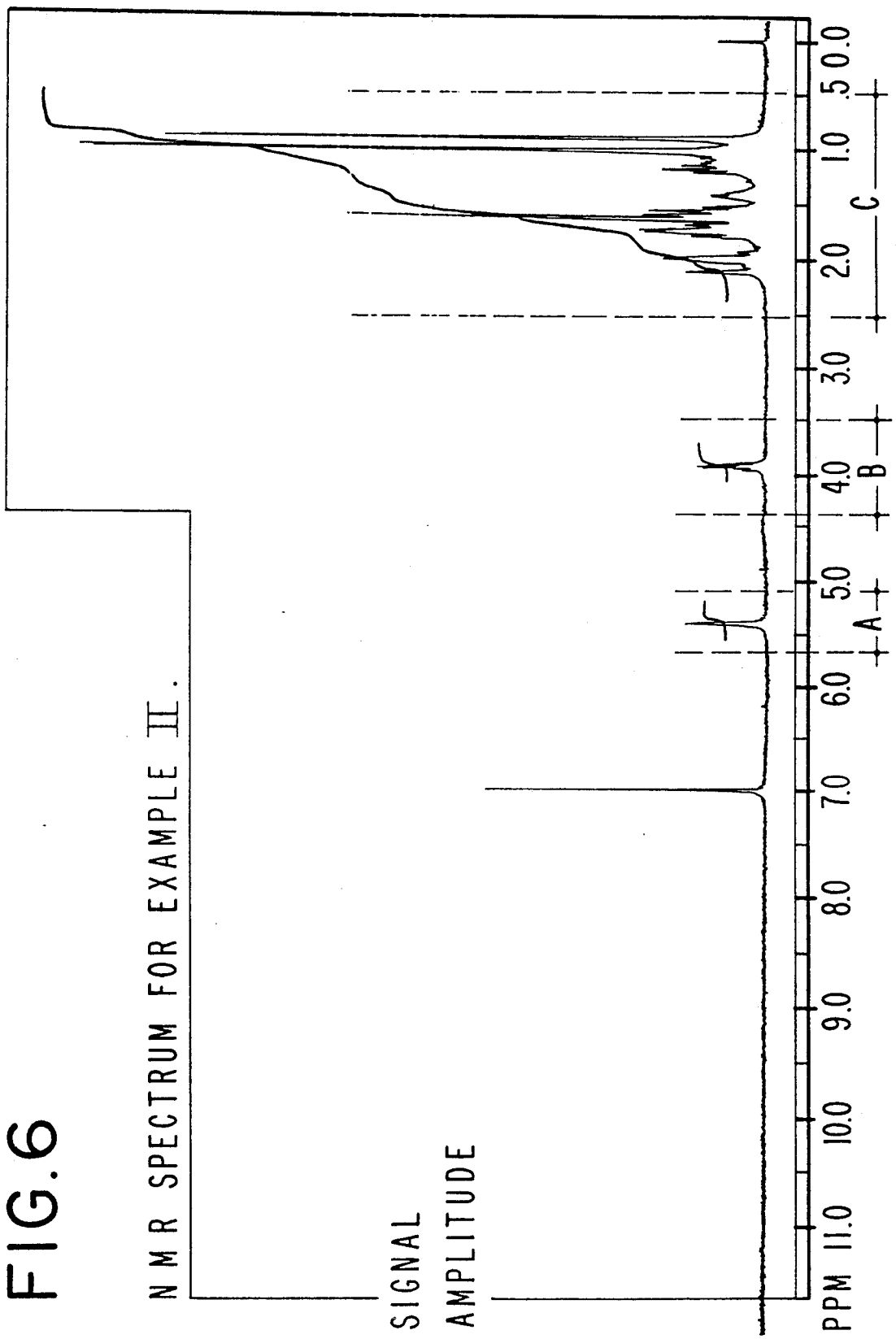
FIG. 6 NMR SPECTRUM FOR EXAMPLE II.

FIG.6-A
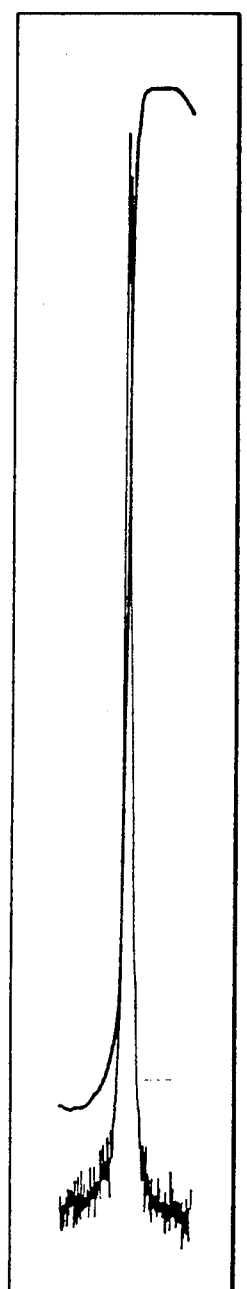
5.4
PPM
FIG.6-B
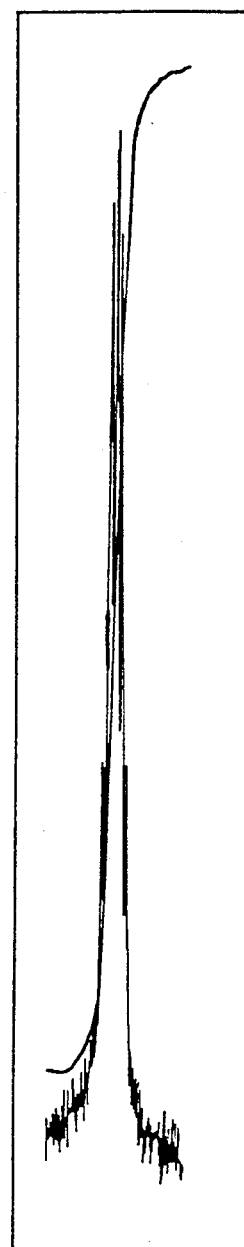
4.0  3.8
PPM

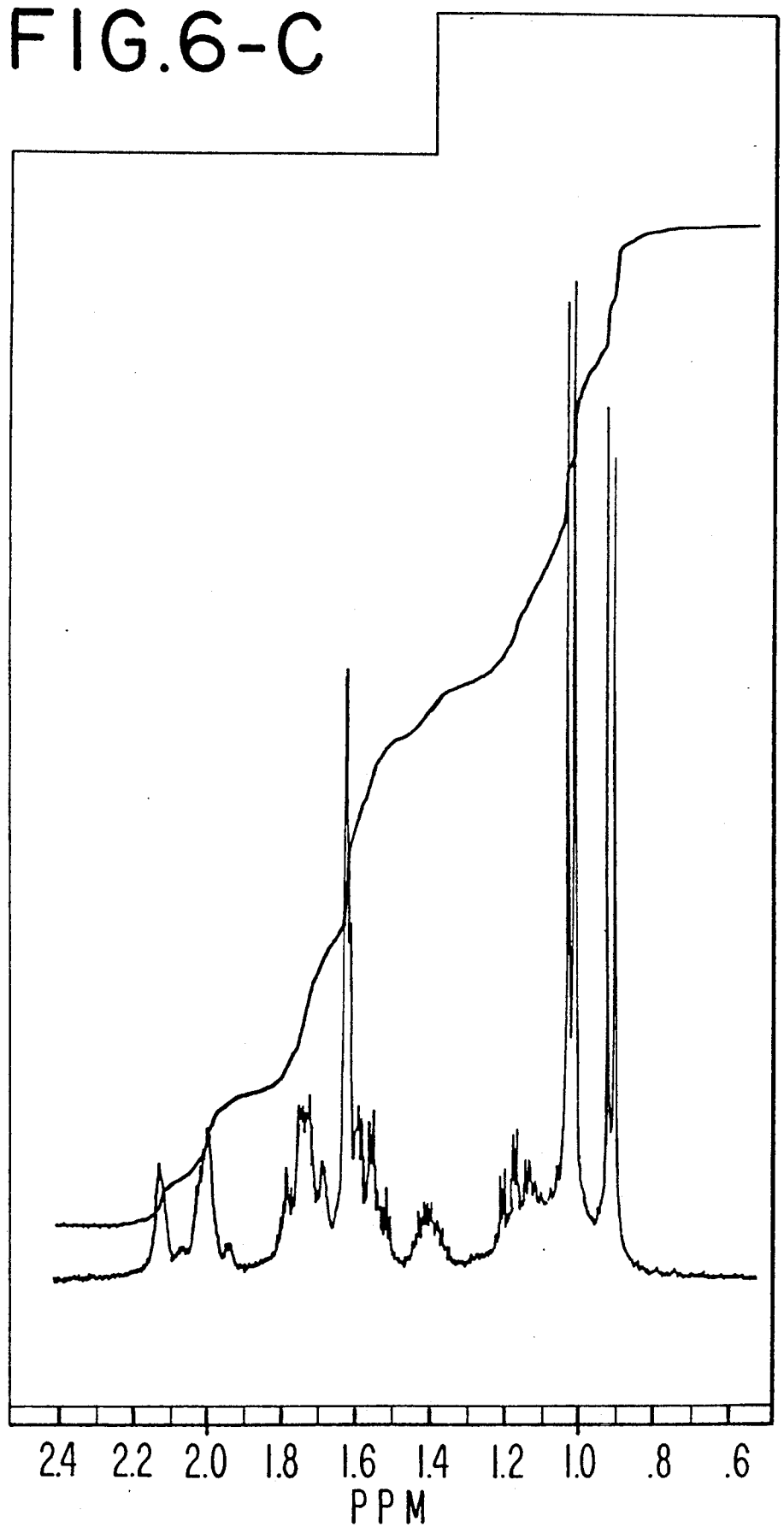
FIG.6-C

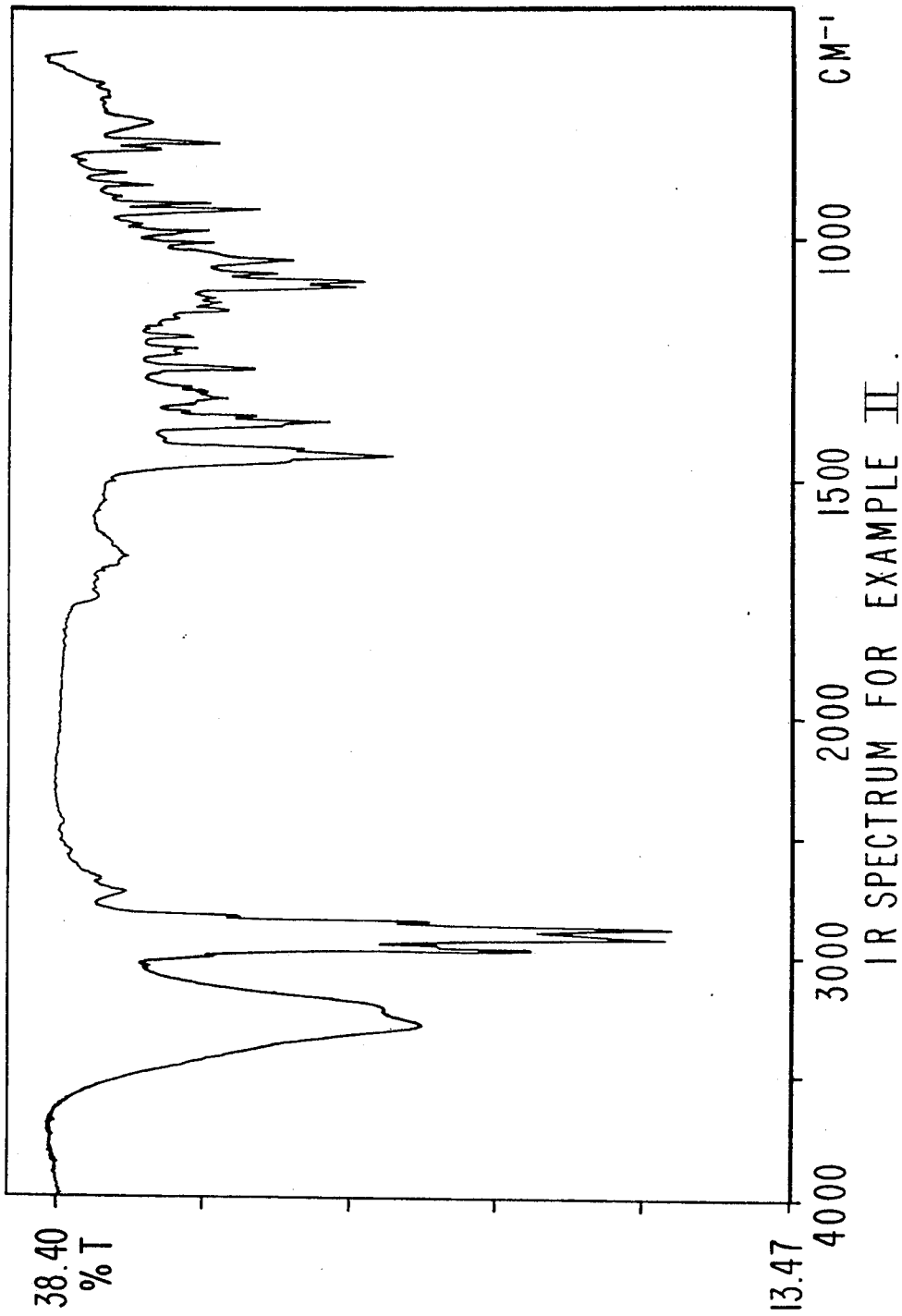

GLC PROFILE FOR EXAMPLE III

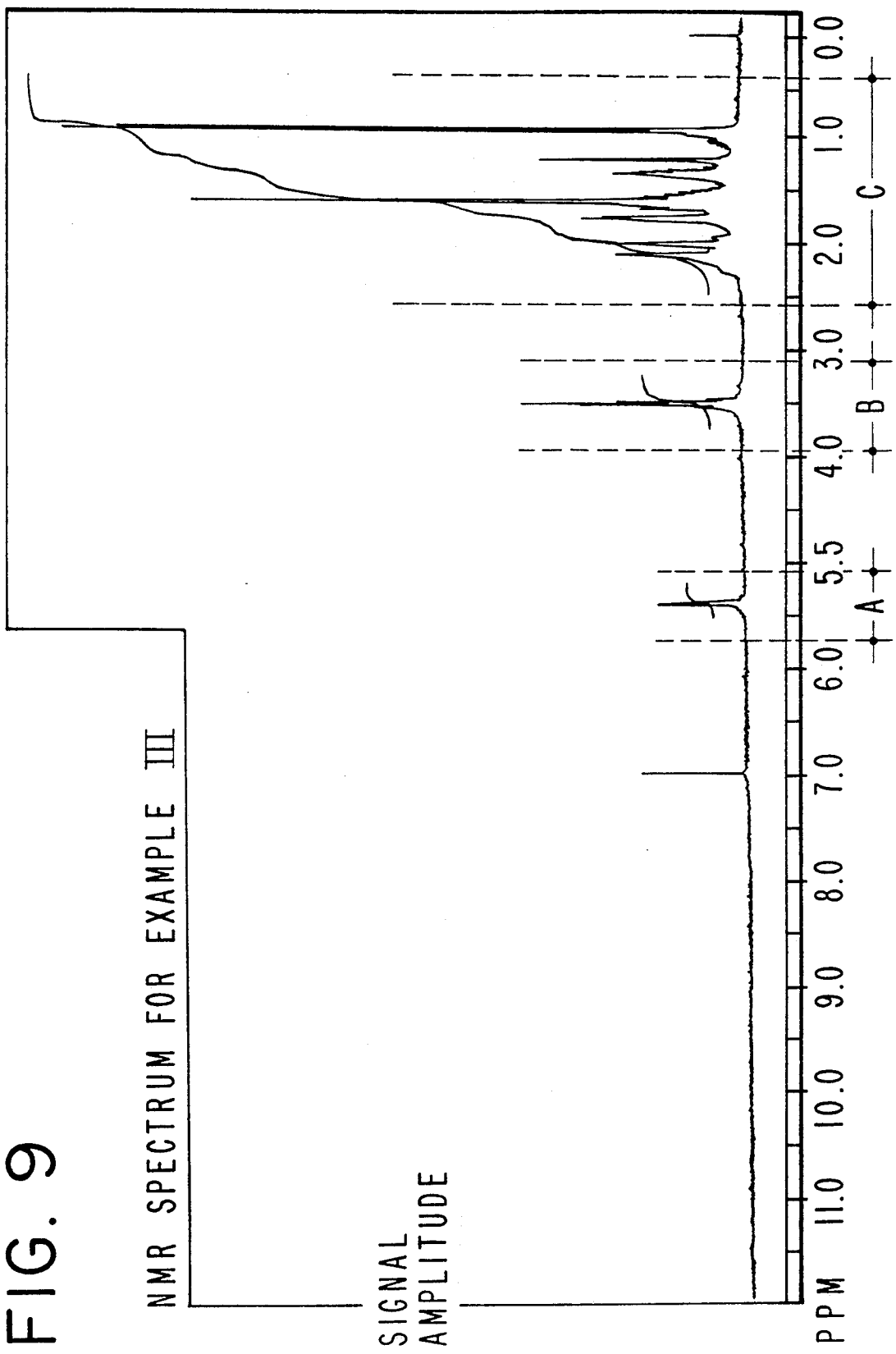
FIG. 9 NMR SPECTRUM FOR EXAMPLE III

FIG. 9-A
FIG. 9-B
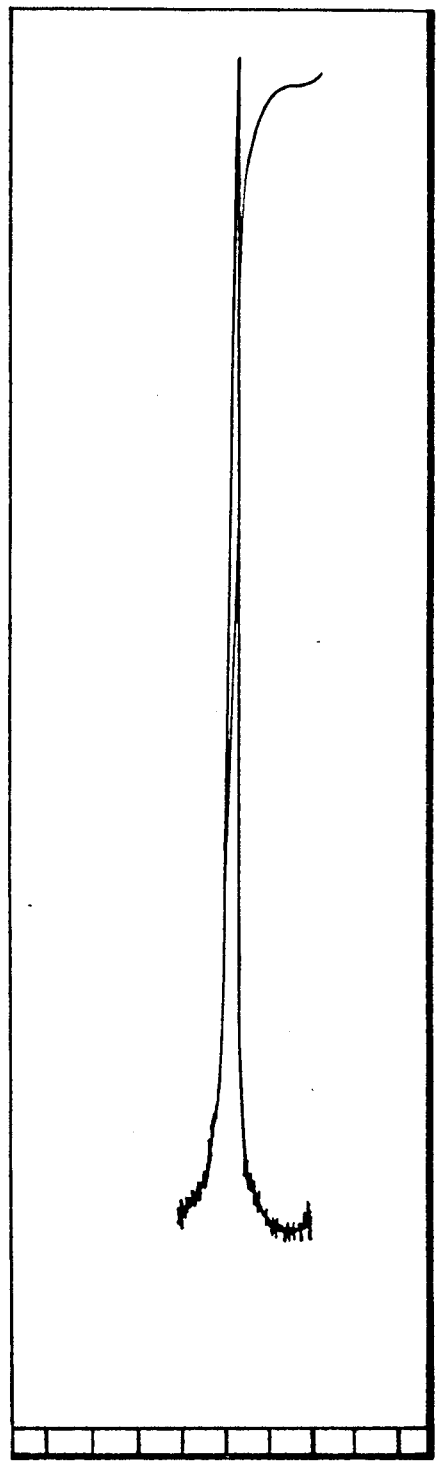
5.4
PPM
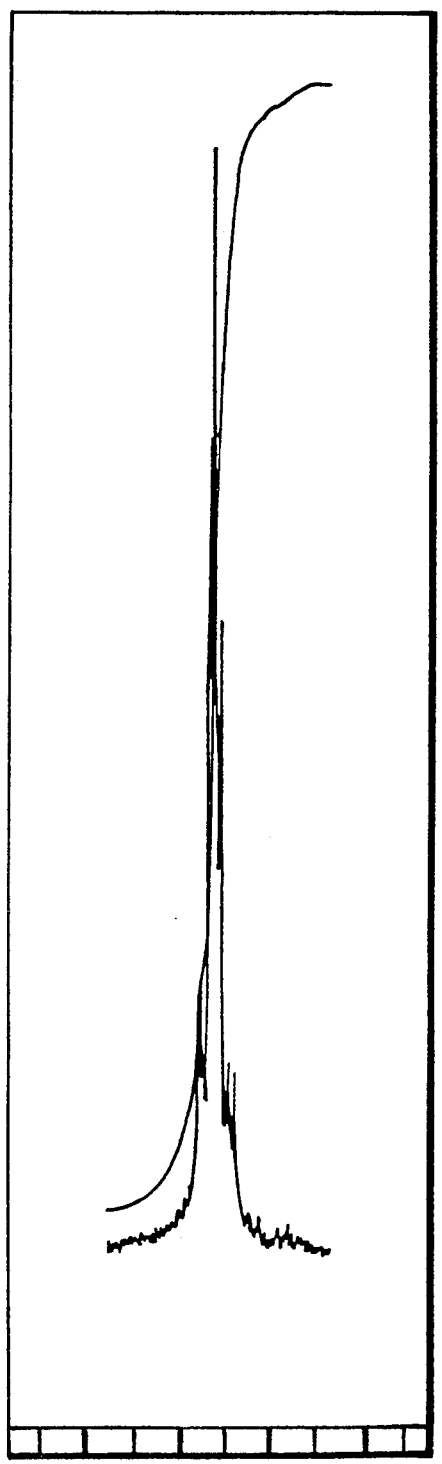
3.6 3.4
PPM

FIG. 9-C
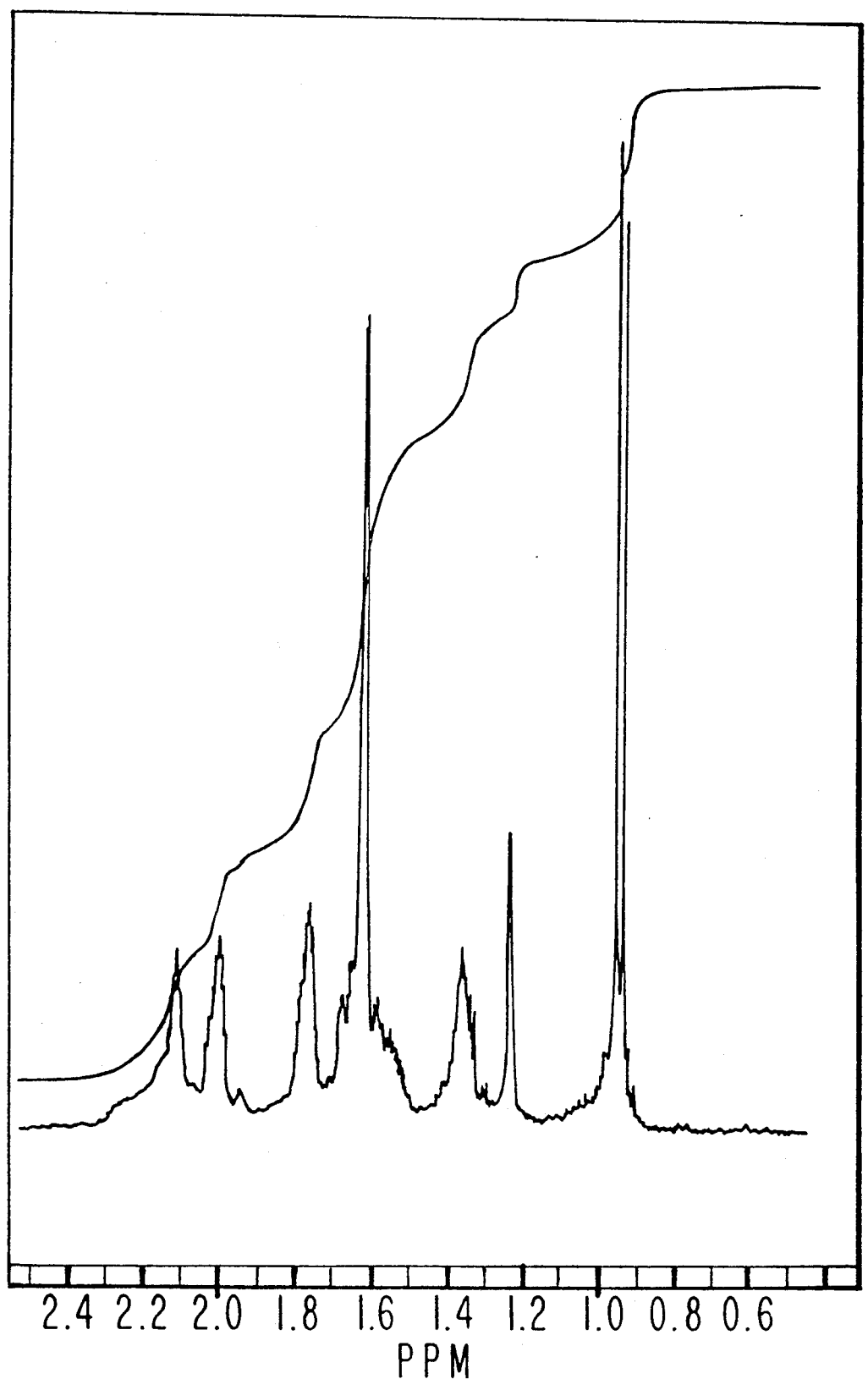

IR SPECTRUM FOR EXAMPLE III

GLC PROFILE FOR EXAMPLE II.

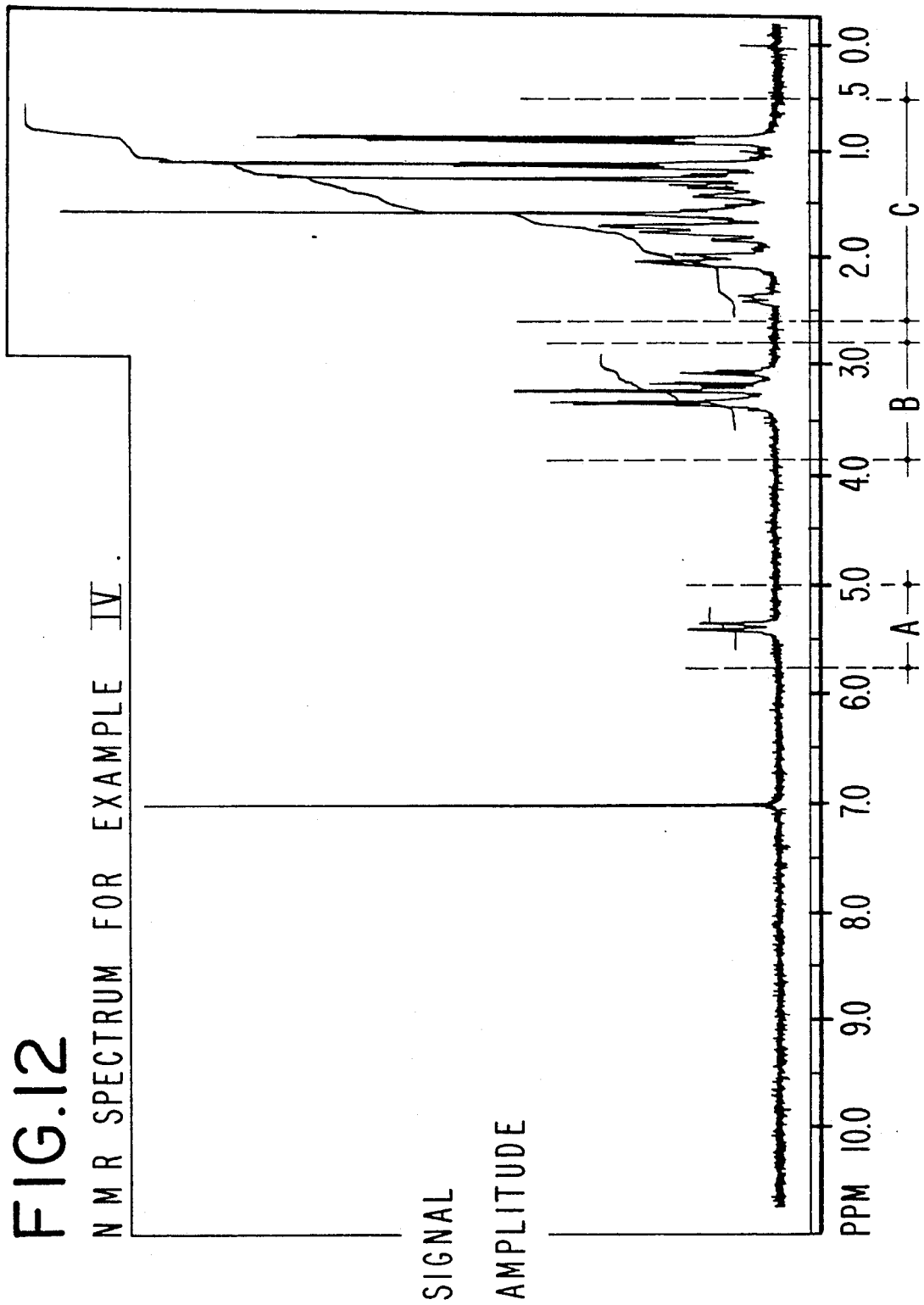
FIG.12 NMR SPECTRUM FOR EXAMPLE IV

FIG.12-A
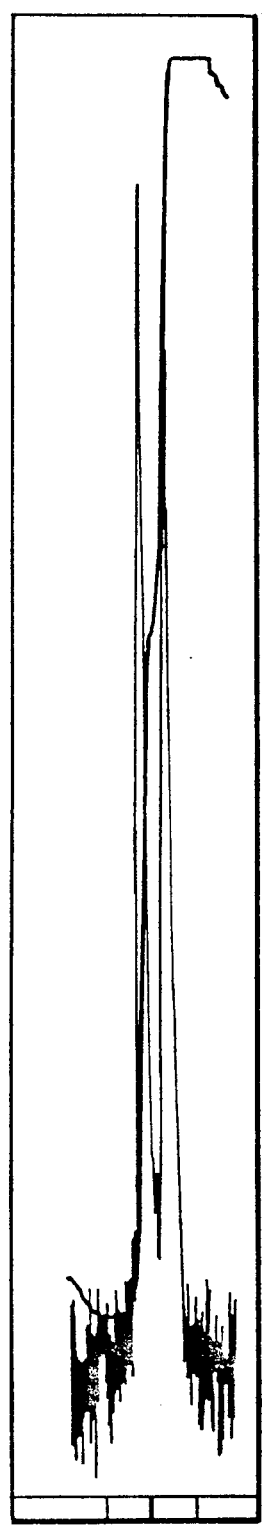
5.4
PPM
FIG.12-B
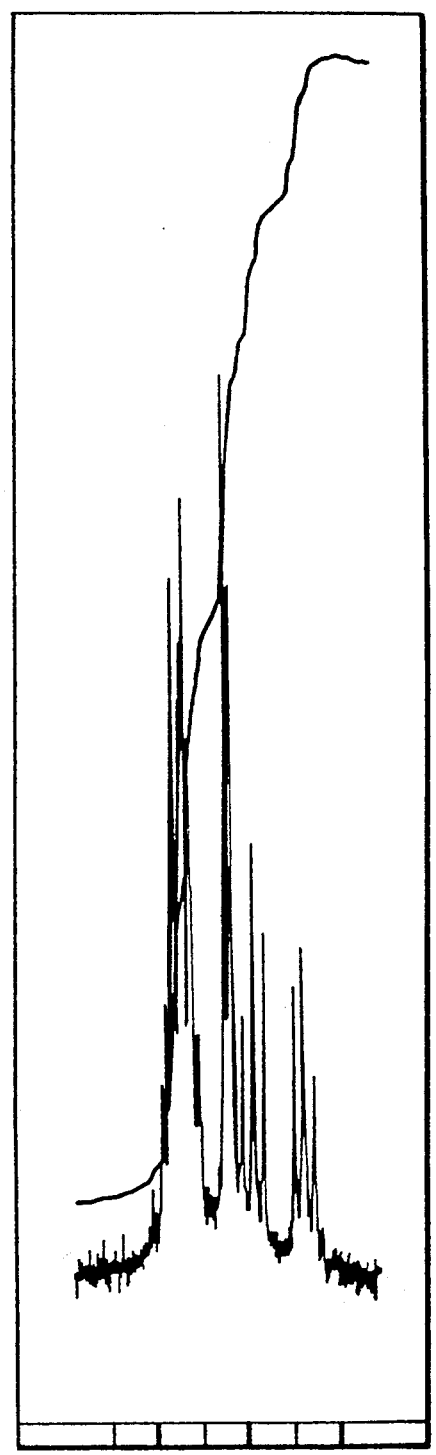
3.4  3.2  3.0
PPM

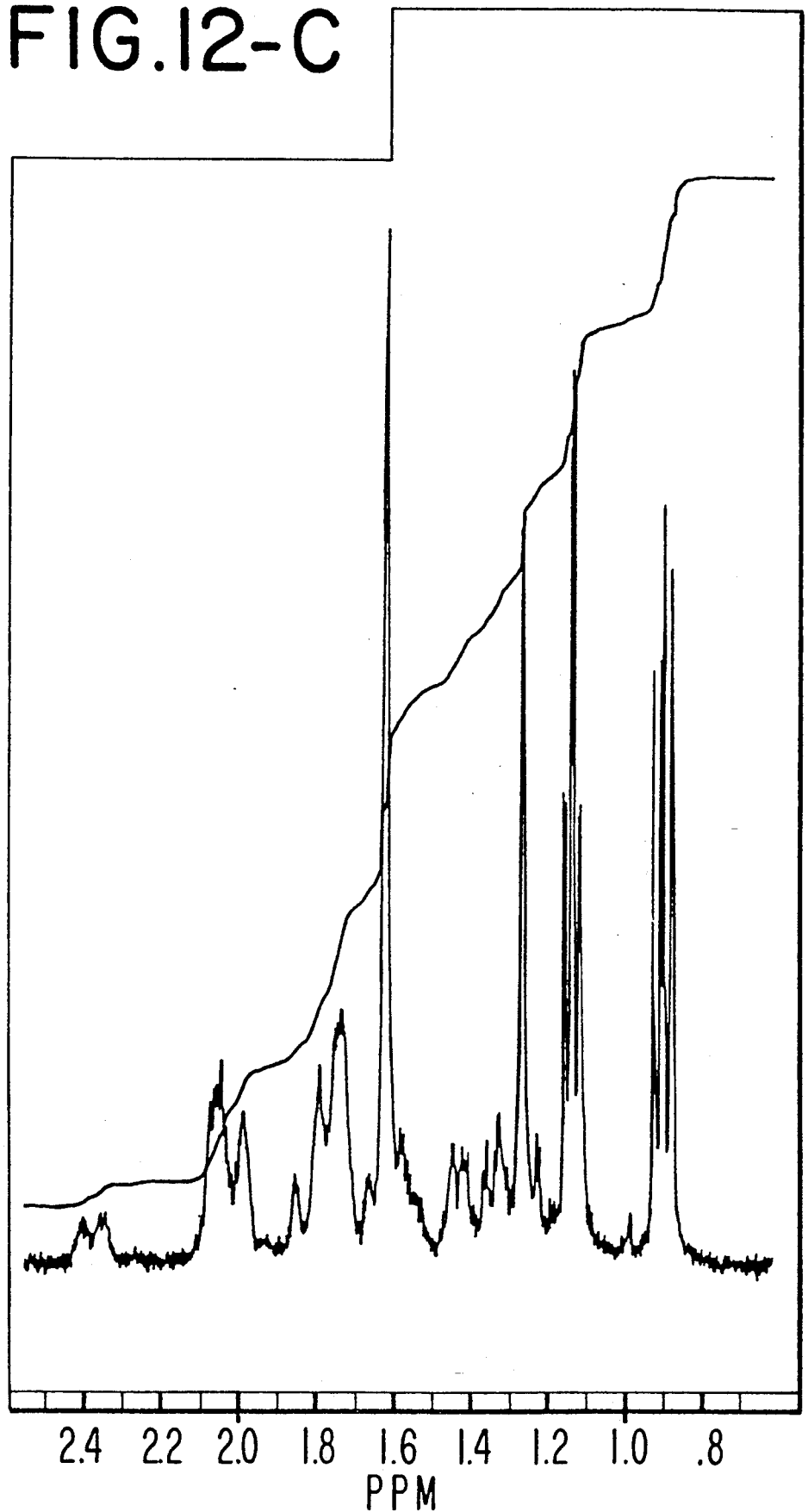
FIG.12-C

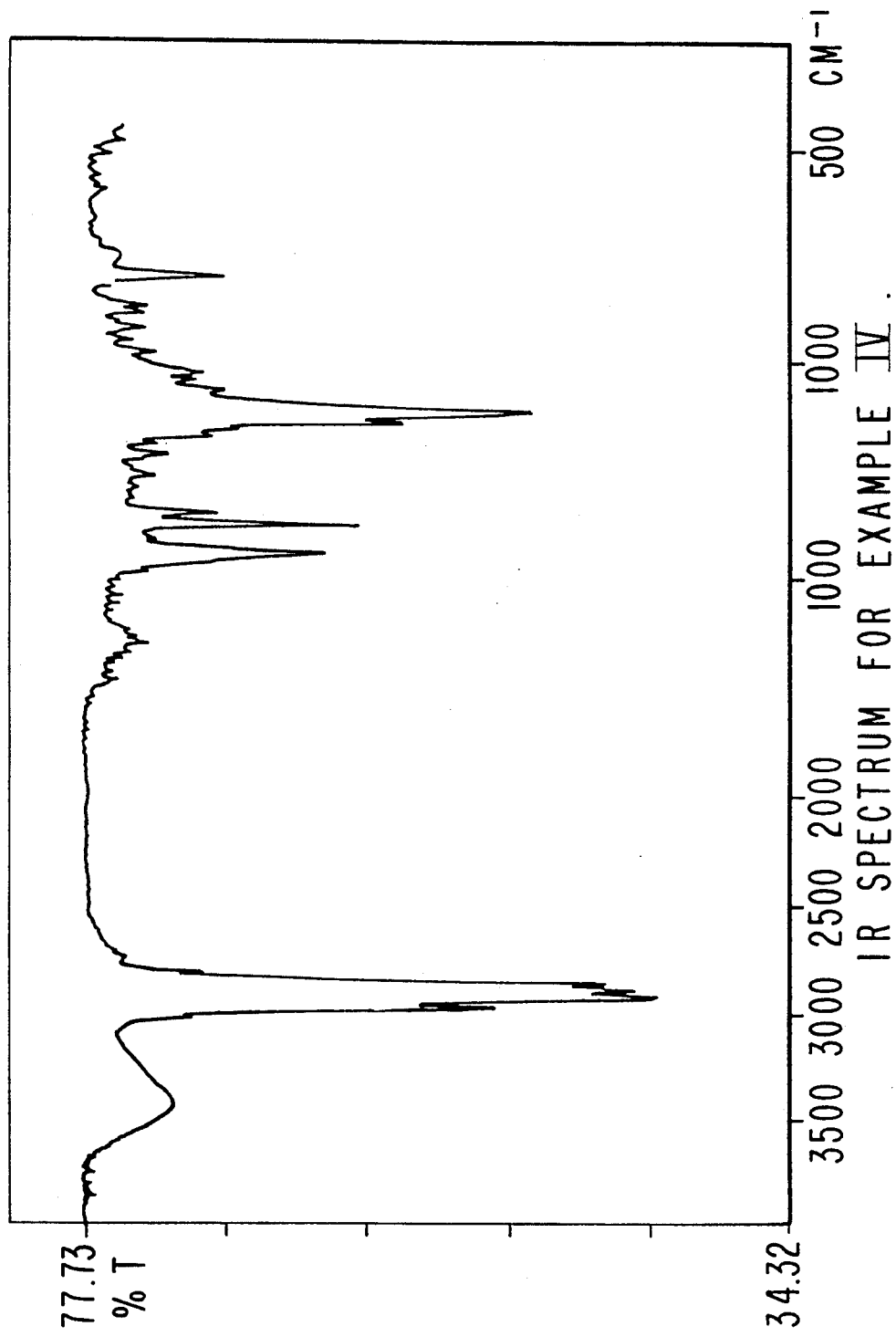
FIG.13 IR SPECTRUM FOR EXAMPLE IV.

GLC PROFILE FOR EXAMPLE V

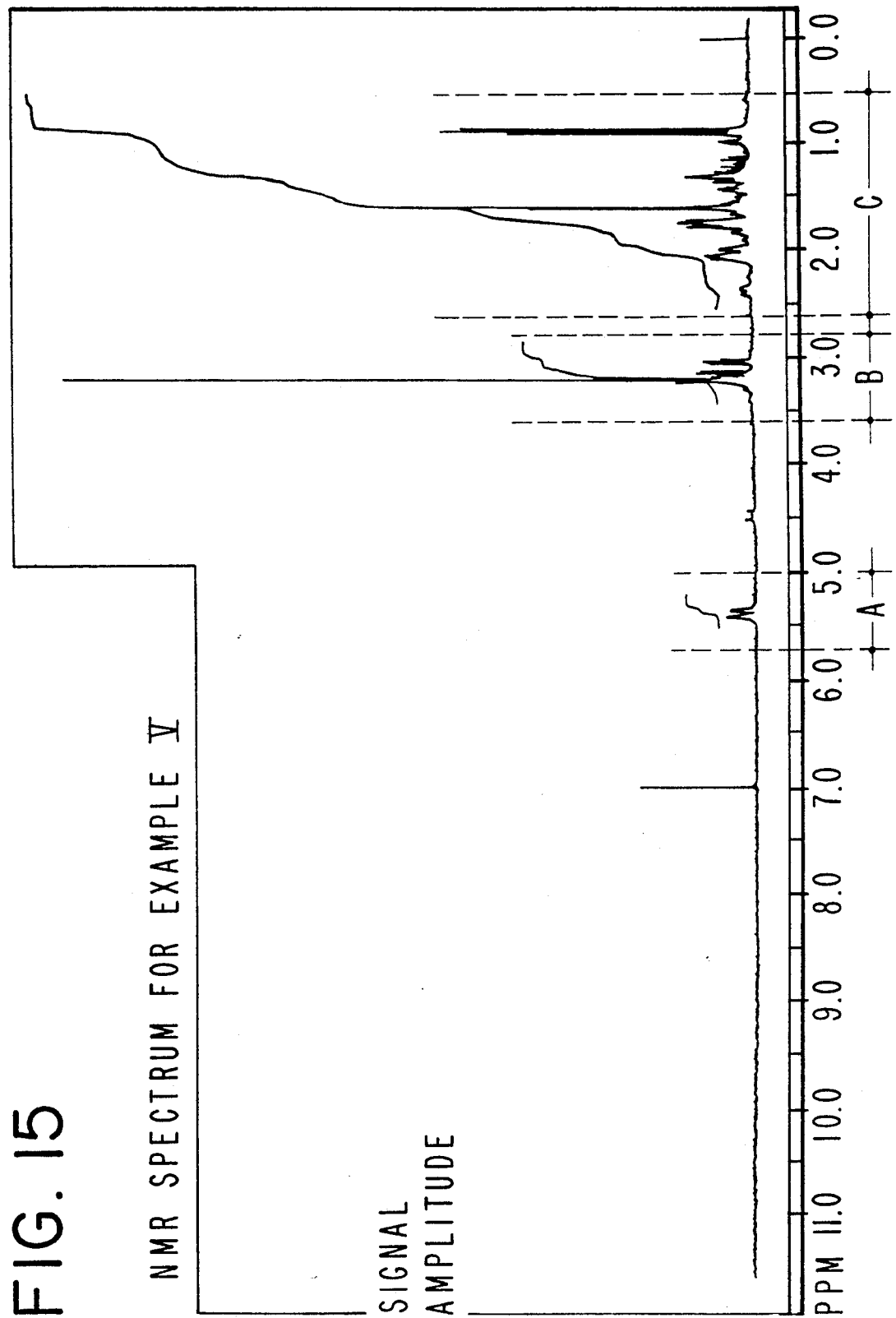
FIG. 15 NMR SPECTRUM FOR EXAMPLE V

FIG. 15-A
FIG. 15-B
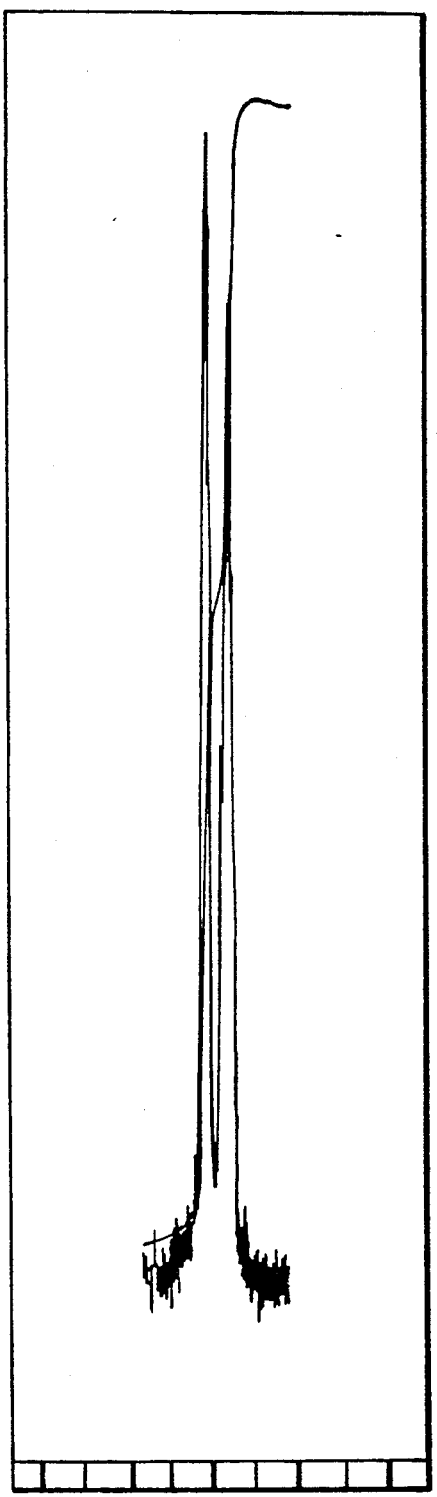
5.4
PPM
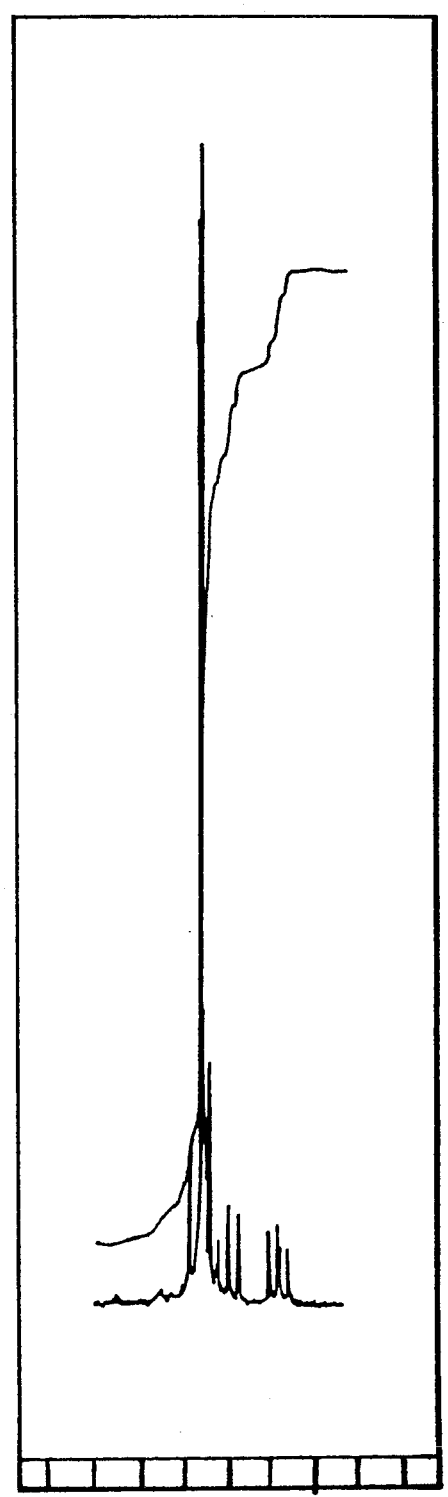
3.4 3.2 3.0
PPM

FIG. 15-C
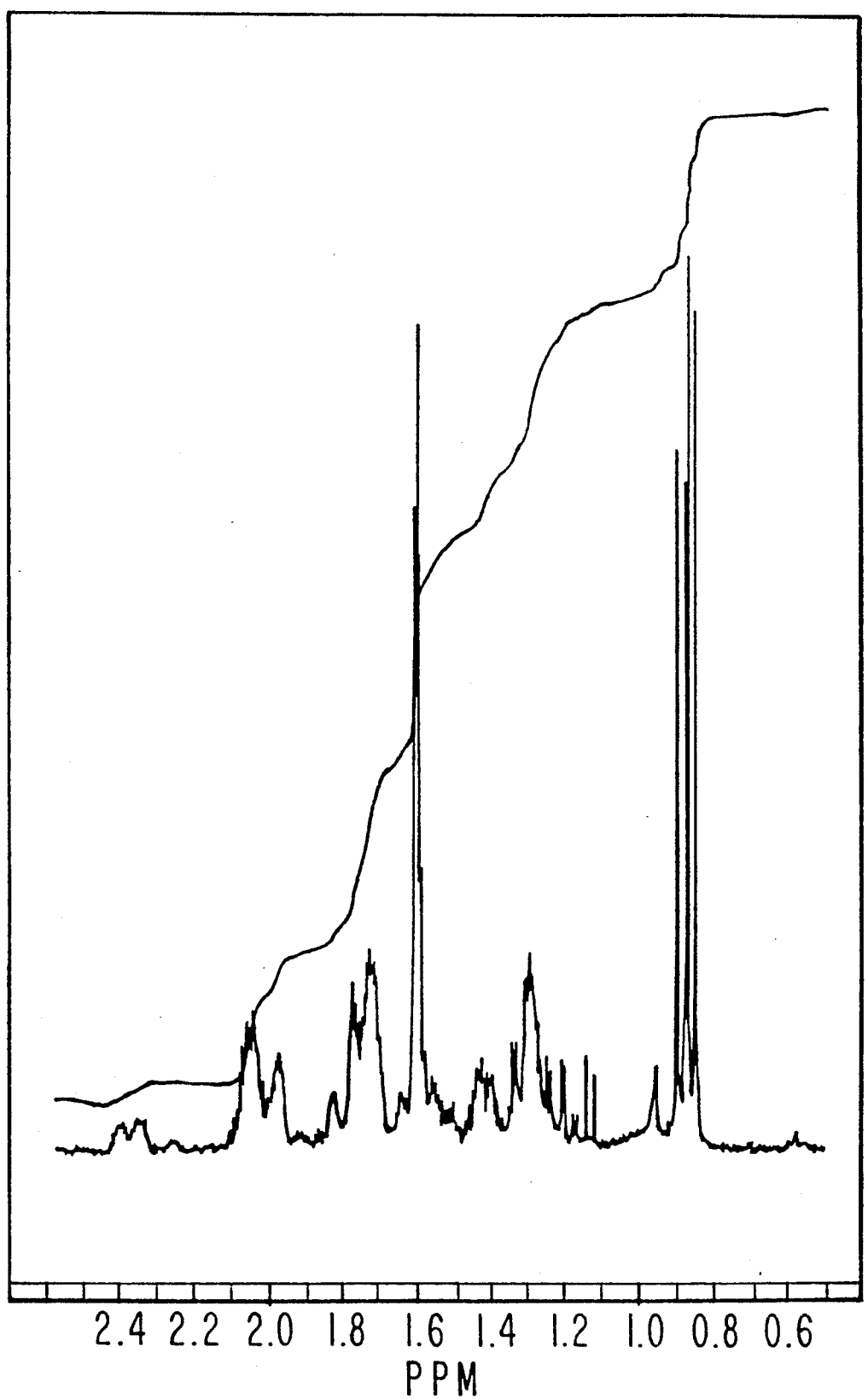

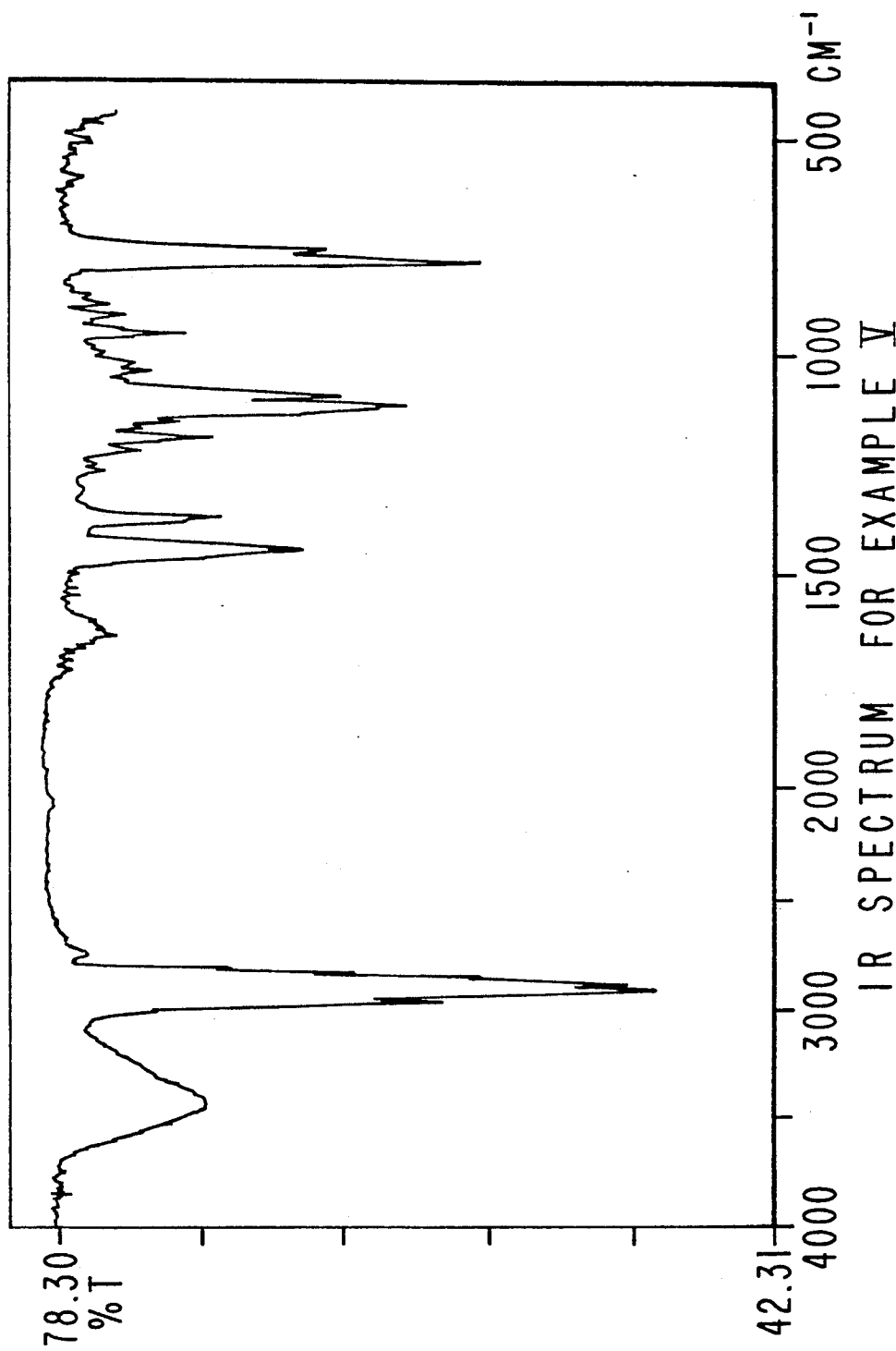
FIG. 16 — IR SPECTRUM FOR EXAMPLE V

GLC PROFILE FOR EXAMPLE VI

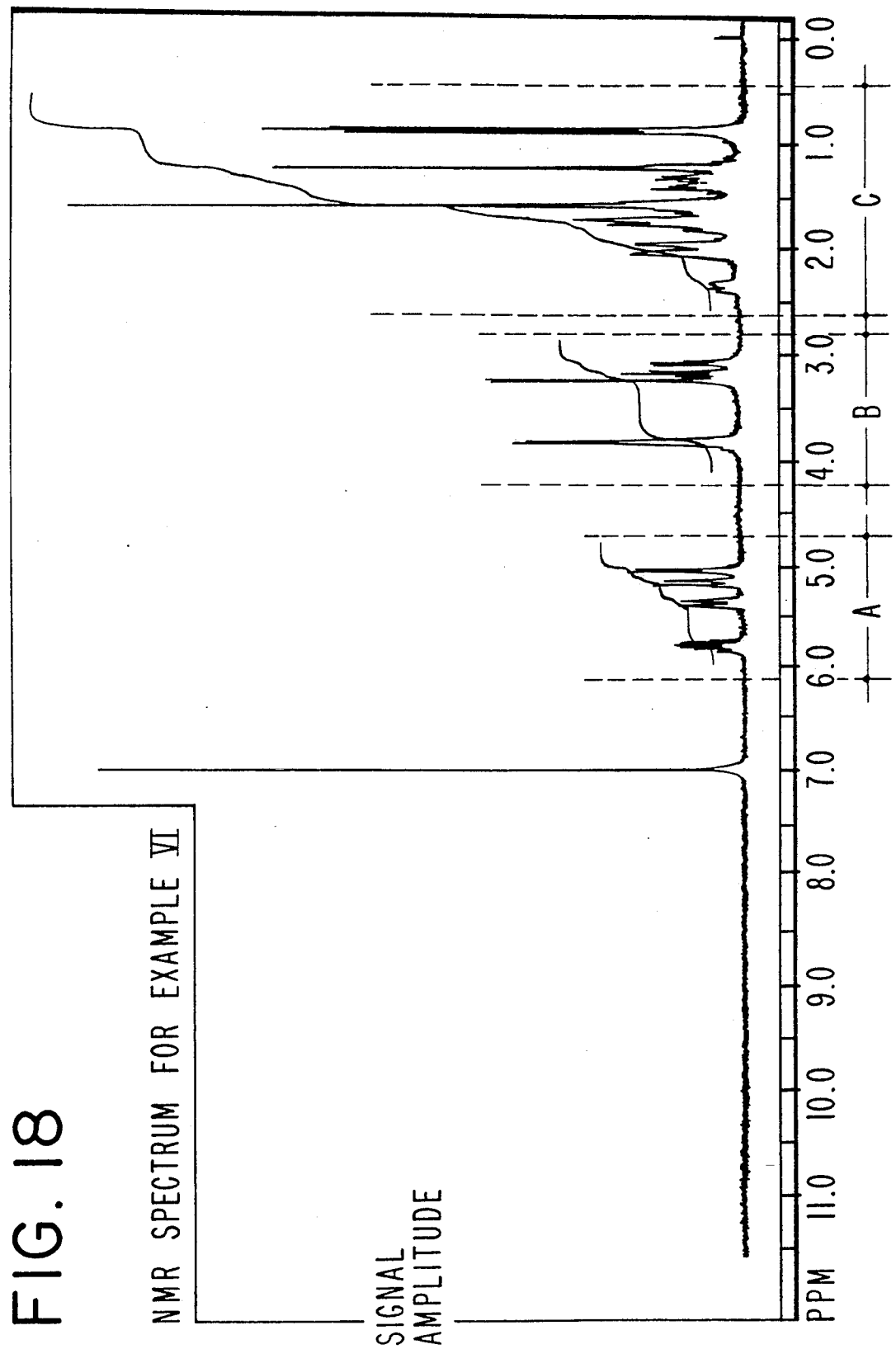
FIG. 18 NMR SPECTRUM FOR EXAMPLE VI

FIG. 18-A
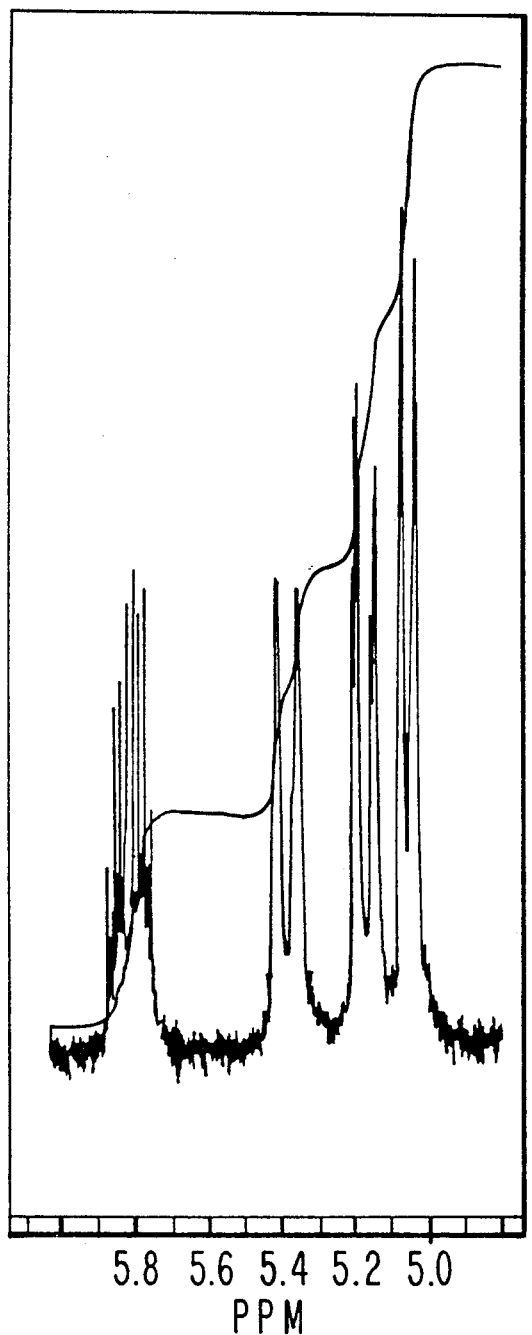
FIG. 18-B
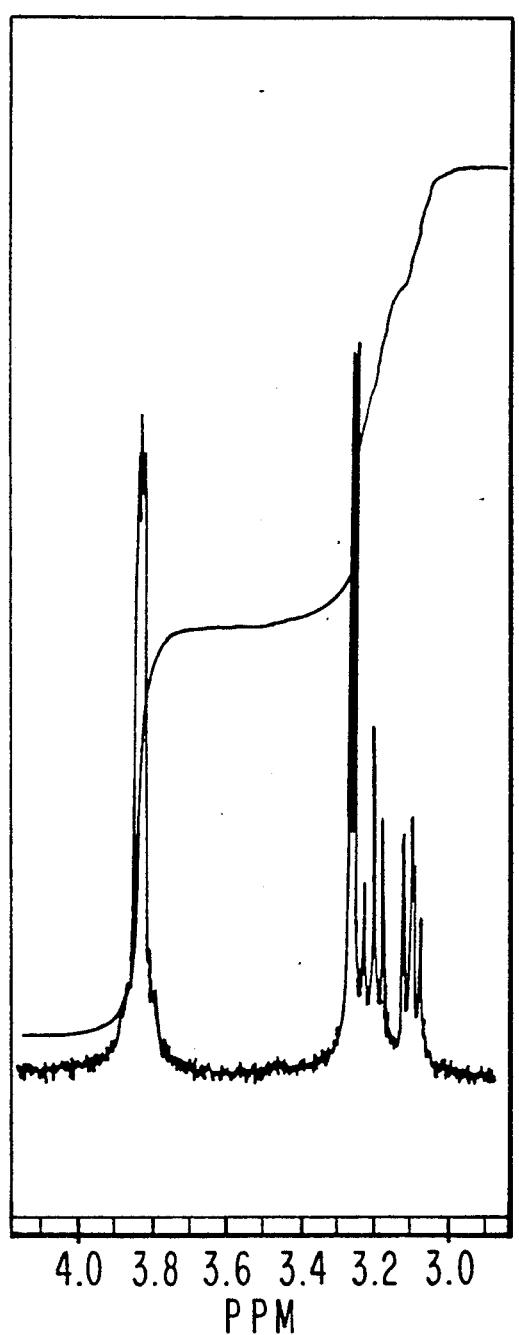

FIG. 18-C
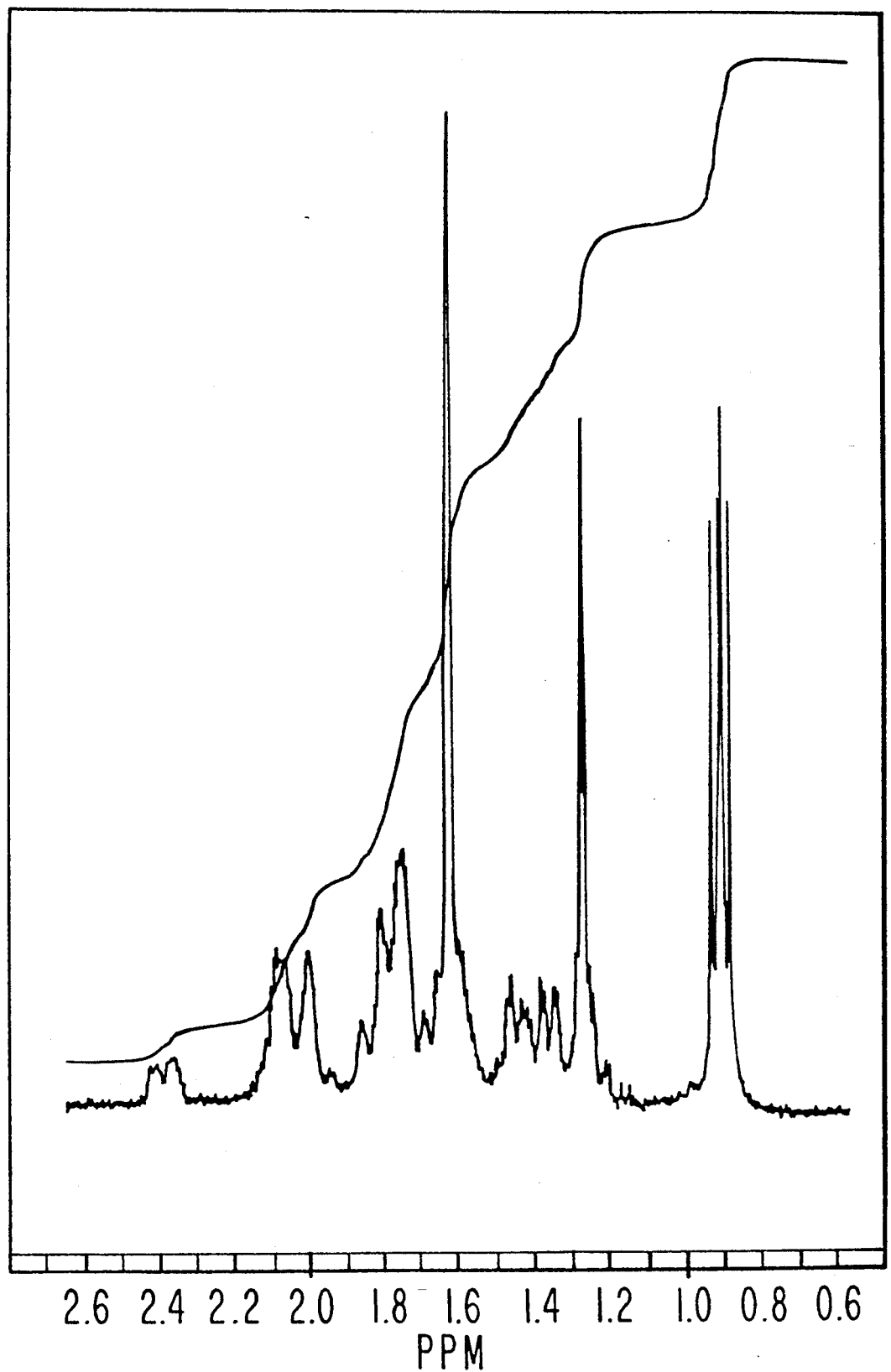

IR SPECTRUM FOR EXAMPLE VI

GLC PROFILE FOR EXAMPLE VII.

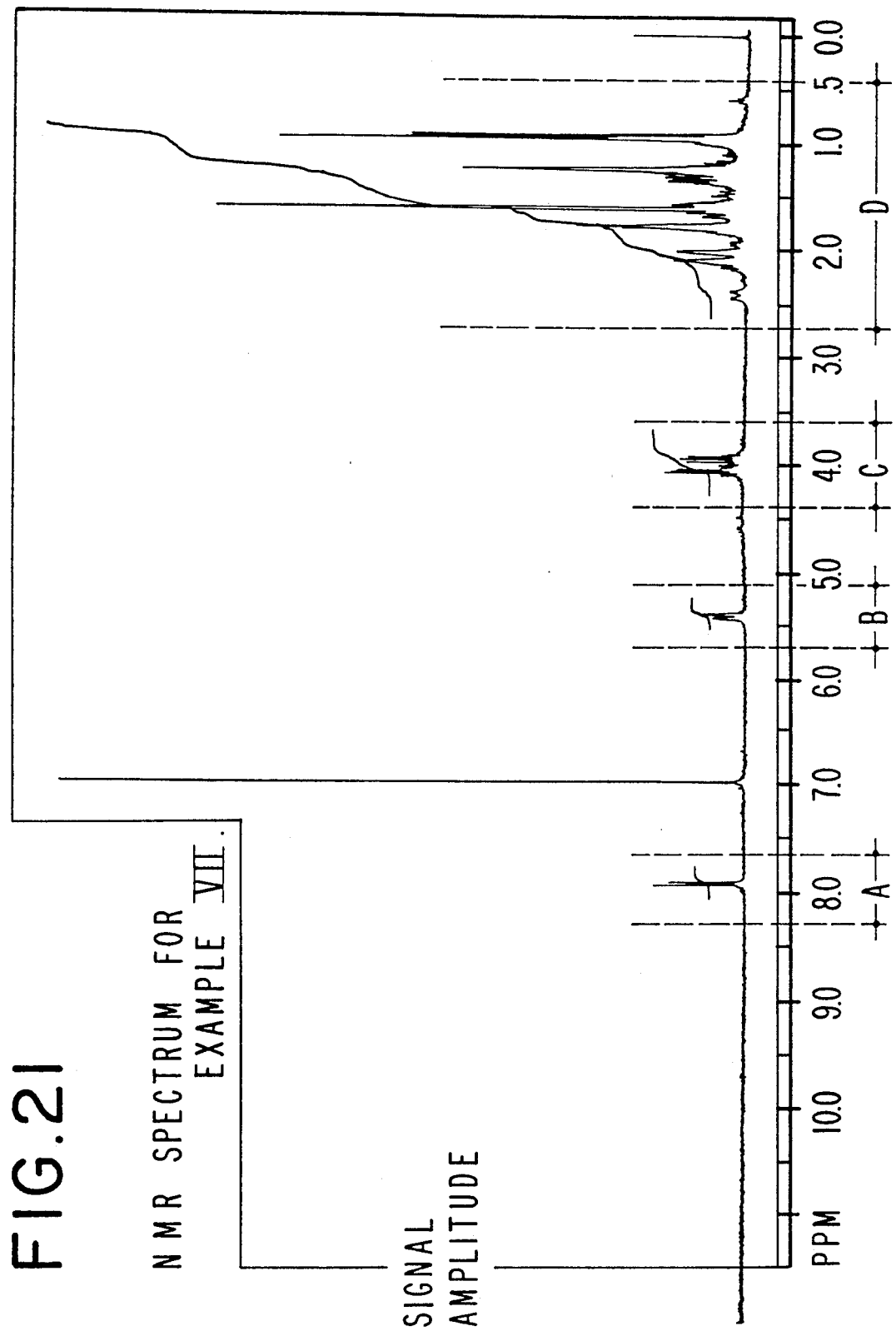
FIG.21 NMR SPECTRUM FOR EXAMPLE VII.

FIG.21-A   FIG.21-B   FIG.21-C
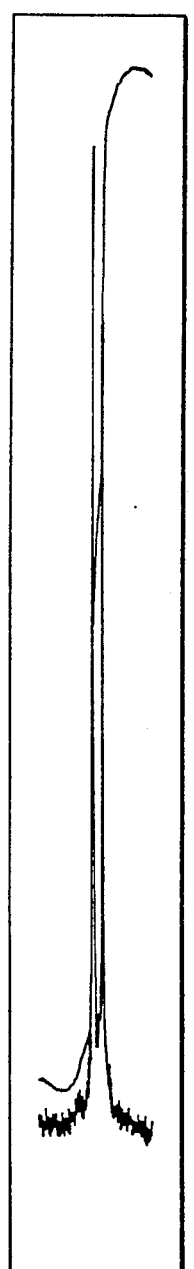
8.0
PPM
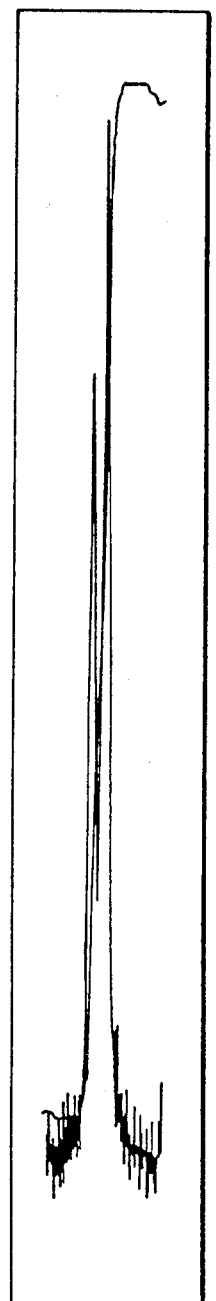
5.4
PPM
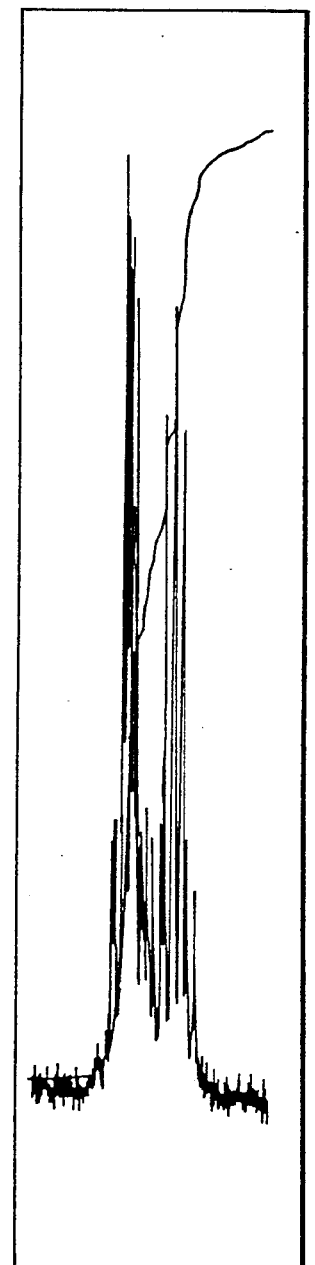
4.2  4.0  3.8
PPM

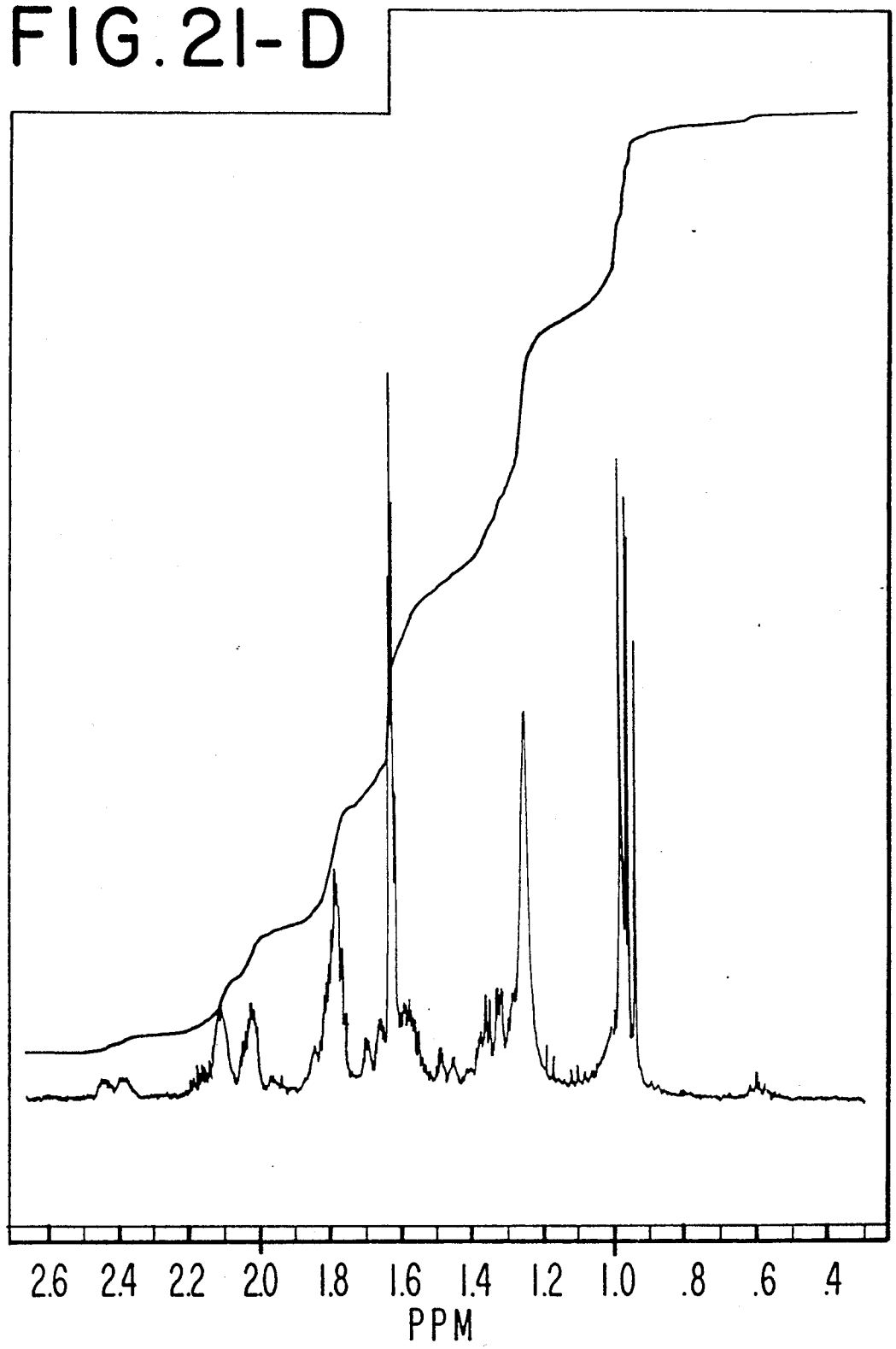
FIG. 21-D

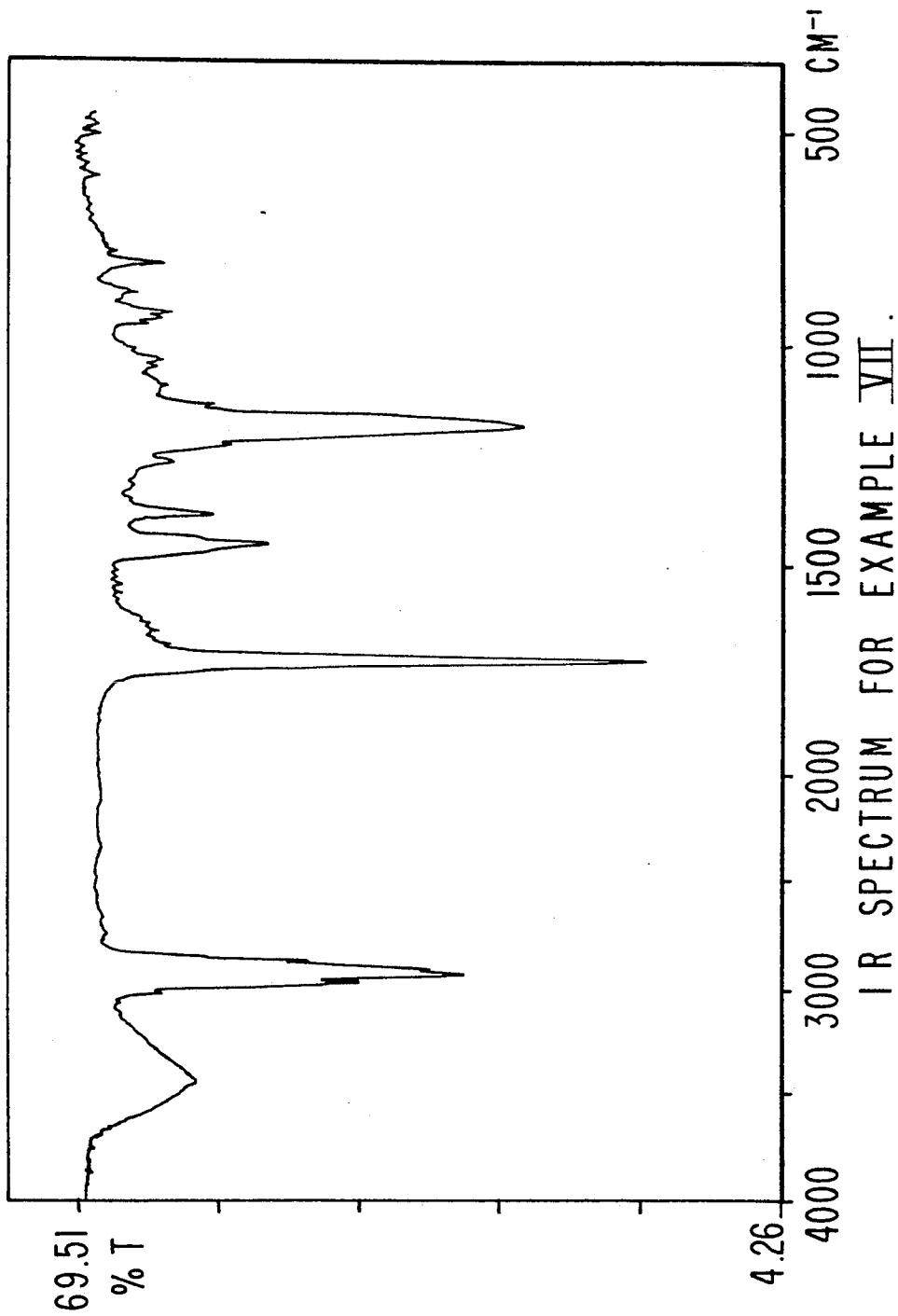
FIG. 22  IR SPECTRUM FOR EXAMPLE VII.

GLC PROFILE FOR EXAMPLE VIII

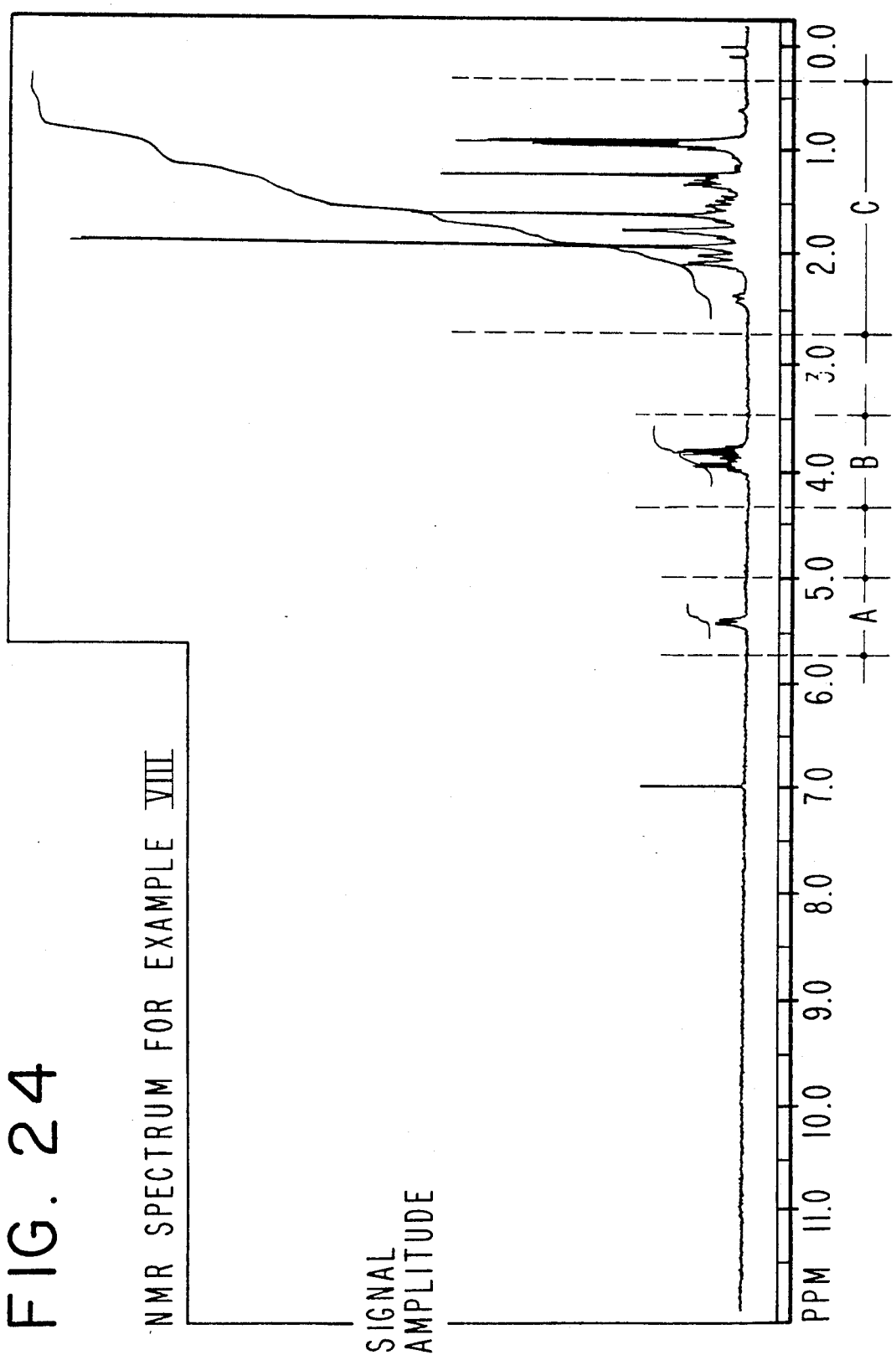

FIG. 24-A
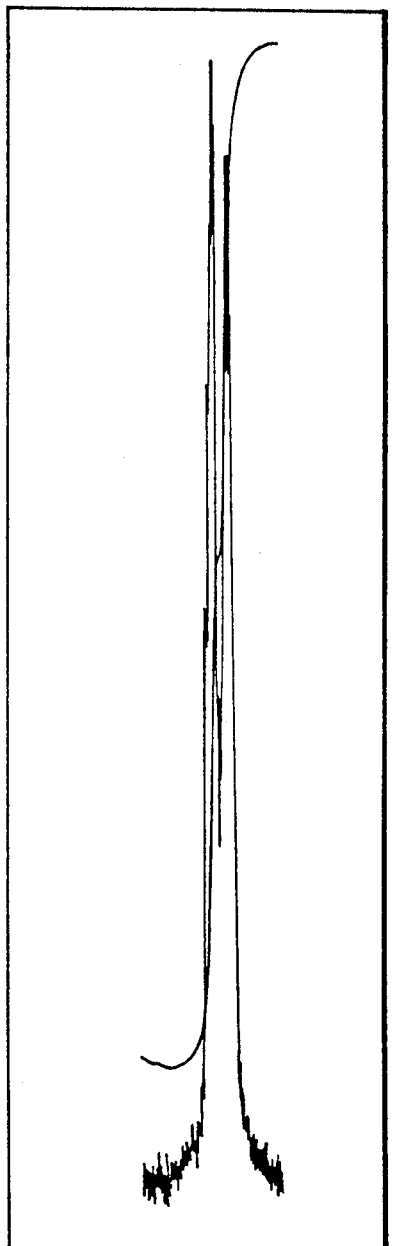
5.4
PPM
FIG. 24-B
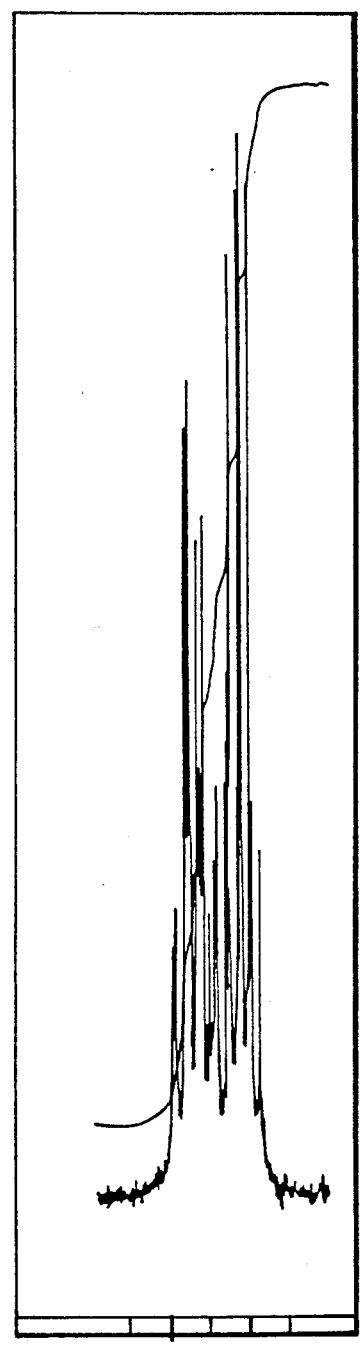
4.0  3.8
PPM

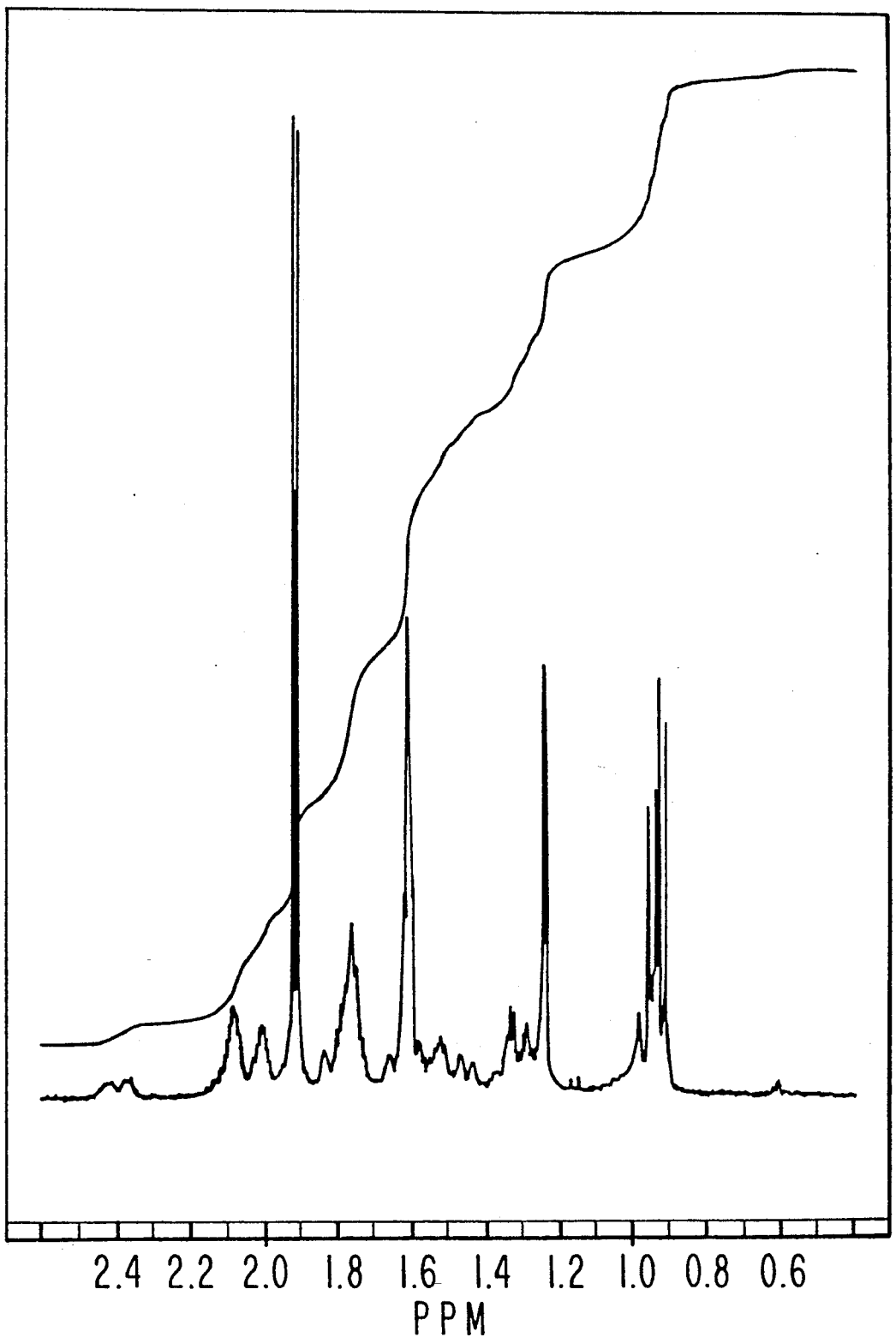
FIG. 24-C

GLC PROFILE FOR EXAMPLE IX

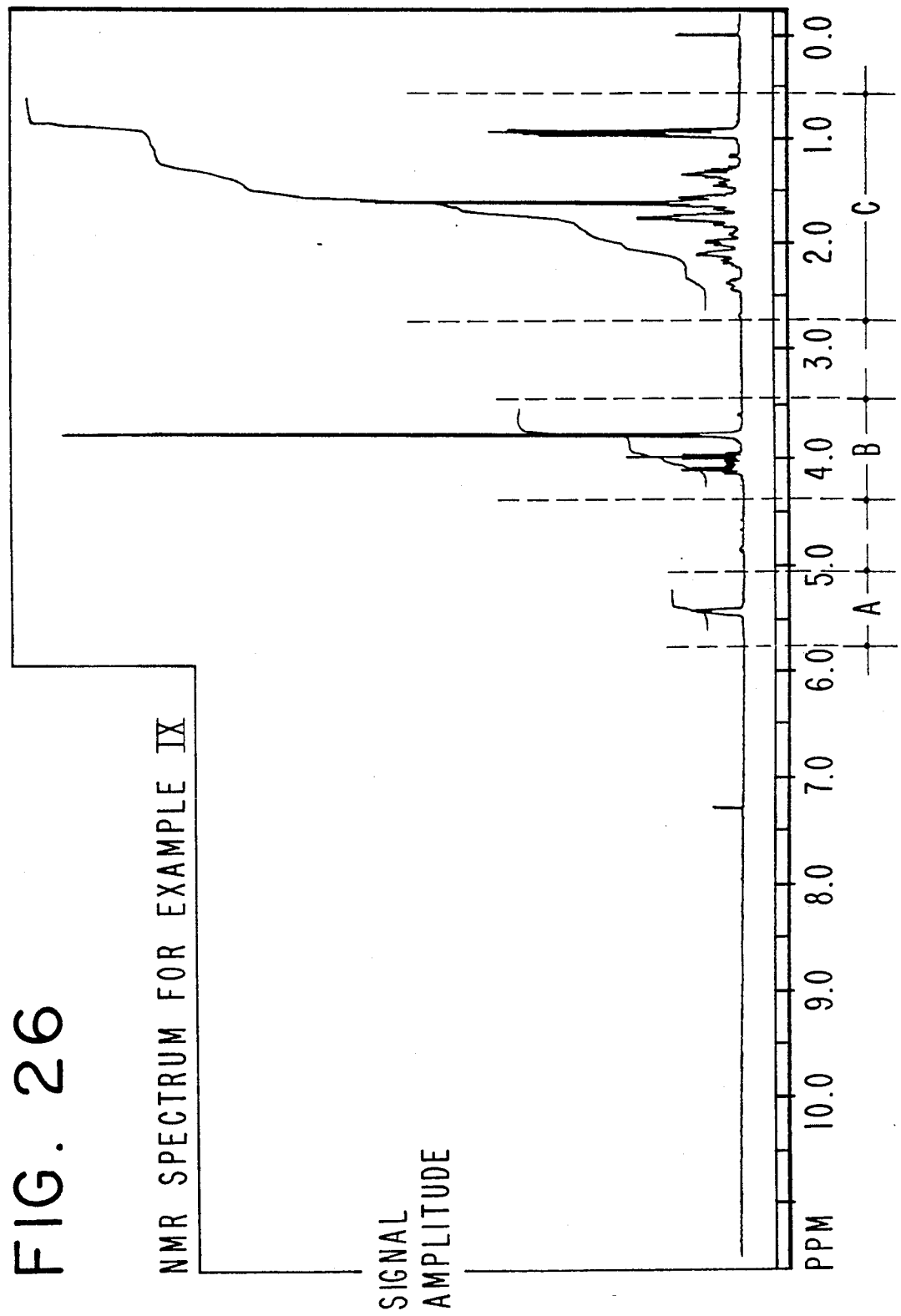
FIG. 26 NMR SPECTRUM FOR EXAMPLE IX

FIG. 26-A
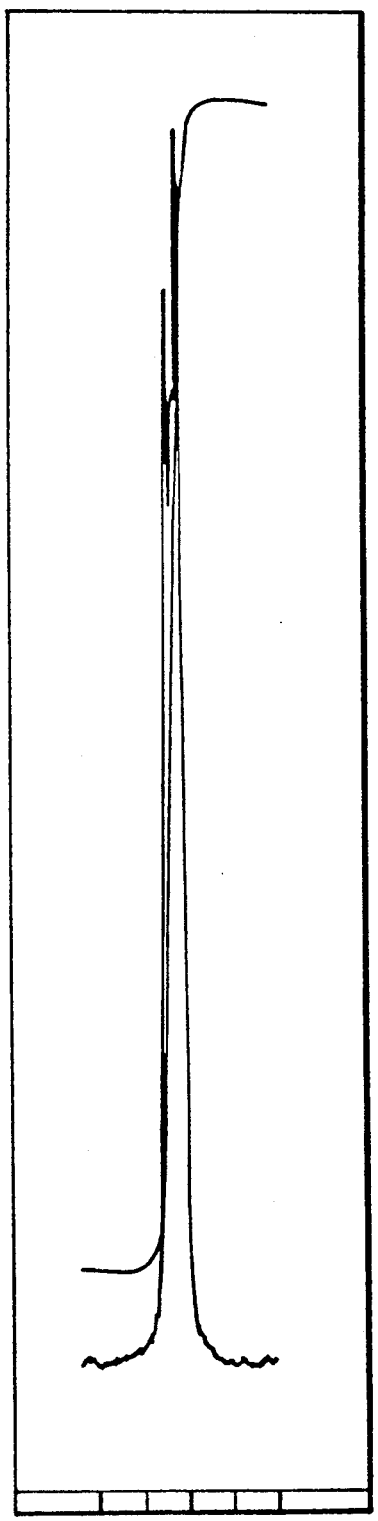
5.4
PPM
FIG. 26-B
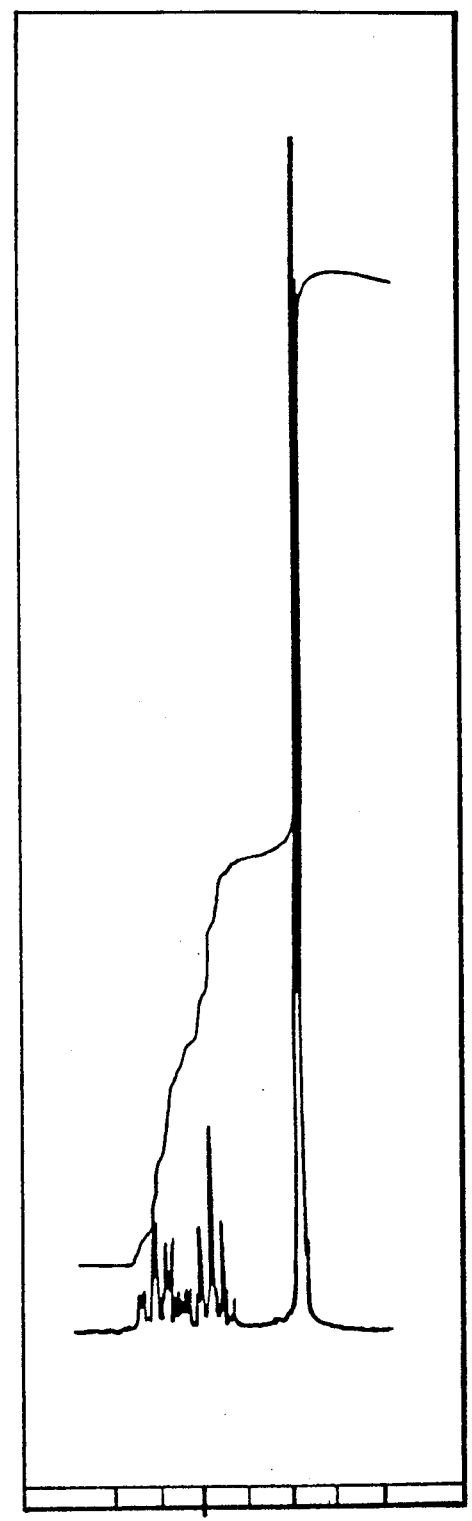
4.2  4.0  3.8
PPM

FIG. 26-C
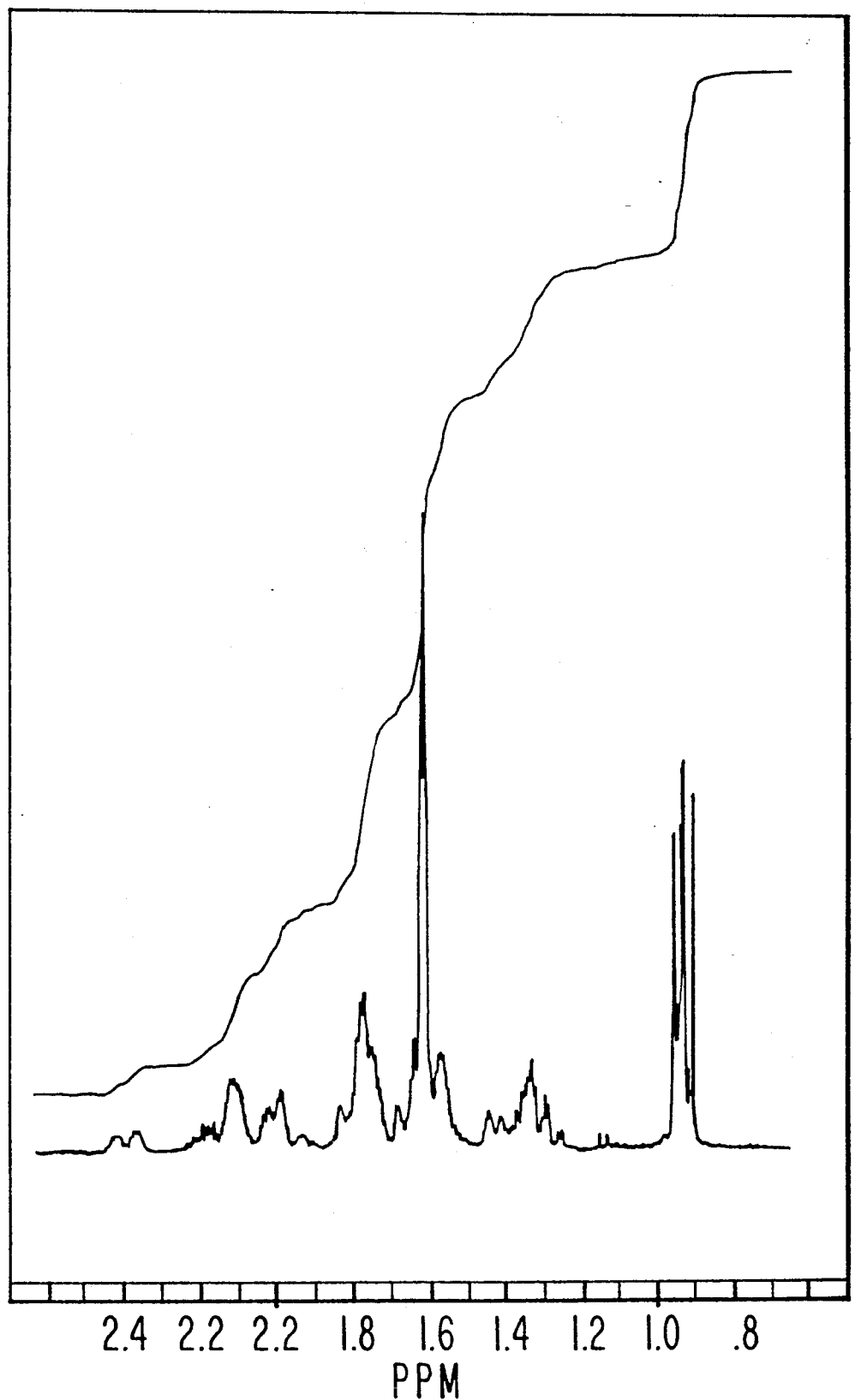

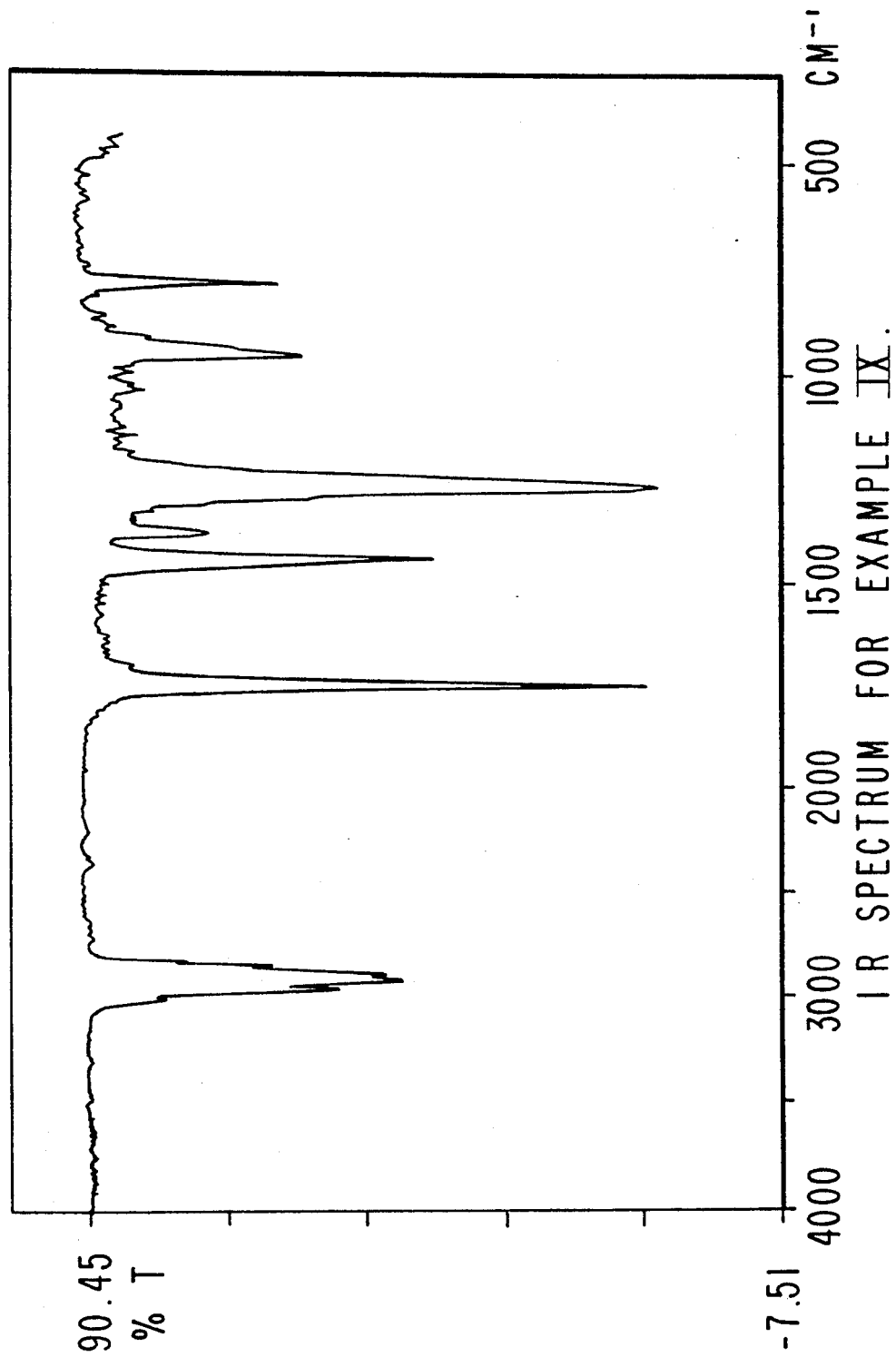
FIG.27 IR SPECTRUM FOR EXAMPLE IX.

GLC PROFILE FOR EXAMPLE X

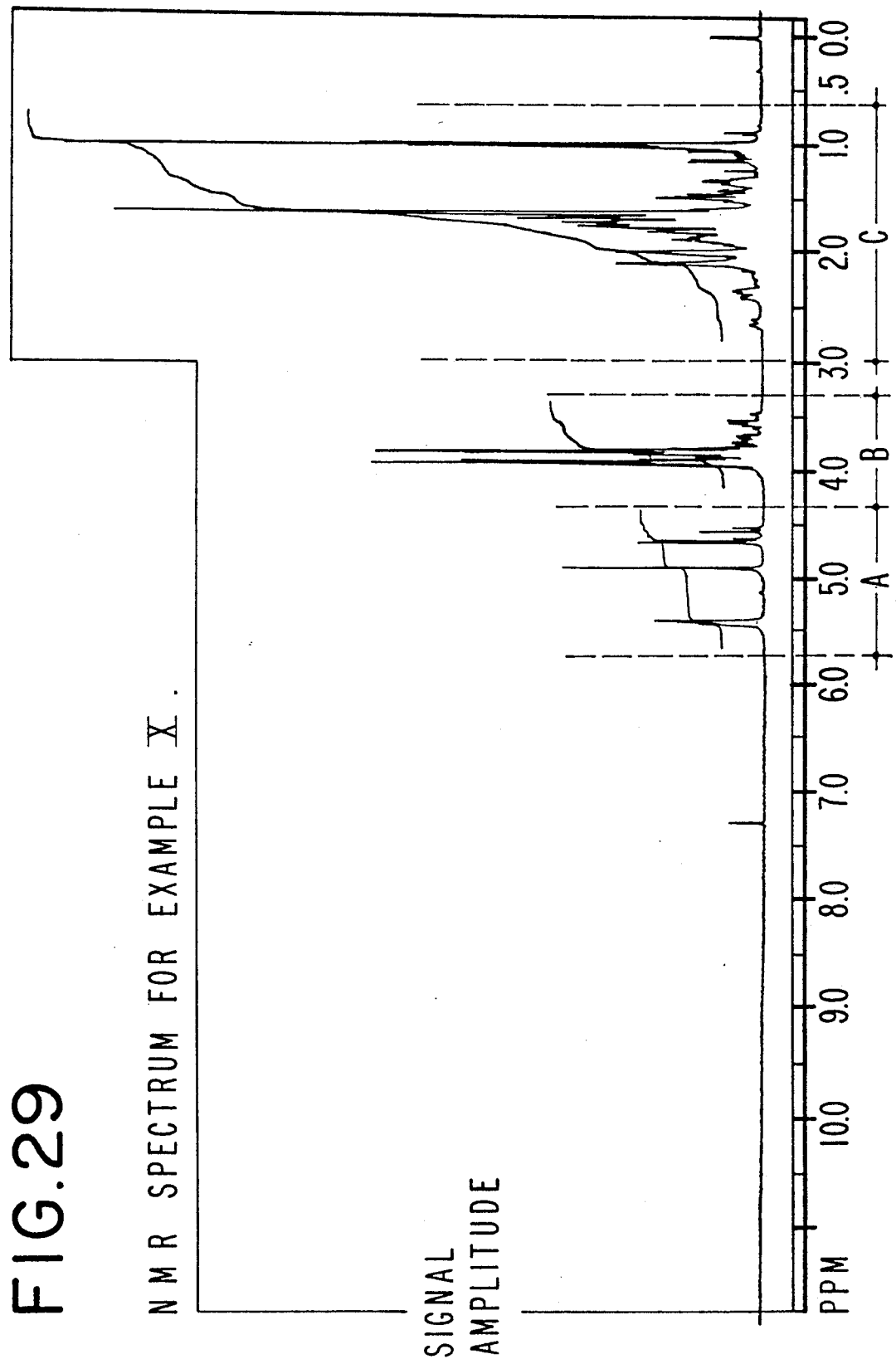

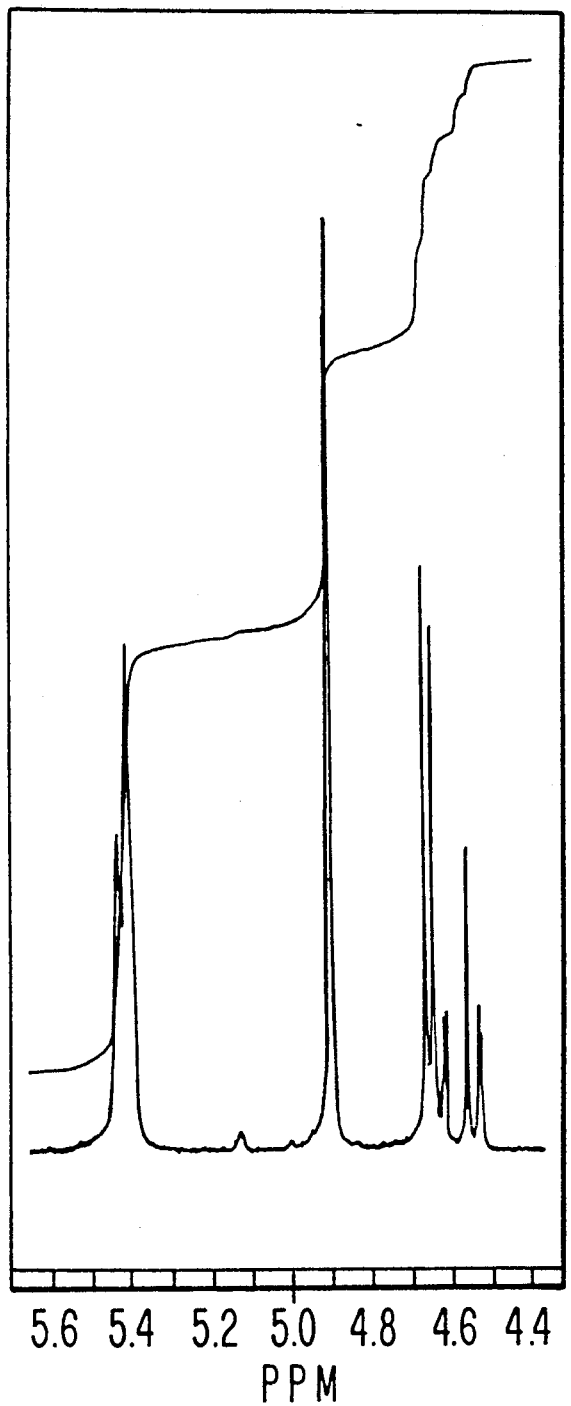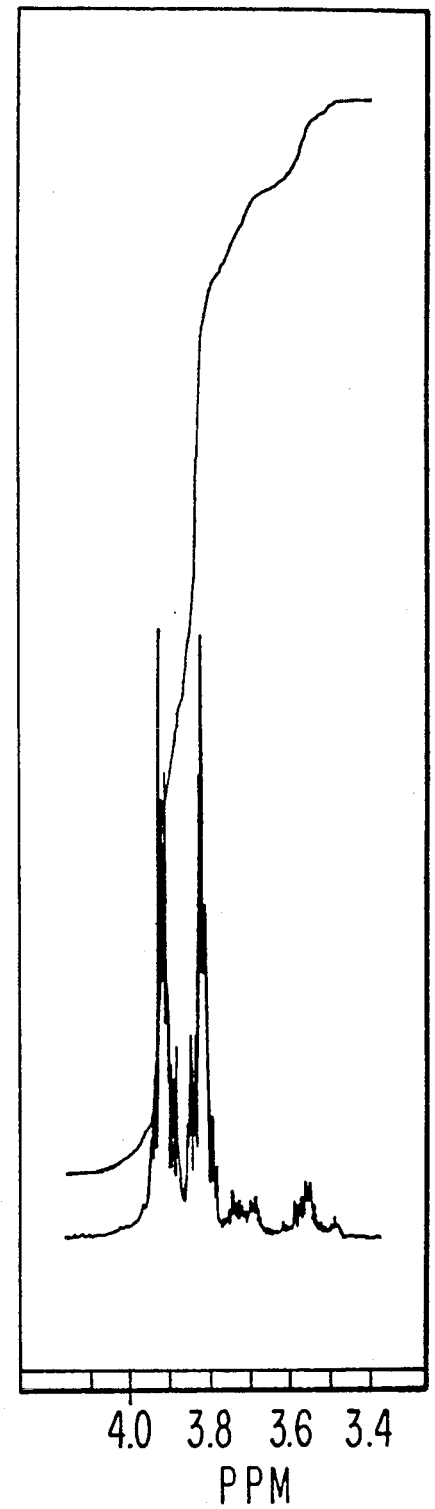

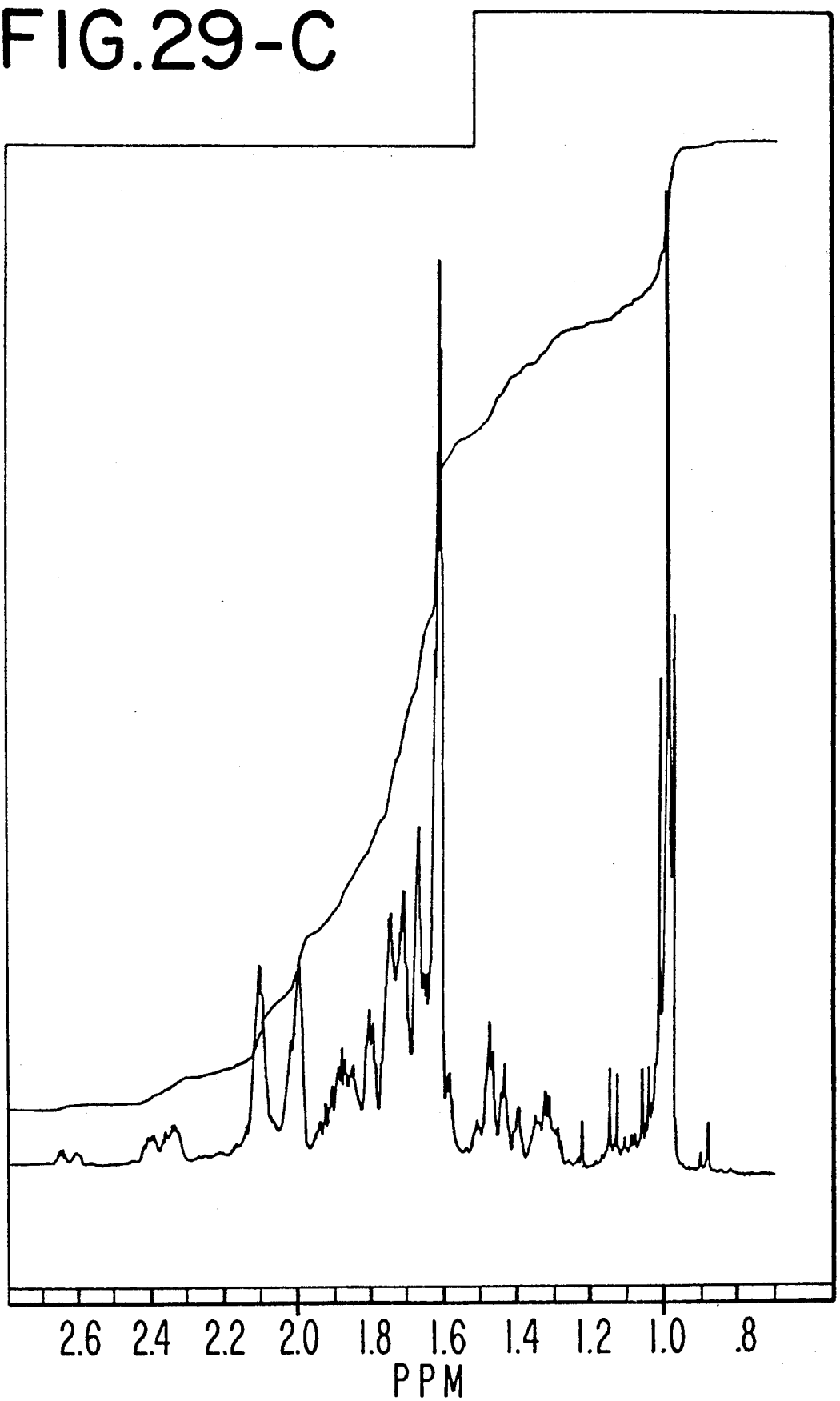
FIG.29-C

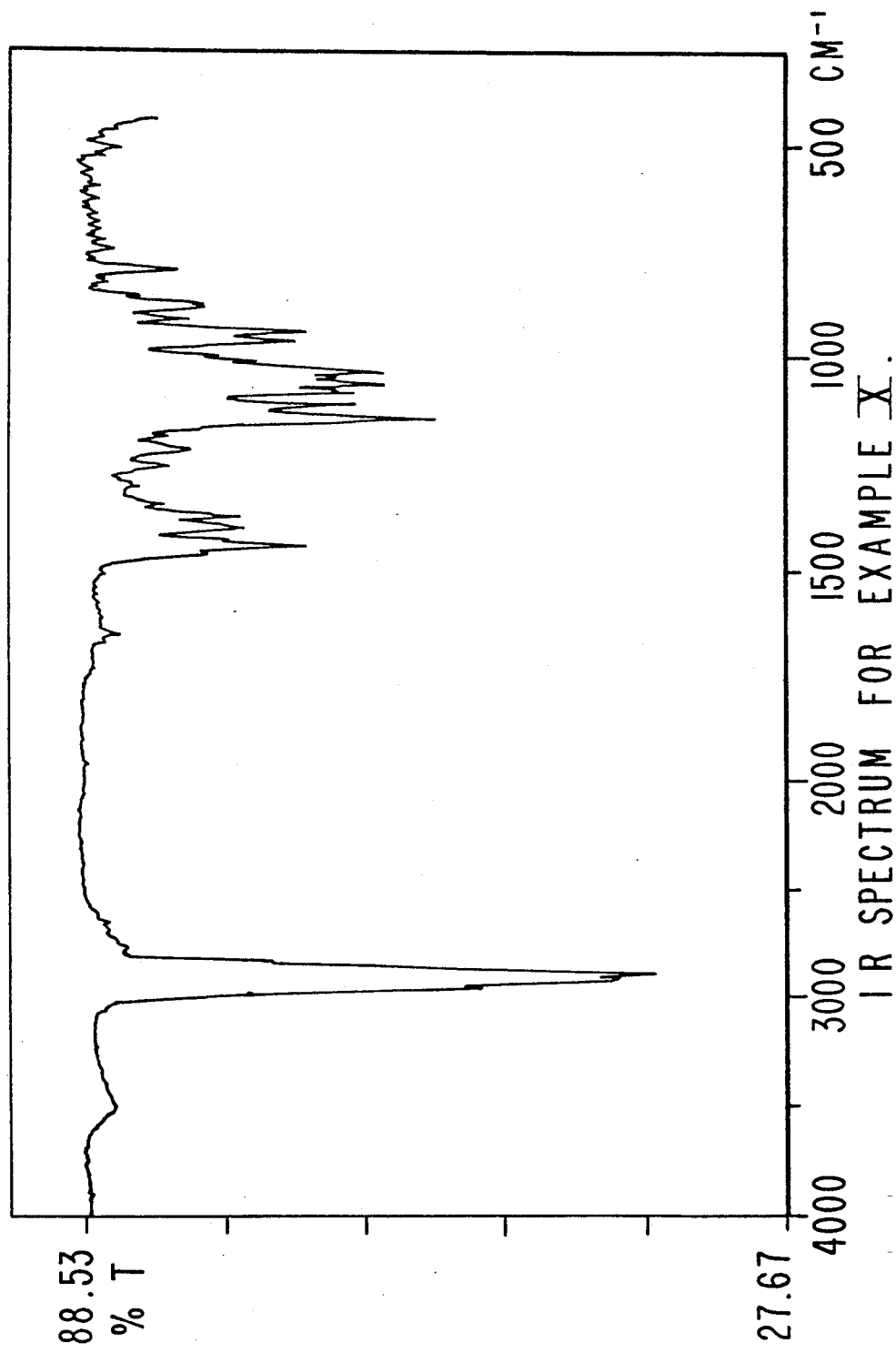
FIG. 30 IR SPECTRUM FOR EXAMPLE X.

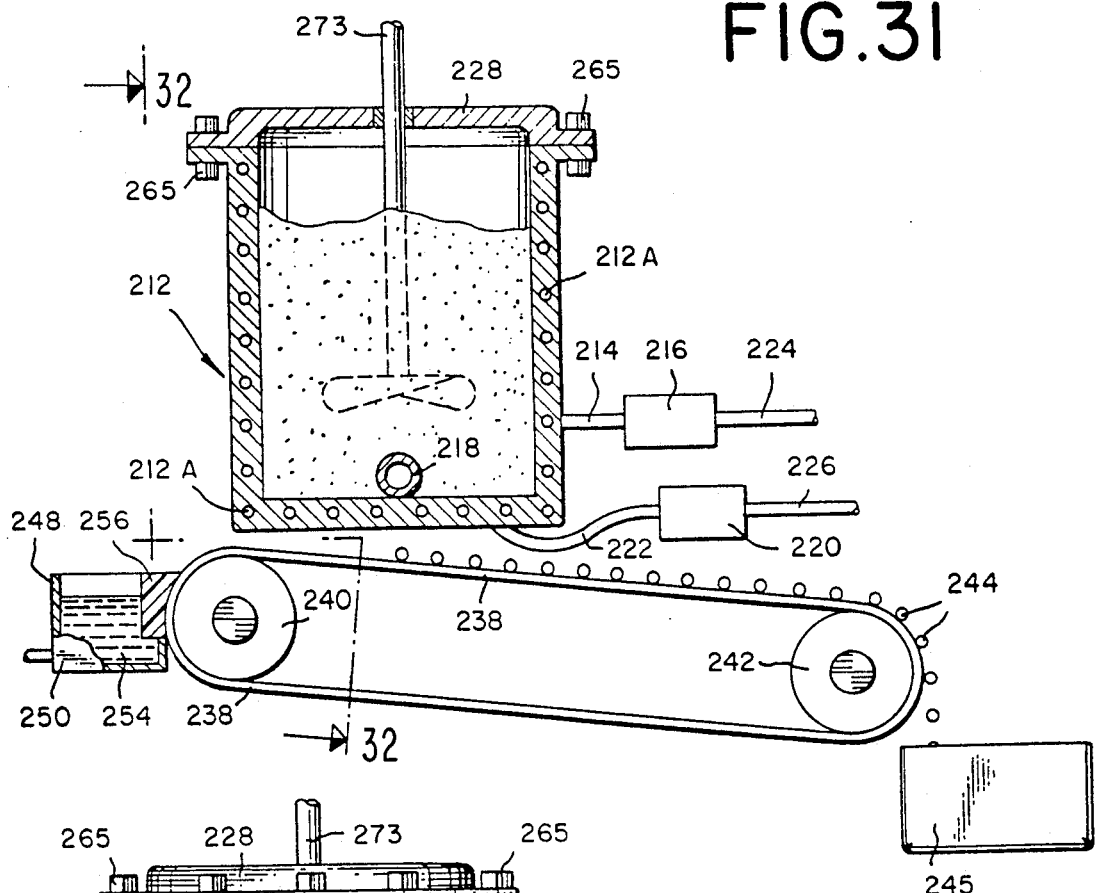

2,6-DIMETHYLBICYCLO[3.3.1]NON-6-ENE-3-METHANOL, SUBSTITUTED DERIVATIVES THEREOF, ORGANOLEPTIC UTILITIES THEREOF, PROCESSES FOR PRODUCING SAME, AND PROCESS INTERMEDIATES THEREFOR

BACKGROUND OF THE INVENTION

Our invention relates to 2,6-dimethylbicyclo[3.3.1]-non-6-ene-3-methanol and substituted derivatives thereof defined according to the generic structure:

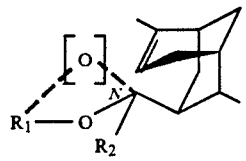

wherein each of the dashed lines represents a carbon-oxygen covalent bond or no bond; N is 0 or 1; $R_1$ represents hydrogen, $C_1$-$C_2$ lower alkyl, lower alkenyl, lower alkylenyl, $C_1$-$C_2$ acyl, alkoxycarbonyl, magnesium halo or lithium; and $R_2$ represents methyl or hydrogen with the proviso that when N is 1, each of the dashed lines are carbon-oxygen covalent bonds; $R_2$ is hydrogen and $R_1$ is only lower alkylenyl; and when N is 0, each of the dashed lines are no covalent bonds and $R_1$ is not lower alkylenyl; and uses of the genus of compounds defined according to the structure:

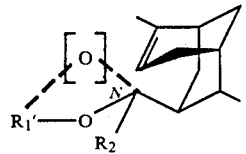

wherein $R_1'$ is hydrogen, $C_1$-$C_2$ lower alkyl, lower alkenyl, lower alkylenyl or $C_1$-$C_2$ acyl; $R_2$ is methyl or hydrogen; and each of the dashed lines represents a carbon-oxygen covalent bond or no bond and N is 0 or 1 with the proviso that when N is 1, each of the dashed lines are carbon-oxygen covalent bonds; $R_2$ is hydrogen and $R_1'$ is only lower alkylenyl; and when N is 0, each of the dashed lines are no covalent bonds and $R_1'$ is not lower alkylenyl in augmenting or enhancing the aroma of consumable materials including but not limited to perfume compositions, perfumed articles, colognes, deodorizing articles, deodorizing compositions and malodor maskants.

There has been considerable work performed relating to substances which can be used to impart (modify, augment or enhance) fragrances to (or in) various consumable materials. These substances are used to diminish the use of natural materials some of which may be in short supply and to provide more uniform properties in the finished product.

Long-lasting, substantive and intense green, early morning forest path, sandalwood, piney, camphoraceous, geranium, rhodinol, peppery, woody, orris, orivone, sweet and grapefruit-like aromas with natural piney, green, woody, pine needle, sappy, camphoraceous, rhod inol, peppery, and orivone topnotes and "cooling" undertones are desirable in several types of perfume compositions, perfumed articles, colognes, deodorizing compositions and odor maskant materials.

The use of polycyclic alcohols and derivatives thereof such as ethers and esters for augmenting or enhancing the aroma of consumable materials including perfume compositions, perfumed articles, colognes, deodorizing articles, deodorizing compositions and malodor maskants is described in U.S. Pat. No. 5,021,184 issued on Jun. 4, 1991 wherein adamantane derivatives defined according to the generic structure:

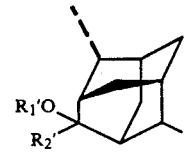

are described for use for augmenting or enhancing the aroma of consumable materials such as perfume compositions, perfumed articles, colognes, deodorizing articles, deodorizing compositions and realodor maskants (wherein $R_1'$ represents hydrogen, acyl or alkyl; and $R_2'$ is hydrogen or lower alkyl and the dashed line is a carbon-carbon single bond or a carbon-carbon double bond).

Nothing in the prior art however discloses the unexpected, unobvious and advantageous organoleptic properties of the 2,6-dimethylbicyclo[3.3.1]non-6-ene-3-methanol and substituted derivatives thereof of our invention; and the structure of the 2,6-dimethylbicyclo[3.3.1]non-6-ene-3-methanol and substituted derivatives thereof of our invention are different in kind from the structures of the adamantane derivatives of U.S. Pat. No. 5,021,184 issued on Jun. 4, 1991.

BRIEF DESCRIPTIONS OF THE DRAWINGS

FIG. 1 is the GLC profile for the starting material for th action of Example I having the structure:

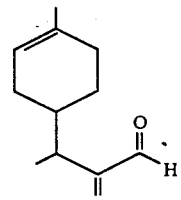

(Conditions: Carbowax column programmed at 130°-220° C. at 8° C. per minute).

FIG. 2 is the GLC profile for the reaction product of Example I containing the compound having the structure:

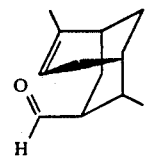

FIG. 3 is the NMR spectrum for the compound having the structure:

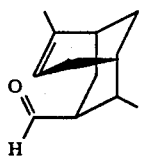

prepared according to Example I.

FIGS. 3A, 3B and 3C are enlargements of sections "A", "B" and "C" of the NMR spectrum of FIG. 3.

FIG. 4 is the infrared spectrum for the compound having the structure:

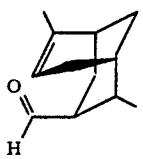

prepared according to Example I.

Figure 5:
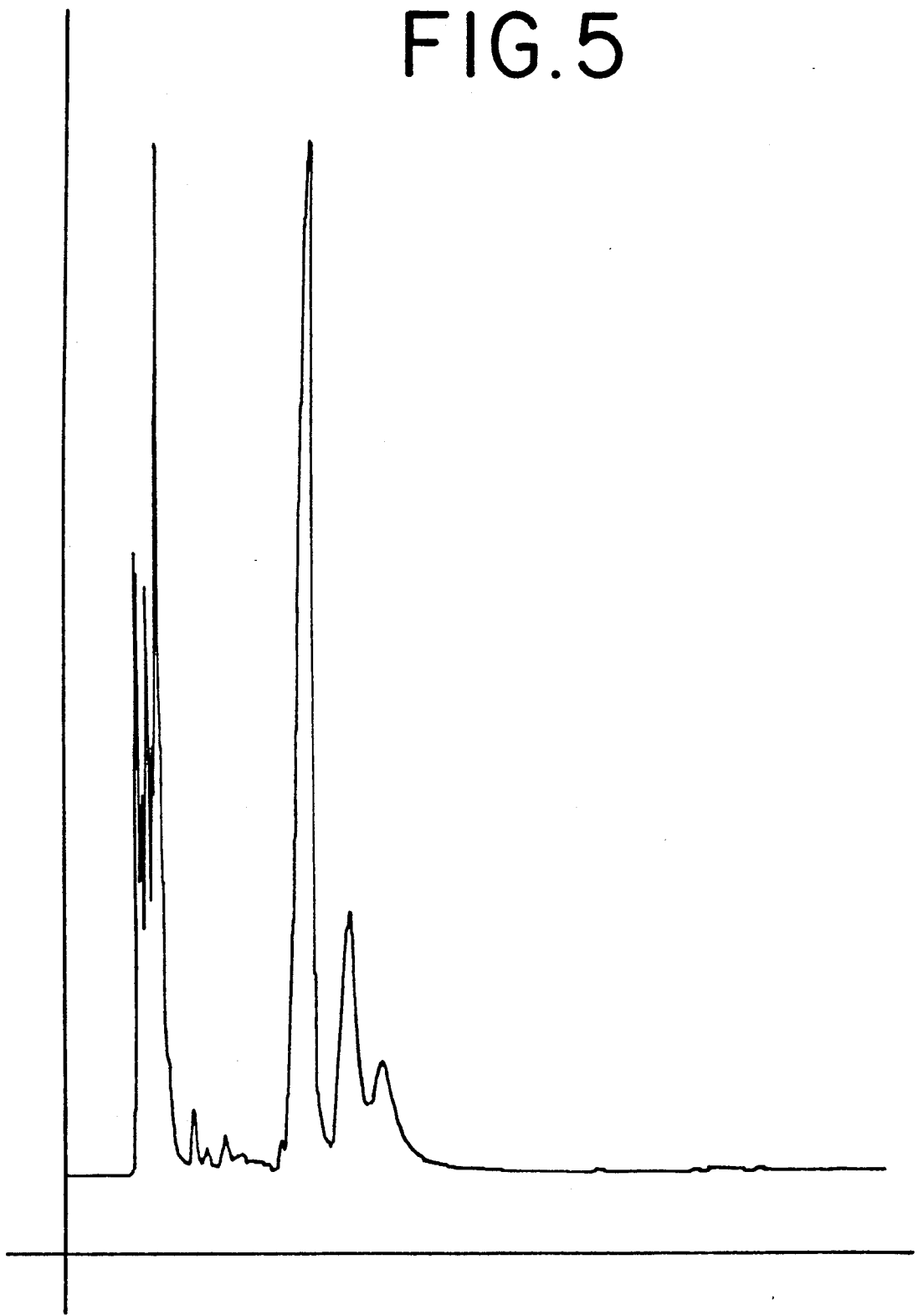

FIG. 5 is the GLC profile for the reaction product of Example II containing the compound having the structure:

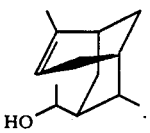

FIG. 6 is the NMR spectrum for the compound having the structure:

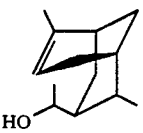

prepared according to Example II.

FIGS. 6A, 6B and 6C are enlargements of sections "A", "B" and "C" of the NMR spectrum of FIG. 6.

FIG. 7 is the infrared spectrum for the compound having the structure:

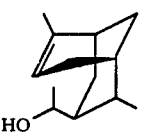

prepared according to Example II.

Figure 8:
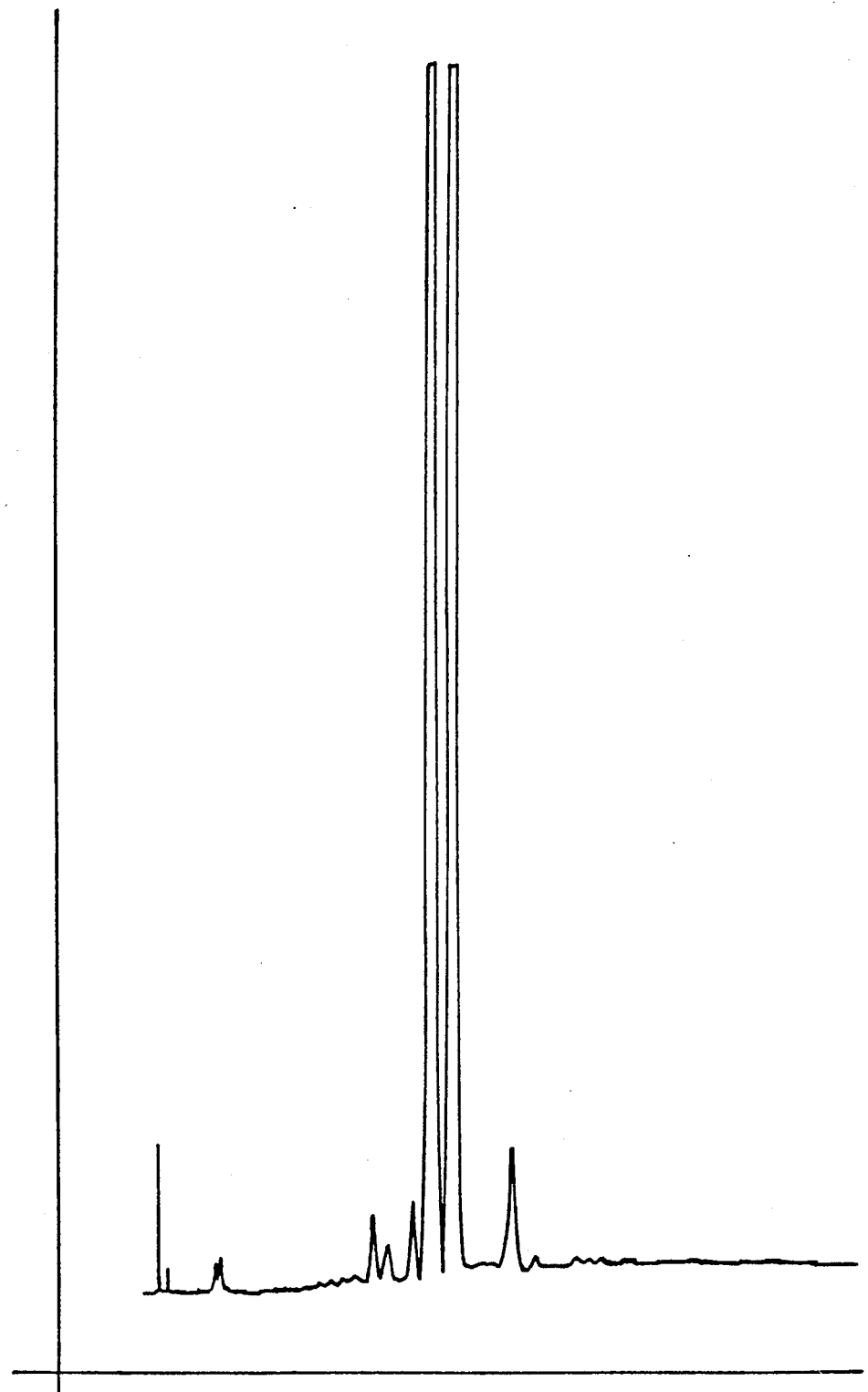

FIG. 8 is the GLC profile for the reaction product of Example III containing the compound having the structure:

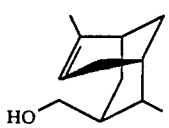

(Conditions: Carbowax column programmed at 130°–220° C. at 8° C. per minute).

FIG. 9 is the NMR spectrum for the compound having the structure:

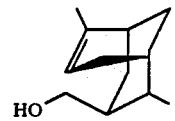

prepared according to Example III.

FIGS. 9A, 9B and 9C are, respectively, enlargements of sections "A", "B" and "C" of the NMR spectrum of FIG. 9.

Figure 10:
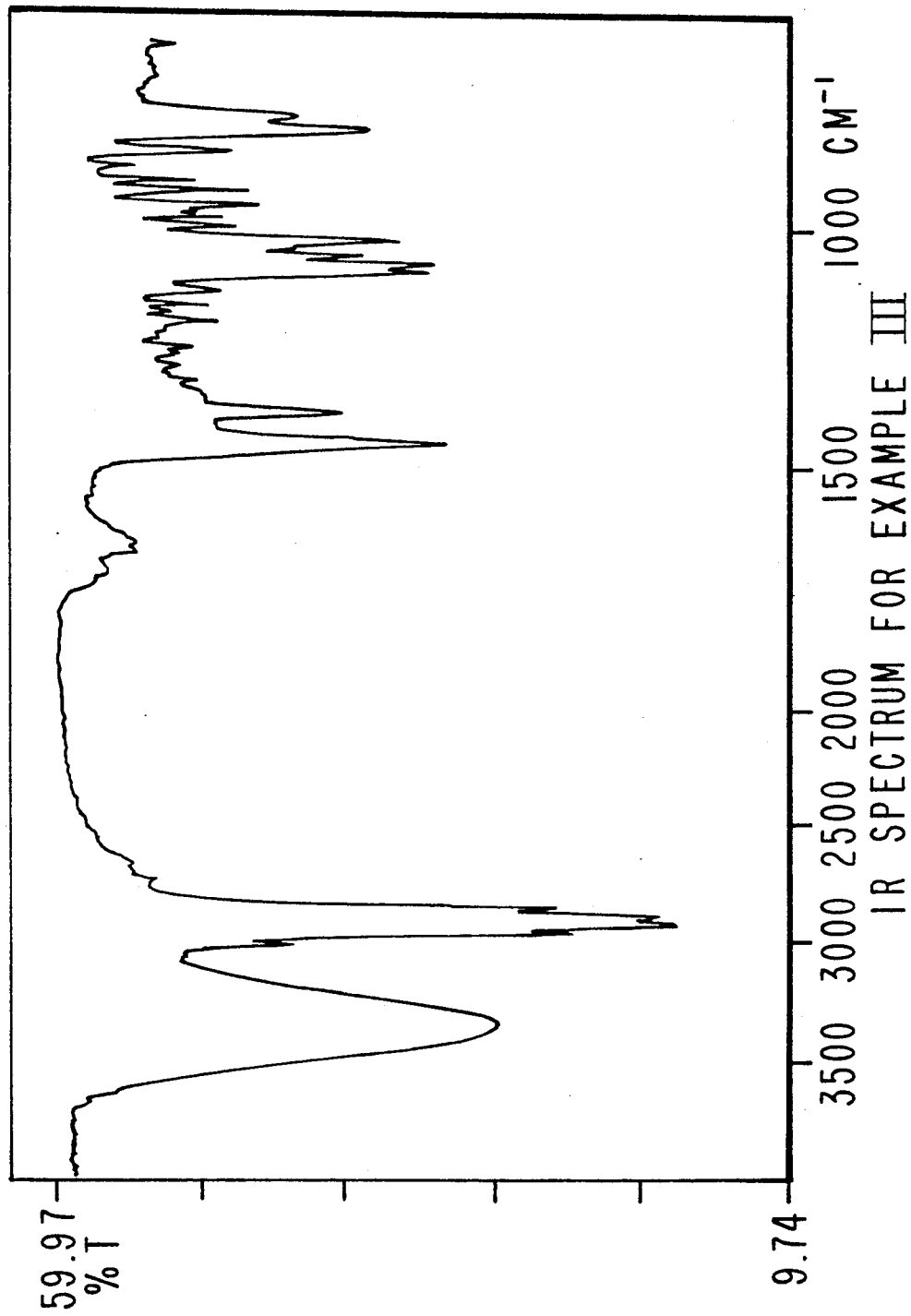

FIG. 10 is the infrared spectrum for the compound having the structure:

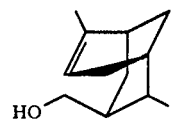

prepared according to Example III.

Figure 11:
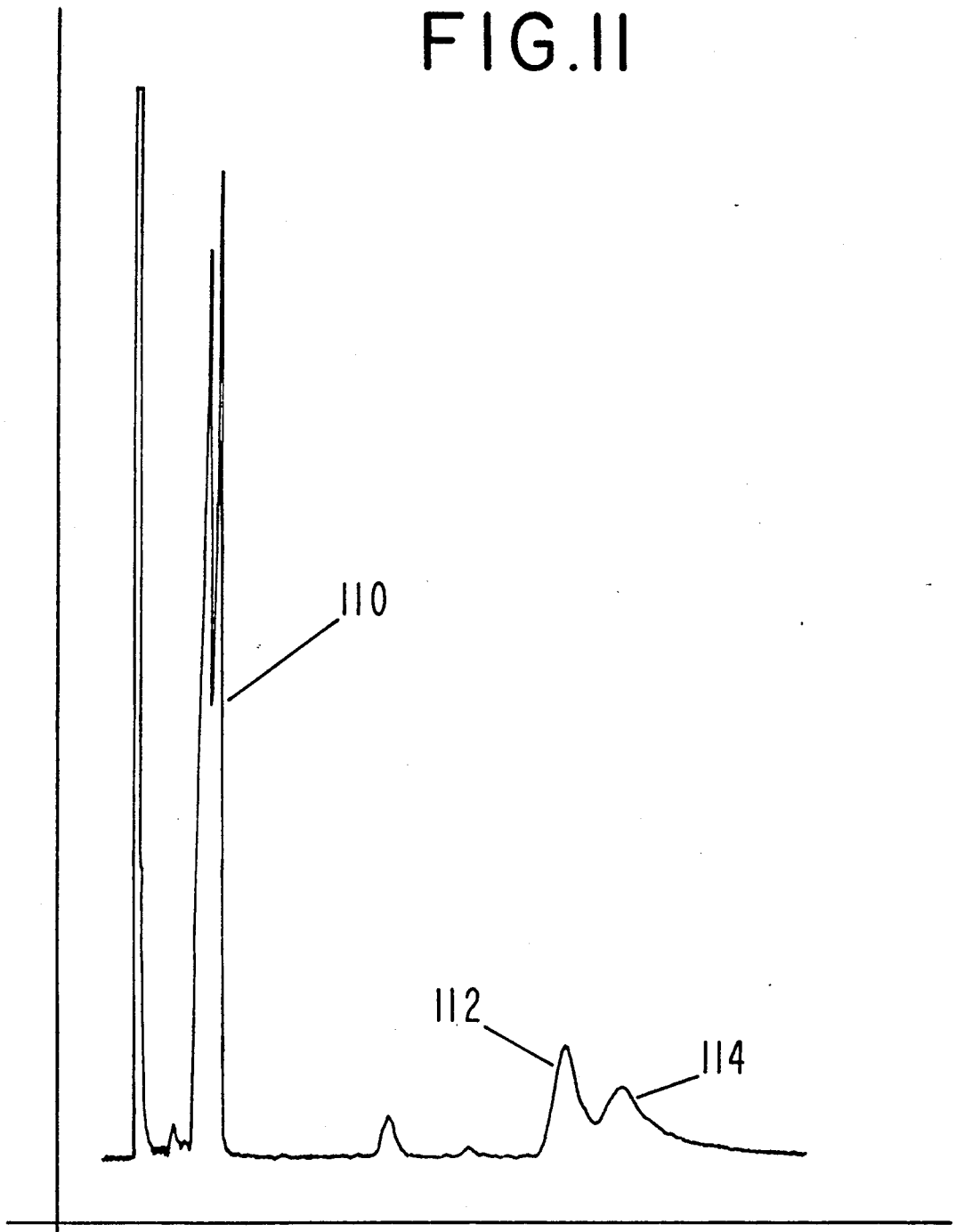

FIG. 11 is the GLC profile for the reaction product of Example IV containing the compound having the structure:

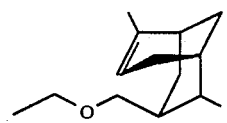

(Conditions: Carbowax column programmed at 140° C. isothermal).

FIG. 12 is the NMR spectrum for the compound having the structure:

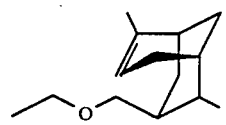

prepared according to Example IV.

FIGS. 12A, 12B and 12C are, respectively, enlargements of sections "A", "B" and "C" of the NMR spectrum of FIG. 12.

FIG. 13 is an infrared spectrum for the compound having the structure:

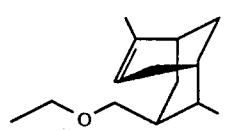

prepared according to Example IV.

Figure 14:
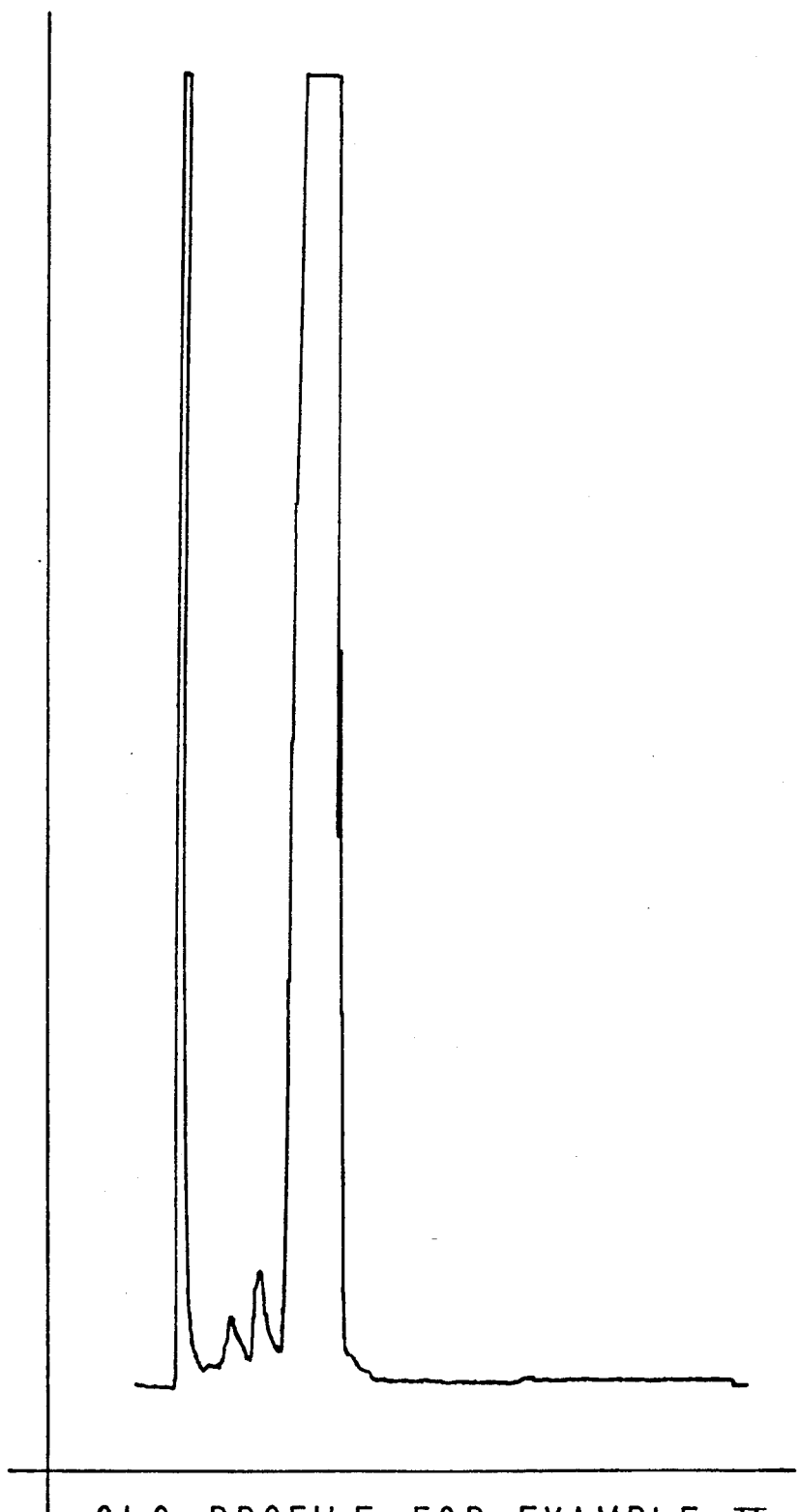

FIG. 14 is the GLC profile for the reaction product of Example V containing the compound having the structure:

FIG. 15 is the NMR spectrum for the compound having the structure:

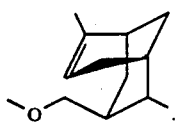

prepared according to Example V.

FIGS. 15A, and 15C are, respectively, enlargements of sections "A", "B" and "C" of the NMR spectrum of FIG. 15.

FIG. 16 is the infrared spectrum for the compound having the structure:

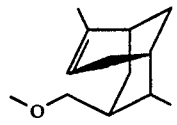

prepared according to Example V.

Figure 17:
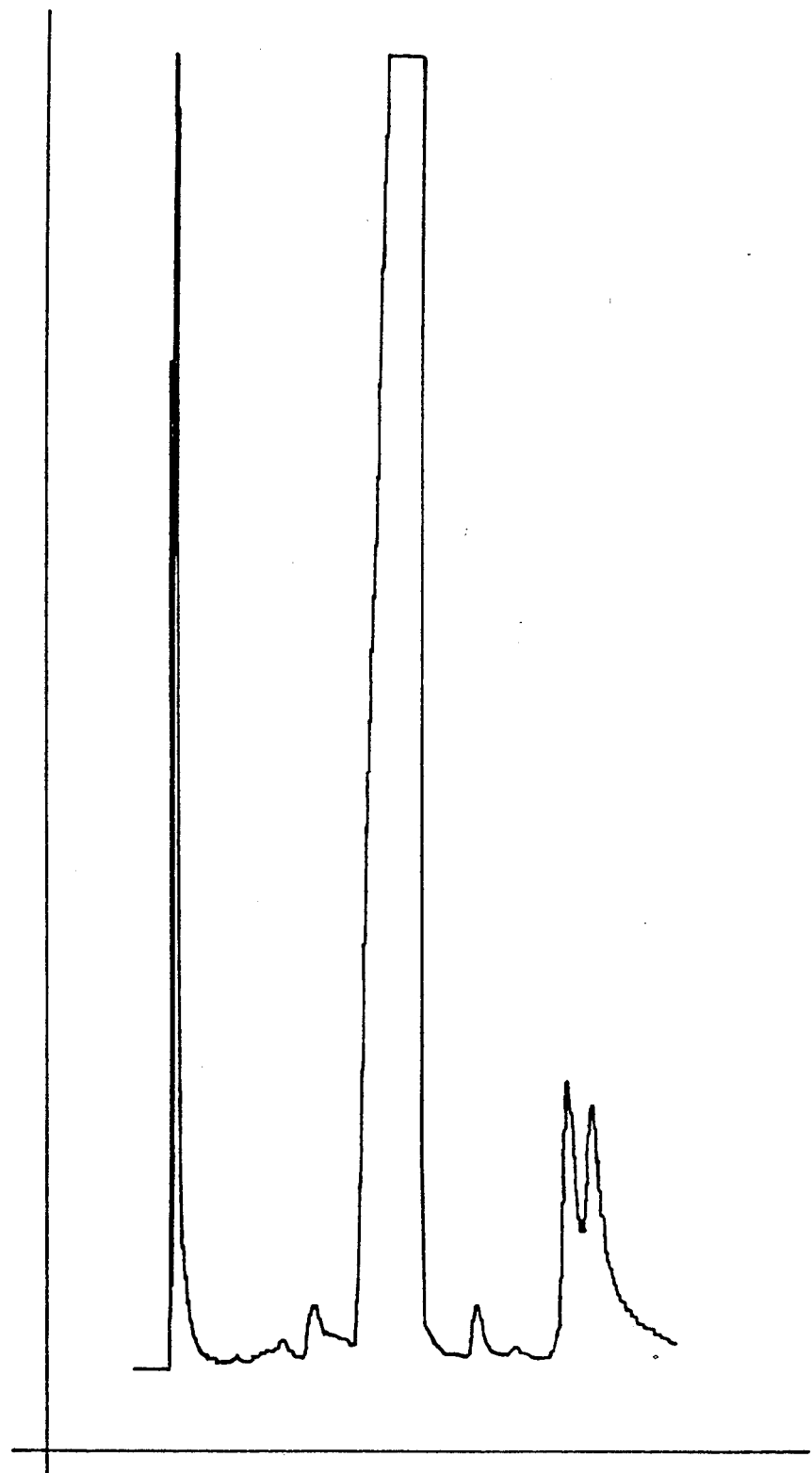

FIG. 17 is the GLC profile for the reaction product of Example VI containing the compound having the structure:

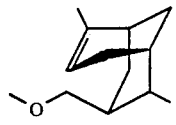

(Conditions: Carbowax column programmed at 150°-220° C. at 8° C. per minute).

FIG. 18 is the NMR spectrum for the compound having the structure:

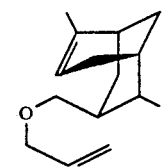

prepared according to Example VI.

FIGS. 18A, 18B and 18C are, respectively, enlargements of sections "A", "B" and "C" of the NMR spectrum of FIG. 18.

Figure 19:
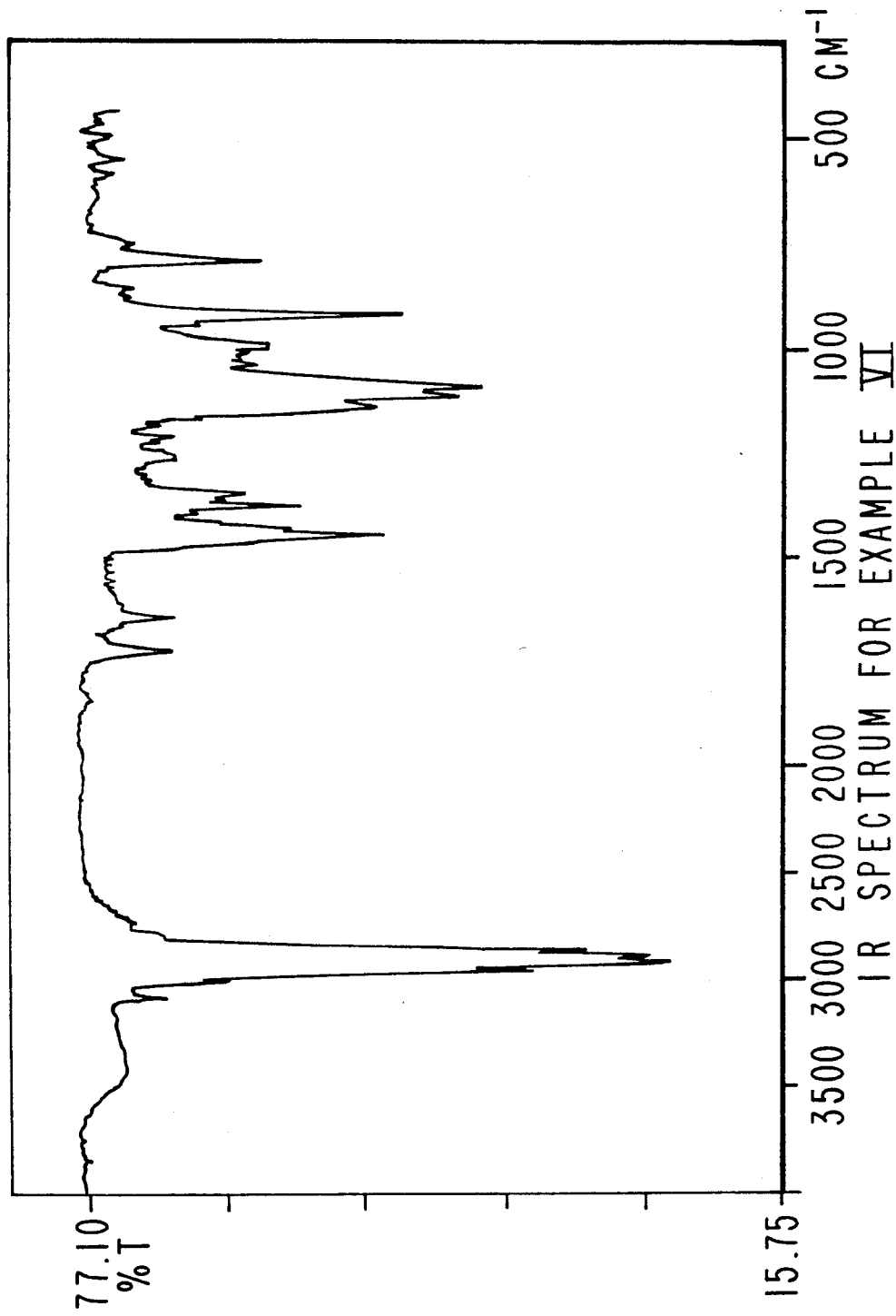

FIG. 19 is the infrared spectrum for the compound having the structure:

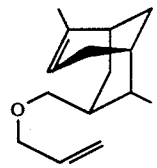

prepared according to Example VI.

Figure 20:

FIG. 20 is the GLC profile for the reaction product of Example VII containing the compound having the structure:

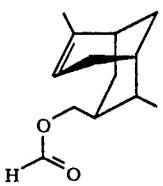

(Conditions: Carbowax column programmed at 130°-220° C. at 8° C. per minute).

FIG. 21 is the NMR spectrum for the compound having the structure:

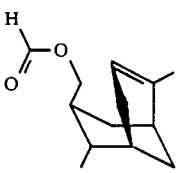

prepared according to Example VII.

FIGS. 21A, 21B, 21C and 21D are enlargements, respectively, of sections "A", "B", "C" and "D" of the NMR spectrum of FIG. 21.

FIG. 22 is the infrared spectrum for the compound having the structure:

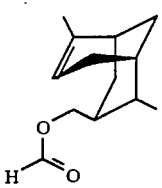

prepared according to Example VII.

Figure 23:
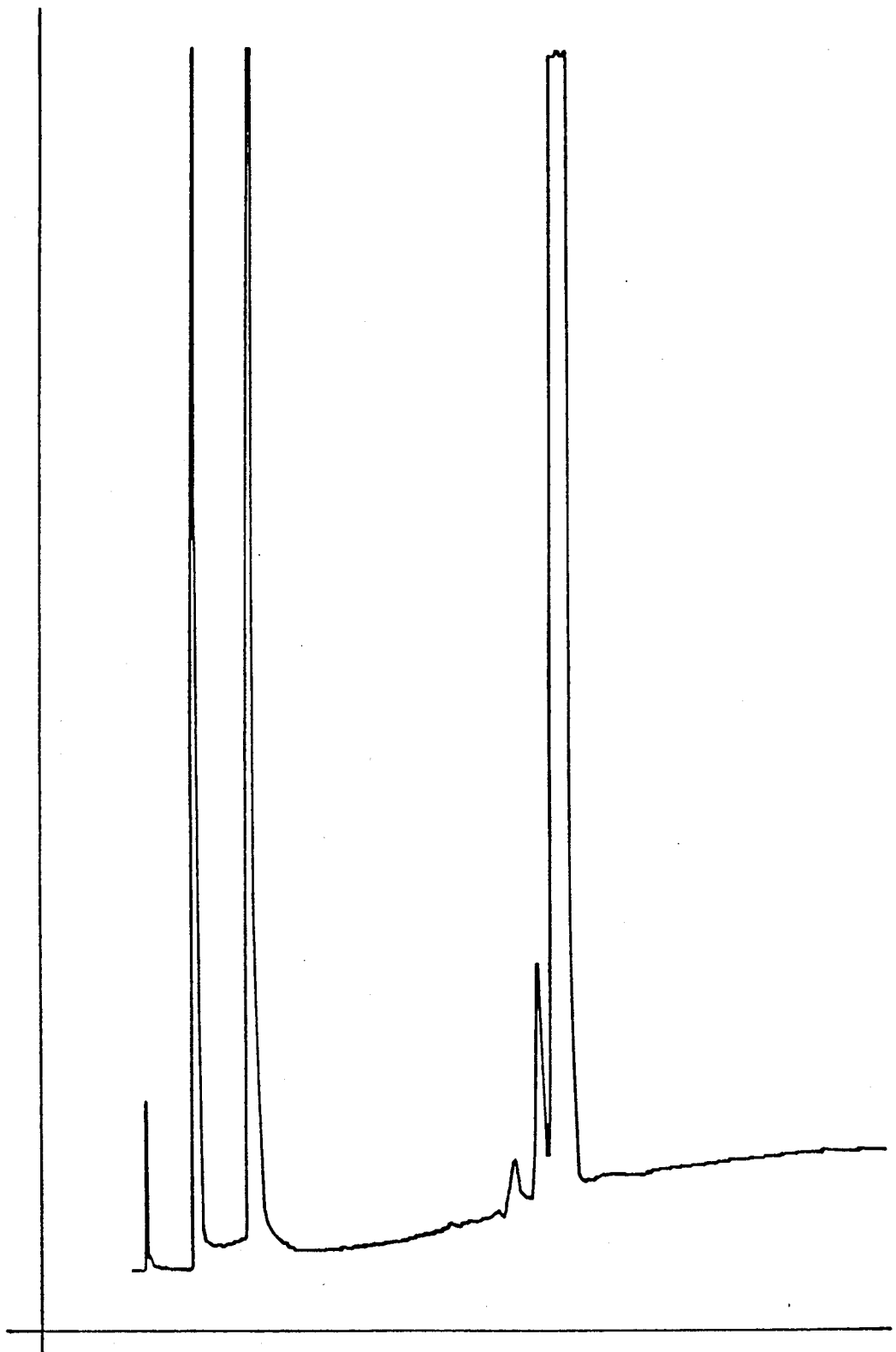

FIG. 23 is the GLC profile for the reaction product of Example VIII containing the compound having the structure:

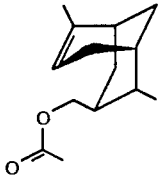

(Conditions: Carbowax column programmed at 130°-220° C. at 8° C. per minute).

FIG. 24 is the NMR spectrum for the compound having the structure:

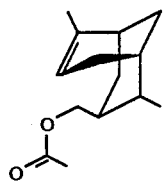

prepared according to Example VIII.

FIGS. 24A, 24B, and 24C are enlargements, respectively, of sections "A", "B" and "C" of the NMR spectrum of FIG. 24.

Figure 25:
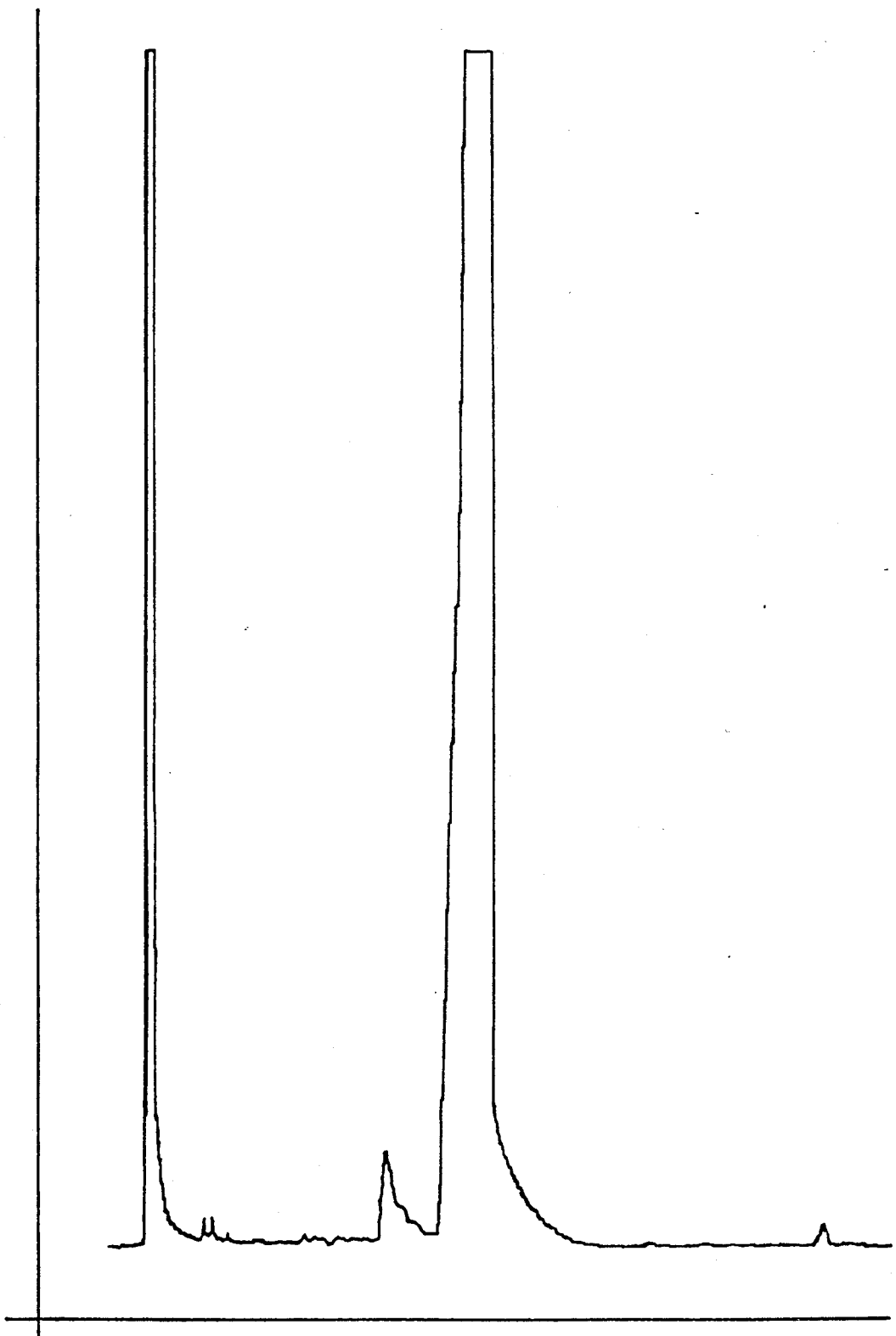

FIG. 25 is the GLC profile for the reaction product of Example IX containing the compound having the structure:

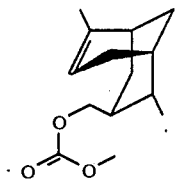

FIG. 26 is the NMR spectrum for the compound having the structure:

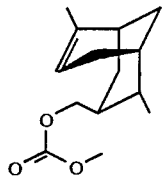

prepared according to Example IX.

FIGS. 26A, 26B and 26C are enlargements, respectively, of sections "A", "B" and "C" of the NMR spectrum of FIG. 26.

FIG. 27 is the infrared spectrum for the compound having the structure:

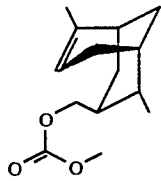

prepared according to Example IX.

Figure 28:
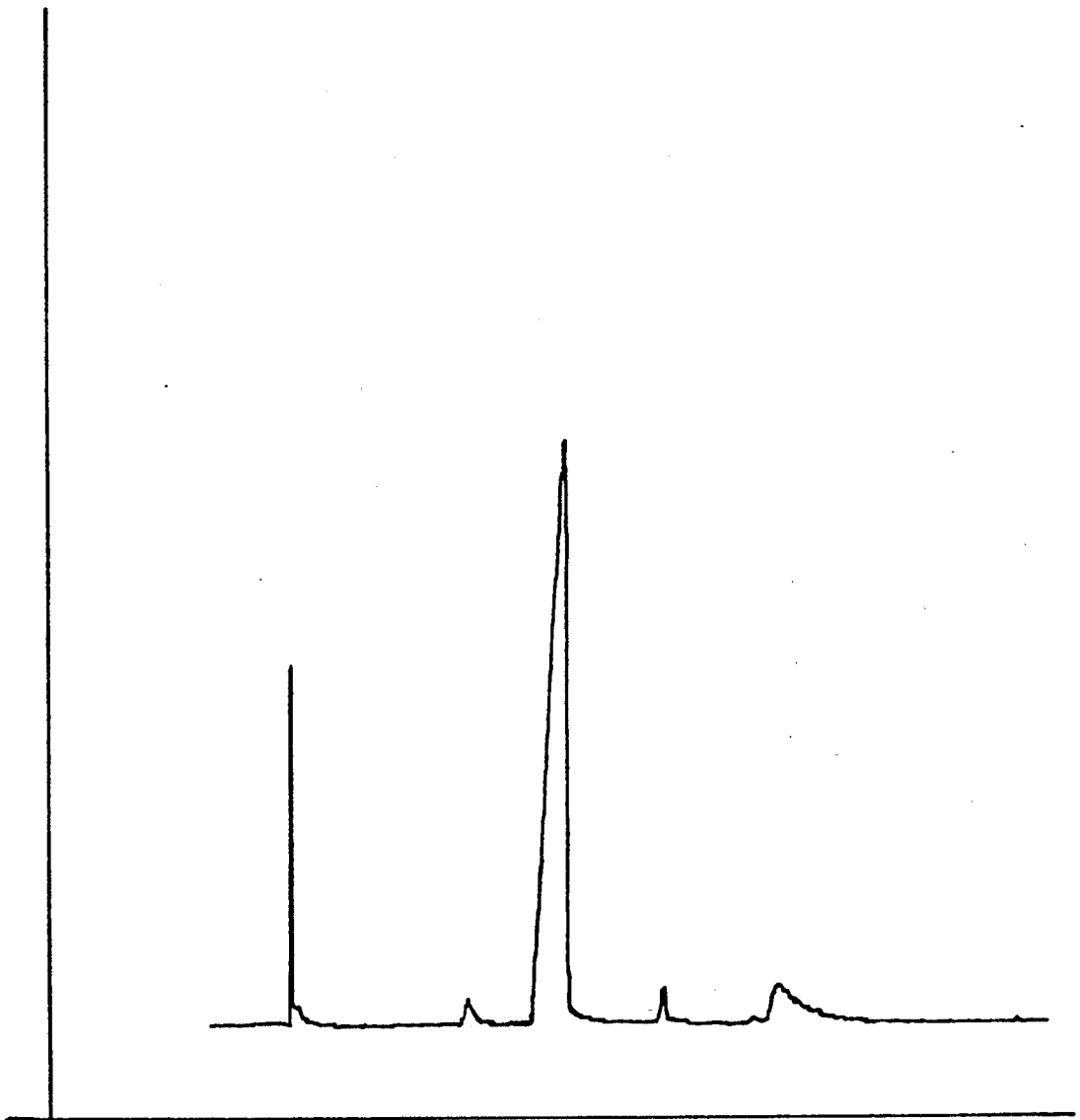

FIG. 28 is the GLC profile for the reaction product of Example X containing the compound having the structure:

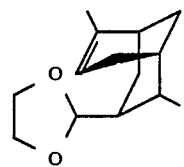

FIG. 29 is the NMR spectrum for the compound having the structure:

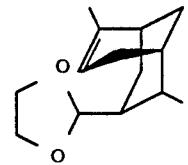

prepared according to Example X.

FIGS. 29A, 29B and 29C are, respectively, enlargements of sections "A", "B" and "C" of the NMR spectrum of FIG. 29.

FIG. 30 is the infrared spectrum for the compound having the structure:

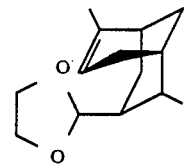

prepared according to Example X.

FIG. 31 is a partial side elevation and partial sectional view of an apparatus for forming polymer pellets containing at least one of the 2,6-dimethylbicyclo[3.3.1]non-6-ene-3-methanol and substituted derivatives thereof of our invention.

FIG. 32 is a section taken along line 32—32 of FIG. 31.

DETAILED DESCRIPTION OF THE DRAWINGS

Figure 1:
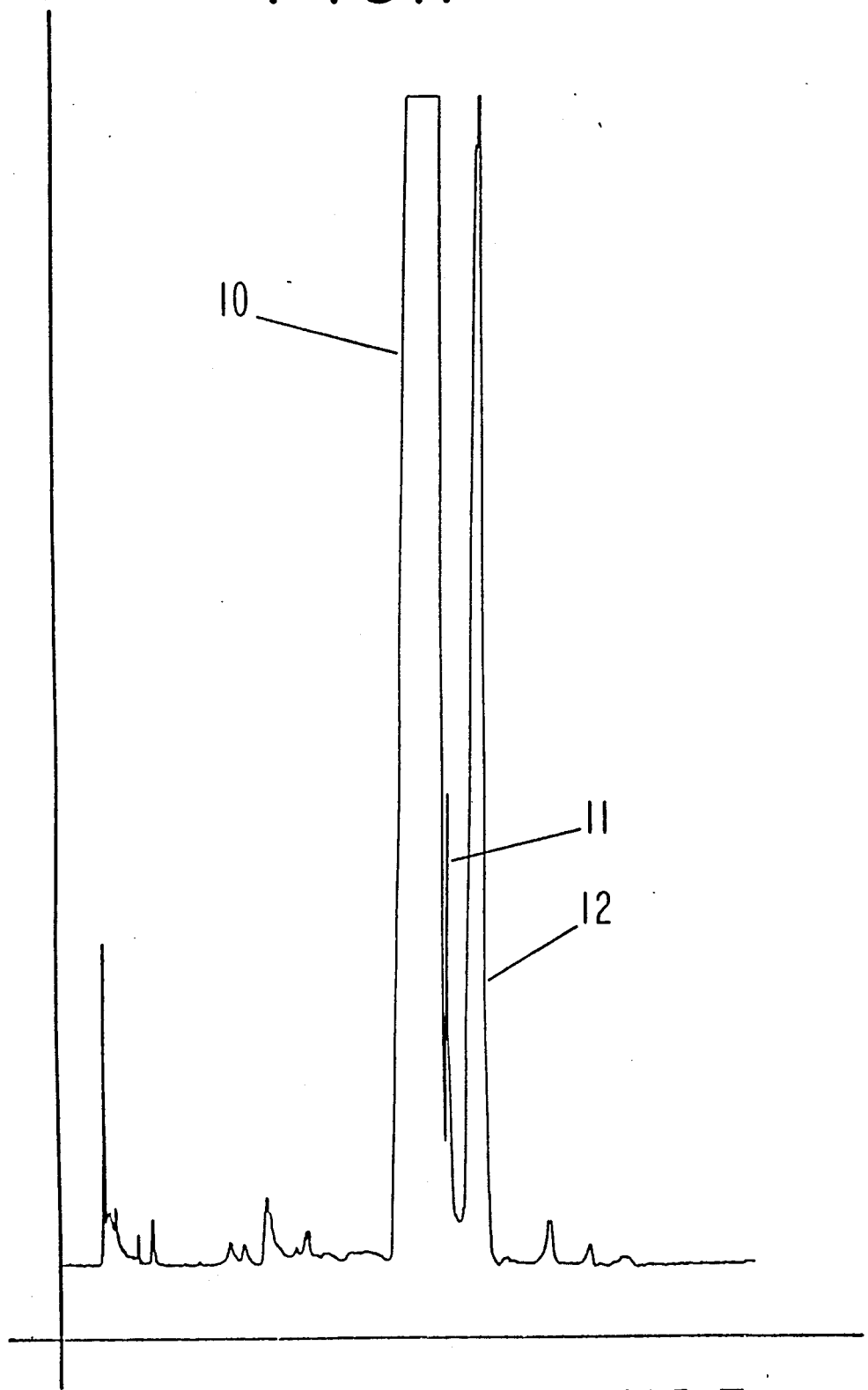

FIG. 1 is the GLC profile for the starting material for Example I. Each of peaks 10, 11 and 12 set forth various isomers of the starting material having the structure:

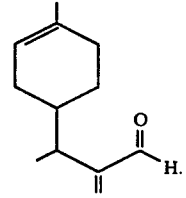

FIG. 2 is the GLC profile for the reaction product of Example I. The peaks indicated by reference numerals 20 and 21 are peaks for isomers of the reaction product having the structure:

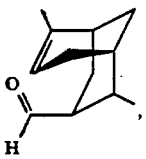

for example, the isomers having the structures:

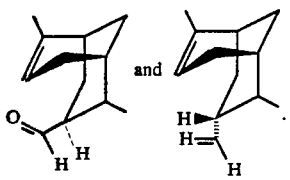

The peak indicated by reference numeral 22 is the peak for the side product of the reaction of Example I having the structure:

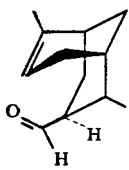

FIG. 11 is the GLC profile for the reaction product of Example IV. The peaks indicated by reference numeral 110 are for isomers of the compound having the structure:

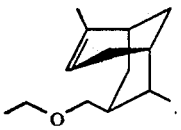

The peaks indicated by reference numerals 112 and 114 are for isomers of the compound having the structure:

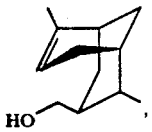

the starting material. (Conditions: Carbowax column programmed at 140° C. isothermal).

Referring to FIGS. 31 and 32 in particular, the apparatus used in producing polymeric fragrances containing one or more of the 2,6-dimethylbicyclo[3.3.13]non-6-ene-3-methanol and substituted derivatives thereof of our invention comprises a device for forming scented polyolefin (for example) pellets, which comprises a vat or container 212 into which a mixture of polyolefin such as polyethylene and an aromatic substance or scented material is placed (in this case at least one of the 2,6-dimethylbicyclo[3.3.1]non-6-ene-3-methanol and substituted derivatives thereof of our invention). The container is closed by an airtight lid 228 and clamped to the container by bolts 265. A stirrer 273 traverses the lid or cover 228 in airtight manner and is rotated in a suitable manner. A surrounding cylinder 212 having heating coils 212 A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless odorless polymer (e.g., polyethylene) with viscosity ranging between 180 and 220 saybolt seconds and having a melting point in the range of 200°-280° F. The heater 212A is operated to maintain the upper portion of the container 212 within a temperature range of from 250°-350° F. The bottom portion of the container is heated by means of heating coils 212A heated through a control 220 connected thereto through a connecting wire 222 to maintain the lower portion of the container within a temperature range of from 250°-350° F.

Thus, polymer (e.g., polyethylene) is added to container 212 and is heated from 10-12 hours whereafter a scented aroma-imparting material (at least one of the 2,6-dimethylbicyclo[3.3.1]non-6-ene-3-methanol and substituted derivatives thereof of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally about 5-30% by weight of the scented material (containing at least one of the 2,6-dimethylbicyclo[3.3.1]non-6-ene-3-methanol and substituted derivatives thereof of our invention) are added to the polyolefin.

After the scent imparting material (e.g., a composition containing at least one of the 2,6-dimethylbicyclo[3.3.1]-non-6-ene-3-methanol and substituted derivatives thereof of our invention) is added to the container 212, the mixture is stirred for a few minutes, for example, 5-15 minutes and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., at least one of the 2,6-dimethylbicyclo[3.3.1]non-6-ene-3-methanol and substituted derivatives thereof of our invention) will continuously drop through orifices 234 downwardly from conduit 232. During this time the temperature of the polymer (e.g., polyethylene or polyolefin) and scent imparting material (e.g., at least one of the 2,6-dimethylbicyclo[3.3.1]non-6-ene-3-methanol and substituted derivatives thereof of our invention) is accurately controlled so that a temperature in the range of from about 210°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the 2,6-dimethylbicyclo[3.3.1]non-6-ene-3-methanol and substituted derivatives thereof of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and which are utilized in processes as illustrated, infra.

A feature of this aspect of the process of our invention is the provision for moistening of the conveyor belt 238 to insure rapid formation of the solid polymeric (e.g., polyolefin) scented pellets 244 without sticking to material which will not normally stick to a melted plastic. A moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

The resulting product can be formulated into deodorized or scented products such as garbage bags and the like.

THE INVENTION

Our invention concerns 2,6-dimethylbicyclo[3.3.1]-non-6-ene-3-methanol and substituted derivatives thereof defined according to the generic structure:

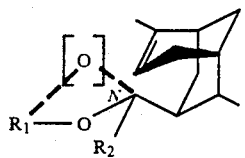

wherein each of the dashed lines represents a carbon-oxygen covalent bond or no bond; N is 0 or 1; $R_1$ represents hydrogen, $C_1-C_2$ lower alkyl; lower alkenyl; lower alkylenyl; $C_1-C_2$ acyl; alkoxycarbonyl; magnesium halo; or lithium and wherein $R_2$ represents methyl or hydrogen with the provisos that:

(i) when N is 1, each of the dashed lines represent carbon-oxygen covalent bonds, $R_2$ is hydrogen and $R_1$ is only lower alkylenyl; and when N is 0, the dashed lines are no covalent bonds and $R_1$ is no lower alkylenyl.

Furthermore, our invention covers uses of the compounds defined according to the generic structure:

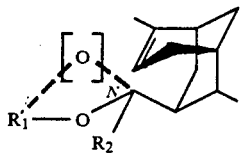

wherein the dashed lines, N, and $R_2$ are defined as above and where $R_1'$ represents hydrogen, $C_1-C_2$ lower alkyl, lower alkenyl, lower alkylenyl, $C_1-C_2$ acyl, and alkoxycarbonyl in augmenting or enhancing or imparting an aroma in or to consumable materials including including perfume compositions, perfumed articles (e.g., solid or liquid anionic, cationic, nonionic or zwitterionic detergents, fabric softeners, fabric softener articles, cosmetic powders, hair preparations and perfumed articles) colognes, deodorizing articles and compositions and malodor maskants.

Our invention also relates to processes for preparing such 2,6-dimethylbicyclo[3.3.1]non-6-ene-3-methanol and substituted derivatives thereof using as a starting material the substantially pure aldehyde defined according to the structure:

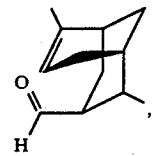

This substantially pure aldehyde may be produced according to the procedure set forth in Example I, infra, from the material having the structure:

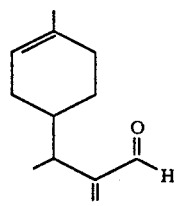

according to the reaction:

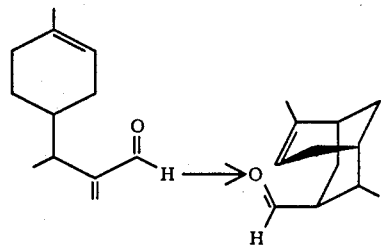

which involves the reaction mechanism:

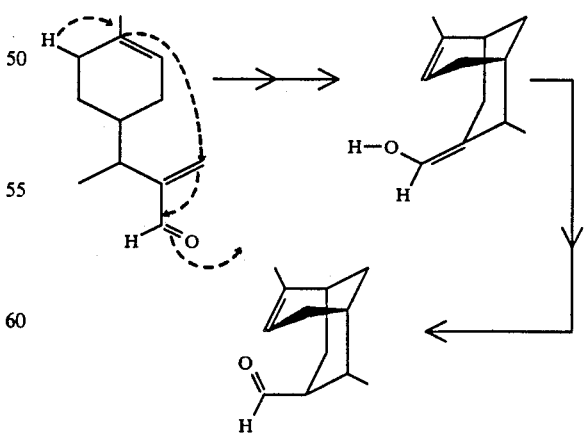

This reaction takes place at temperatures in the range of from 180° C. up to 220° C. in the absence of any additional catalyst or in the presence of the catalyst, ALAMINE® 336 (trademark of the Henkel Company of Minneapolis, Minn.). ALAMINE® 336 is a mixture of tri-$C_8$–$C_{10}$ alkyl amines and has a CAS Registery No. of 68814-95-9. It is also known as ADOGEN® 364 (trademark of Ashland Company). Its use has been previously published in U.S. Pat. No. 4,148,815 issued on Apr. 10, 1979 the disclosure for which is incorporated herein by reference.

The compound having the structure:

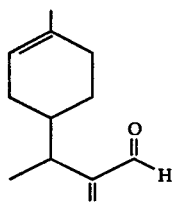

is prepared according to the reaction:

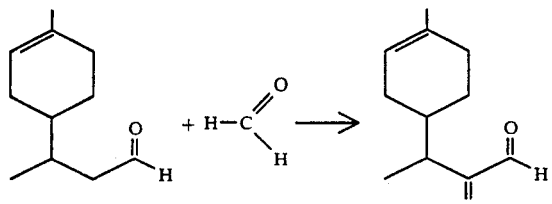

the preparation for which is exemplified in Examples I and II of U.S. Pat. No. 4,956,481 issued on Sept. 11, 1990, the specification for which is incorporated herein by reference.

Using the compound having the structure:

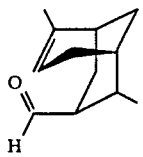

as a starting material, the 2,6-dimethylbicyclo[3.3.1]-non-6-ene-3-methanol and substituted derivatives thereof of our invention are prepared firstly by forming the compound having the structure:

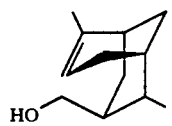

or forming the compound having the structure:

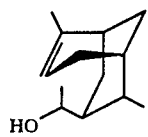

The compound having the structure:

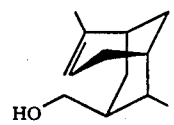

is prepared by reducing the compound having the structure:

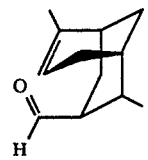

with an appropriate reducing agent such as sodium borohydride or lithium alumminum hydride according to the reaction:

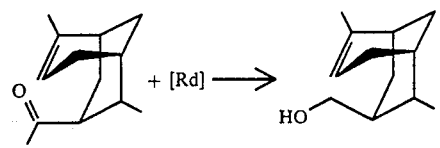

or more specifically according to the reaction:

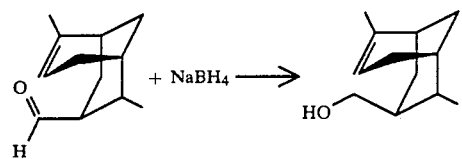

The mole ratio of reducing agent:compound having the structure:

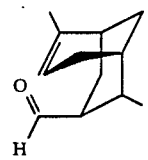

is preferably about 0.5:1.0. The temperature of reaction is preferably between about 10° C. and about 25° C. The reaction preferably takes place in the presence of an inert solvent such as isopropyl alcohol.

Compounds defined according to the structure:

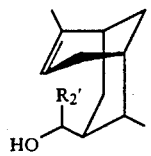

wherein $R_2'$ represent lower alkyl such as ethyl and methyl are prepared by reacting the compound having the structure:

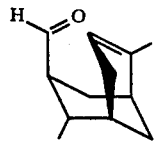

with an organometallic compound R₂'M according to the reaction:

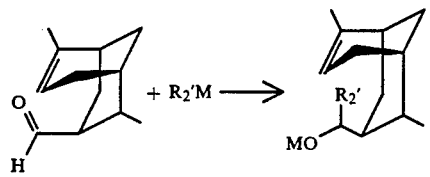

to produce the compound having the structure:

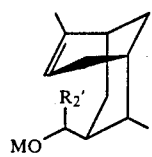

and then hydrolyzing the compound having the structure:

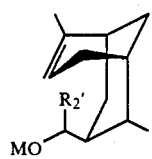

in the presence of a weak acid such as ammonium chloride or dilute hydrochloric acid according to the reaction:

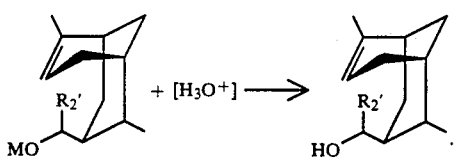

With the above reaction sequence, M represents lithium or magnesium halo such as magnesium chloro or magnesium bromo. Thus, more specifically, methyl lithium can be reacted with the compound having the structure:

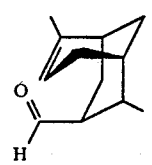

according to the reaction:

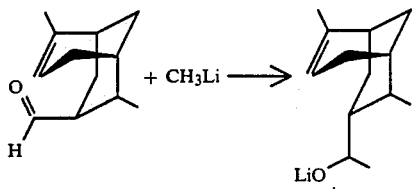

to produce the organolithium derivative having the structure:

or methyl magnesium halide such as methyl magnesium chloride or methyl magnesium bromide may be reacted with the compound having the structure:

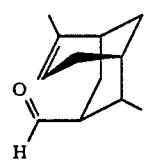

to produce the compound having the structure:

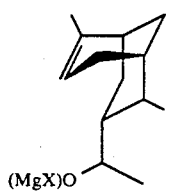

wherein X is chloro or bromo. The resulting product is then hydrolyzed, for example, the compound having the structure:

is hydroyzed using dilute hydrochloric acid or aqueous ammonium chloride according to the reaction:

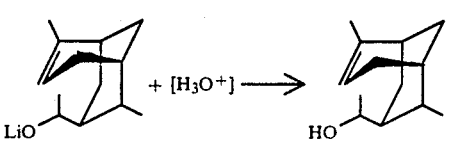

in order to produce the compound having the structure:

The compound having the structure:

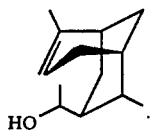

can also be reacted to form ethers defined according to the structure:

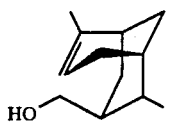

wherein R" is $C_1-C_2$ alkyl or alkenyl such as allyl. The reaction to form such ethers may be carried out using an alkyl or alkenyl halide and an alkali metal hydride according to the reaction:

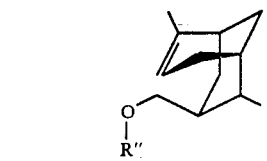

wherein X" is chloro, bromo or iodo and M" is alkali metal such as sodium or potassium. Such reactions may be exemplified as follows:

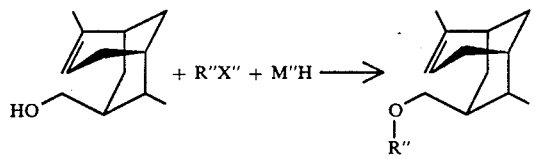

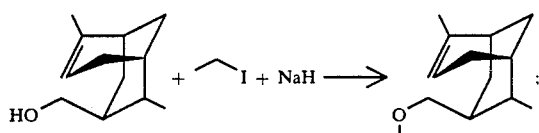

and

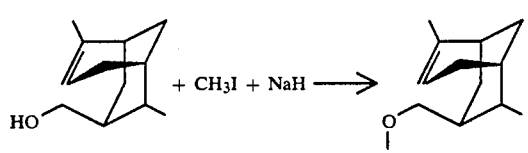

Furthermore, the compound having the structure:

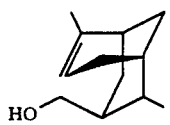

may be reacted with an acylating agent or an alkoxy acylating agent defined according to the generic structure:

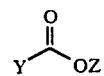

in order to form a compound having the generic structure:

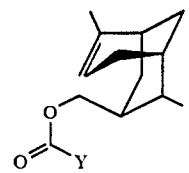

according to the reaction:

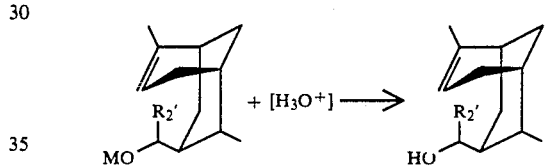

wherein Y represents hydrogen, alkyl or alkoxy and wherein z represents hydrogen, acyl or alkoxycarbonyl. Examples of such reactons are as follows:

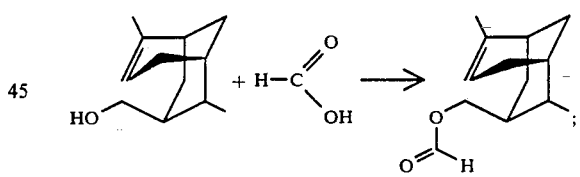

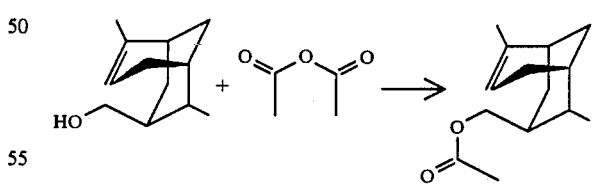

and

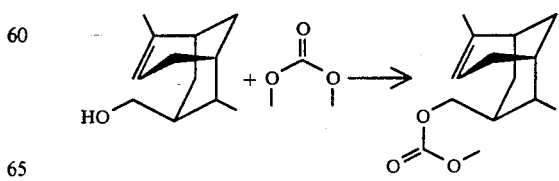

Furthermore, acetals may be produced from the compound having the structure:

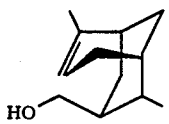

by reaction thereof with alcohols and diols, for example, according to the reaction:

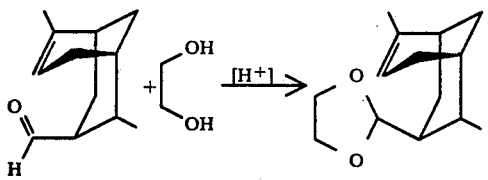

wherein the compound having the structure:

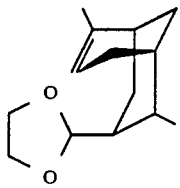

is produced.

At the end of each of the foregoing reactions the reaction mass may be appropriately "worked up", whereby the reaction mass is neutralized, the solvent evaporated and the reaction product distilled as by fractional distillation. The resulting products may be used "as is" or they may be further reacted as shown, supra.

The 2,6-dimethylbicyclo[3.3.1]non-6-ene-3-methanol and substituted derivatives thereof of our invention have intense and substantive aromas which can be described as green, early morning forest path, sandalwood, piney, camphoraceous, geranium, rhodinol, peppery, woody, orris, orivone, sweet and grapefruit-like with natural piney, green, woody, pine and needle, sappy, camphoraceous, rhodinol, peppery and orivone topnotes and "cooling" undertones. Table I, below, sets forth the summary of the particular compounds exemplified in our invention and their aromas.

TABLE I

| Composition of Matter | Perfumery Properties |
|---|---|
| The compound having the structure:<br />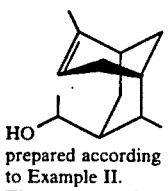<br />prepared according to Example II. | A green, early morning forest path aroma. |
| The compound having the structure:<br />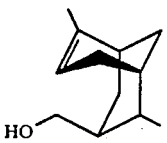 | A sandlewood, green, piney, camphoraceous aroma with natural piney, green, woody, sappy, camphoraceous topnotes. |

TABLE I-continued

| Composition of Matter | Perfumery Properties |
|---|---|
| prepared according to Example III. The compound having the structure: | A woody, piney aroma with woody, pine needle topnotes. |
| prepared according to Example V. The compound having the structure: | A geranium, rhodinol, peppery, woody aroma with rhodinol and peppery topnotes and "cooling" undertones. |
| prepared according to Example VI. The compound having the structure: | An orris, orivone, green aroma with piney, camphoraceous, green, orivone topnotes. |
| prepared according to Example VII. The compound having the structure: | A woody, grapefruit-like, sweet aroma. |
| prepared according to Example VIII. The compound having the structure: | A floral aroma. |
| produced according to Example IX. | |

The 2,6-dimethylbicyclo[3.3.1]non-6-ene-3-methanol and substituted derivatives thereof of our invention can be used to contribute powerful long-lasting green, early morning forest path, sandalwood, piney, camphoraceous, geranium, rhodinol, peppery, woody, orris, orivone, sweet and grapefruit-like aromas with natural piney, green, woody, pine needle, sappy, camphoraceous, rhodinol, peppery and orivone topnotes and "cooling" undertones to perfume compositions, perfumed articles, colognes, deodorizing articles, deodorizing compositions and malodor maskants. Examples of perfumed articles are anionic, cationic, nonionic or zwitterionic detergents, drier-added fabric softener compositions and drier-added fabric softener articles as well as hair preparations. As olfactory agents, the 2,6-dimethylbicyclo[3.3.1]non-6-ene-3-methanol and substituted derivatives thereof of our invention can be fomulated into or used as components of a "perfume composition" or can be used as components of a "perfumed article" or the perfume composition may be added to perfumed articles.

The term "perfume composition" is used herein to mean a mixture of organic compounds including, for example, alcohols (other than the alcohols of our invention); aldehydes; ketones, nitriles, ethers (other than the ethers of our invention), lactones, esters (other than the esters of our invention) carbonates (other than the carbonates of our invention), natural essential oils, synthetic essential oils, and frequently hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, the individual component will contribute its particular olfactory characteristics, but the overall effect of the perfume composition will be the sum of the effects of each of the ingredients. Thus, the individual 2,6-dimethylbicyclo[3.3.1]non-6-ene-3-methanol and substituted derivatives thereof of our invention or mixtures thereof can be used to alter the aroma characteristics of a perfume composition, for example, by highlighting or moderating the olfactory reaction contributed by another ingredient in the composition.

The amount of one or more of the 2,6-dimethylbicyclo[3.3.1]-non-6-ene-3-methanol and substituted derivatives thereof of our invention which will be effective in perfume compositions, depends on many factors including the other ingredients, their amounts, and the effects which are desired. It has been found that perfume compositions containing as little as 0.5% of one or more of the 2,6-dimethylbicyclo[3.3.1]non-6-ene-3-methanol and substituted derivatives thereof of our invention or even less can be used to impart interesting, substantive and intense green, early morning forest path, sandalwood, piney, camphoraceus, geranium, rhodinol, peppery, woody, orris, orivone, sweet and grapefruit-like aromas with natural piney, green, woody, pine needle, sappy, camphoraceous, rhodinol, peppery and orivone topnotes and "cooling" undertones to soaps, liquid and solid anionic, cationic, nonionic and zwitterionic detergents, cosmetic powders, liquid and solid fabric softeners, optical brightener compositions, perfumed polymers and other products. The amount employed can range up to 50% or higher and will depend on considerations of cost, nature of the end product and the effect desired on the finished product and the particular fragrance sought.

The 2,6-dimethylbicyclo[3.3.1]non-6-ene-3-methanol and substituted derivatives thereof of our invention can be used alone or in perfume compositions as olfactory components in detergents and soaps, space odorants and deodorants; colognes, toilet water, bath salts, hair preparations, such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 0.01% of one or more of the 2,6-dimethylbicyclo[3.3.1]-non-6-ene-3-methanol and substituted derivatives thereof of our invention will suffice to impart interesting, long-lasting and intense green, early morning forest path, sandalwood, piney, camphoraceous, geranium, rhodinol, peppery, woody, orris, orivone, sweet and grapefruit-like aromas with natural piney, green, woody, pine needle, sappy, camphoraceous, rhodinol, peppery and orivone topnotes and "cooling" undertones. Generally, no more than 0.5% is required.

In addition, the perfume composition can contain a vehicle or carrier for the 2,6-dimethylbicyclo[3.3.1]non-6-ene-3methanol and substituted derivatives thereof of our invention taken alone or taken together with other ingredients. The vehicle can be a liquid such as an alcohol such as ethanol, a glycol such as propylene glycol or the like. The carrier can be an absorbent solid such as gum (e.g., gum arabic, guar gum and xanthan gum) or components for encapsulating the composition such as gelatin which can be used to form a capsule wall surrounding the perfume oil as by means of coacervation.

The following Example I sets forth the preparation of the precursor of the 2,6-dimethylbicyclo[3.3.1]non-6-ene-3-methanol and substituted derivatives thereof of our invention having the structure:

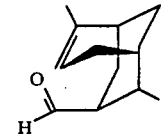

Examples II-X set forth preparation of the 2,6-dimethylbicyclo[3.3.1]non-6-ene-3-methanol and substituted derivatives thereof of our invention. Examples XI, et seq. set forth the organoleptic uses of the 2,6-dimethylbicyclo[3.3.1]non-6-ene-3-methanol and substituted derivatives thereof of our invention prepared according to Examples II-X.

All parts and percentages given herein are by weight unless otherwise specified.

EXAMPLE I

Preparation of 2,6-Dimethylbicyclo[3.3.1]non-6-ene-3-Carboxaldehyde

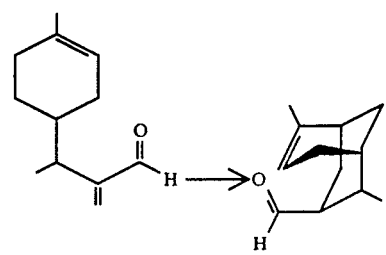

Into a 200 cc reaction vessel equipped with stirrer, thermometer and reflux condenser is placed 100 grams (0.5 moles) of the compound having the structure:

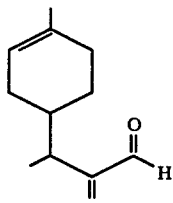

prepared in accordance with Example II of U.S. Pat. 4,956,481 issued on Sept. 11, 1990.

The reaction mass is heated to 185° C. and maintained with stirring at 183°-190° C. for a period of four hours. At the end of the reaction, the reaction mass is fractionally distilled yielding the following fractions:

| Fraction No. | Vapor Temp. (°C.) | Liquid Temp. (°C.) | Vacuum mm/Hg. Pressure |
| --- | --- | --- | --- |
| 1 | 33/40 | 78/125 | 9.5/8.77 |
| 2 | 146 | 157 | 3.10 |
| 3 | 98 | 119 | 2.32 |
| 4 | 106 | 124 | 1.87 |
| 5 | 103 | 200 | 1.69. |

Fraction 4 is substantially pure product having the structure:

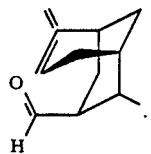

FIG. 3 is the NMR spectrum and FIG. 4 is the IR spectrum for the compound having the structure:

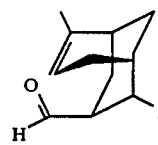

The compound having the structure:

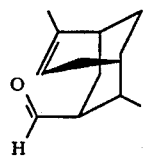

is used in further reactions as set forth in Examples II-X, infra.

EXAMPLE II

Preparation of Alpha,2,6-Trimethyl Bicyclo[3.3.1]non-6-ene-3-Methanol

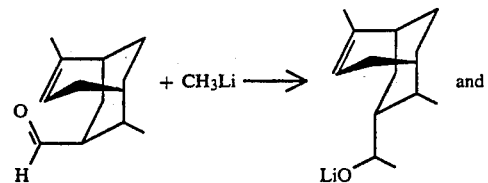

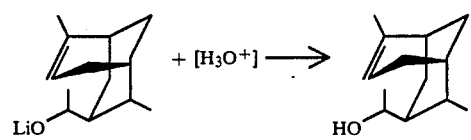

Into a 5 liter reaction vessel equipped with stirrer, thermometer, reflux condenser and addition funnel is placed 1600 ml (1.4 molar) of methyl lithium in diethyl ether (2.24 moles). The methyl lithium solution is cooled to 0° C. While maintaining the reaction mass at a temperature of −2° C. up to 0° C. 288 grams (1.53 moles) of the compound having the structure:

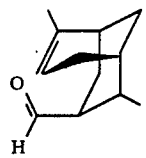

prepared according to Example I is added to the methyl lithium solution over a period of one hour (with stirring). The reaction mass is then maintained at 0°-2° C. with stirring for a period of two hours.

The organic phase is then separated from the aqueous phase and the organic phase is evaporated and then fractionally distilled yielding the following fractions:

| Fraction No. | Vapor Temp. (°C.) | Liquid Temp. (°C.) | Vacuum mm/Hg. Pressure |
| --- | --- | --- | --- |
| 1 | 9/100 | 24/110 | 6.2/1.9 |
| 2 | 109 | 125 | 1.87 |
| 3 | 32 | 179 | 1.83. |

NMR, IR and mass spectral analysis yield the information that the resulting compound has the structure:

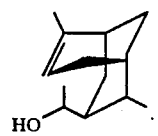

The resulting compound has a green, early morning forest path aroma. (Distillation Fractions 2 and 3). FIG. 6 is the NMR spectrum and FIG. 7 is the infrared spectrum for the compound having the structure:

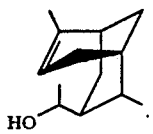

EXAMPLE III

Preparation of 2,6-Dimethyl Bicyclo[3.3.1]non-6-ene-3-Methanol

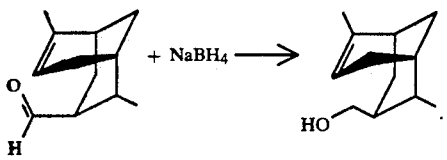

Into a 5 liter reaction vessel equipped with stirrer, thermometer, reflux condenser and nitrogen blanket apparatus are placed 63.0 grams of sodium borohydride; 800 ml isopropyl alcohol and 700 ml water. The resulting mixture is cooled to 15°–20° C.

Over a period of 1.5 hours, while maintaining the reaction mass at 14°–18° C., 600.0 grams of the compound having the structure:

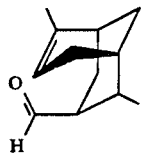

prepared according to Example I is added to the reaction mass with stirring. The reaction mass is then maintained at 17°–18° C. for a period of 0.5 hours.

While maintaining the reaction mass at 17°–18° C. over a period of one hour, 600 cc of 10% acetic acid is added to the reaction mass. Over a period of 0.5 hours, 500 cc of toluene is then added to the reaction mass with stirring. The reaction mass is then stirred for an additional 0.5 hours. The organic phase is separated from the aqueous phase and the organic phase is washed as follows:

1–600 cc volume of 10% acetic acid;
1–5% volume of aqueous sodium bicarbonate solution; and
1–600 cc volume of water.

The reaction mass is then dried over anhydrous magnesium sulfate and distilled yielding the following fractions:

| Fraction No. | Vapor Temp. (°C.) | Liquid Temp. (°C.) | Vacuum mm/Hg. Pressure |
|---|---|---|---|
| 1 | 135/132 | 150/152 | 7.90/9.28 |
| 2 | 147 | 153 | 23.0 |
| 3 | 150 | 154 | 23.7 |
| 4 | 151 | 155 | 24.0 |
| 5 | 151 | 155 | 24.8 |
| 6 | 153 | 158 | 24.8 |
| 7 | 153 | 158 | 24.5 |
| 8 | 153 | 158 | 24.7 |
| 9 | 153 | 158 | 24.5 |
| 10 | 153 | 158 | 24.5 |

-continued

| Fraction No. | Vapor Temp. (°C.) | Liquid Temp. (°C.) | Vacuum mm/Hg. Pressure |
|---|---|---|---|
| 11 | 154 | 157 | 25.0 |
| 12 | 155 | 158 | 25.0 |
| 13 | 155 | 158 | 25.0 |
| 14 | 155 | 158 | 25.0 |
| 15 | 155 | 158 | 25.5 |
| 16 | 153 | 158 | 25.0 |
| 17 | 154 | 185 | 26.0. |

Fractions 1-14, 17 and 18 are bulked. The resulting product as shown by NMR, IR and mass spectral analysis has the structure:

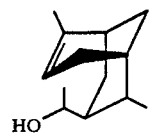

The compound having the structure:

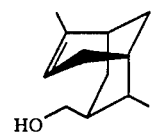

has a sandalwood, green, piney and camphoraceous aroma with natural piney, green, woody, sappy and camphoraceous topnotes.

FIG. 9 is the NMR spectrum and FIG. 10 is the infrared spectrum for the compound having the structure:

EXAMPLE IV

Preparation of 7-(Ethoxymethyl)-2,6-Dimethylbicyclo[3.3.1]non-2-ene

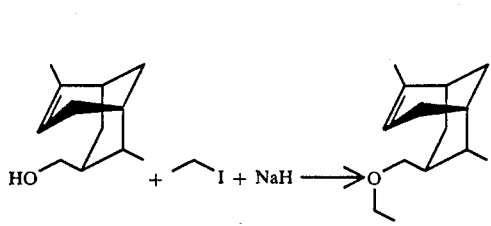

Into a 3 liter reaction vessel equipped with stirrer, thermometer, reflux condenser and heating mantle are charged 78 grams (1.3 moles) of sodium hydride and 375 ml of anhydrous tetrahydrofuran. While maintaining the reaction mass at 28°–40° C., over a period of 0.5 hours, 362 grams (2 moles) of the compound having the structure:

prepared according to Example III is added to the reaction mass. The reaction mass is then heated to reflux (66°-68° C.) and refluxed for a period of 1.5 hours.

While maintaining the reaction mass at 66°-68° C., over a period of two hours, 374 grams (1.2 moles) of ethyl iodied is added to the reaction mass.

The reaction mass is then maintained at 66°-68° C. for a period of 2.5 hours.

The reaction is then quenched with 500 ml water. The reaction mass is then washed with three portions (500 ml each) of water.

The reaction mass is then dried over anhydrous magnesium sulfate and filtered. The resulting product is then fractionally distilled yeilding the following fractions:

| Fraction No. | Vapor Temp. (°C.) | Liquid Temp. (°C.) | Vacuum mm/Hg. Pressure |
| --- | --- | --- | --- |
| 1 | 28/27 | 43/73 | 3.5/3.5 |
| 2 | 98 | 116 | 2.43 |
| 3 | 98 | 116 | 2.87 |
| 4 | 98 | 117 | 2.85 |
| 5 | 110 | 118 | 2.93 |
| 6 | 103 | 119 | 2.90 |
| 7 |  | 120 | 2.89 |
| 8 | 108 | 121 | 2.96 |
| 9 | 108 | 112 | 3.16 |
| 10 | 103 | 128 | 3.01 |
| 11 | 100 | 100 | 2.91. |

Fractions 4-8 are bulked.

The resulting product has the structure:

as confirmed by NMR, IR and mass spectral analysis.

FIG. 12 is the NMR spectrum and FIG. 13 is the infrared spectrum for the compound having the structure:

EXAMPLE V

Preparation of 7-(Methoxymethyl)-2,6-Dimethylbicyclo[3.3.1]non-2-ene

Into a 2 liter reaction vessel equipped with stirrer, thermometer and reflux condenser are placed 39 grams (1.3 moles) of sodium hydride and 200 ml anhydrous tetrahydrofuran. The reaction vessel is cooled to 24° C. and over a period of ten minutes while maintaining the reaction mass at 24°-26° C., 181 grams (1 mole) of the compound having the structure:

prepared according to Example III is added to the reaction mass.

The reaction mass is then heated to reflux and maintained at reflux for a period of 1.5 hours (69° C.).

While maintaining the reaction mass at 69°-72° C., over a period of one hour, 170 grams (1.2 moles) of methyl iodide is added to the reaction mass.

The reaction mass is then maintained with stirring at 70°-72° C. for a period of two hours. At the end of the two hour period, the reaction mass is cooled to room temperature and quenched with 200 ml of 10% aqueous hydrochloric acid.

The aqueous phase is separated from the organic phase and the aqueous phase is dried wih anhydrous magnesium sulfate and filtered. The resulting product is then fractionally distilled yielding the following fractions:

| Fraction No. | Vapor Temp. (°C.) | Liquid Temp. (°C.) | Vacuum mm/Hg. Pressure |
| --- | --- | --- | --- |
| 1 | 38/37 | 61/73 | 12.0/9.68 |
| 2 | 85 | 97 | 4.25 |
| 3 | 87 | 115 | 4.30 |
| 4 | 90 | 143 | 4.30 |
| 5 | 83 | 141 | 2.66. |

NMR, IR and mass spectral analysis confirm the structure of the resulting product as:

Bulked distillation Fractions 3-5 have a woody, piney aroma with woody and pine needle topnotes.

FIG. 15 is the NMR spectrum and FIG. 16 is the IR spectrum for the compound having the structure:

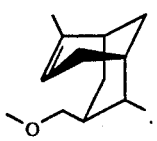

EXAMPLE VI

Preparation of 7-[(Allyloxy)Methyl]2-6-Dimethyl Bicyclo[3.3.1]non-2-ene

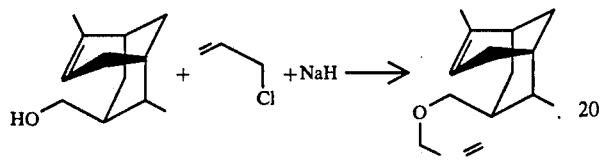

Into a 3 liter reaction vessel equipped with stirrer, thermometer, reflux condenser and heating mantle are placed 90 grams (1.5 moles) of sodium hydride and 400 ml anhydrous tetrhydrofuran.

The reaction mass is cooled to 25° C. and while maintaining the reaction mass at 25°-34° C. over a period of five minutes, 362 grams (2 moles) of the compound having the structure:

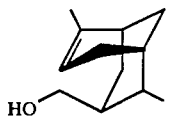

produced according to Example III is added to the reaction mass.

The reaction mass is then heated to reflux (67°-68° C.) and maintained at reflux for a period of one hour. At the end of the one hour period, over a period of one hour while maintaining the reaction mass at 67°-68° C., 200 grams (2.6 moles) of allylchloride is added to the reaction mass.

The reaction mass is then maintained at 68° C. for a period of three hours.

At the end of the three hour period the reaction mass is quenched with two 1000 ml volumes of water.

The organic phase is then separated from the aqueous phase and the organic phase is dried over anhydrous magnesium sulfate and filtered. The resulting organic phase is then fractionally distilled yielding the following fractions:

| Fraction No. | Vapor Temp. (°C.) | Liquid Temp. (°C.) | Vacuum mm/Hg. Pressure |
| --- | --- | --- | --- |
| 1 | 29/26 | 52/71 | 1.70/7.63 |
| 2 | 105 | 118 | 2.10 |
| 3 | 112 | 122 | 2.06 |
| 4 | 118 | 125 | 2.14 |
| 5 | 115 | 125 | 2.13 |
| 6 | 112 | 125 | 2.14 |
| 7 | 114 | 120 | 2.07 |
| 8 | 111 | 121 | 2.05 |
| 9 | 113 | 119 | 2.02 |
| 10 | 110 | 118 | 2.00 |

-continued

| Fraction No. | Vapor Temp. (°C.) | Liquid Temp. (°C.) | Vacuum mm/Hg. Pressure |
| --- | --- | --- | --- |
| 11 | 108 | 118 | 1.99 |
| 12 | 108 | 119 | 1.99 |
| 13 | 108 | 119 | 1.97 |
| 14 | 108 | 121 | 1.96 |
| 15 | 108 | 122 | 1.95 |
| 16 | 106 | 134 | 1.53 |
| 17 | 75 | 144 | 1.92. |

Fractions 8-15 are bulked. Bulked distillation Fractions 8-15 have a geranium, rhodinol, peppery, woody aroma with rhodinol and peppery topnotes and "cooling" undertones.

The resulting product has the structure:

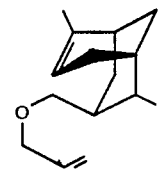

as confirmed by infrared, NMR and mass spectral analysis.

FIG. 18 is the NMR spectrum and FIG. 19 is the IR spectrum for the compound having the structure:

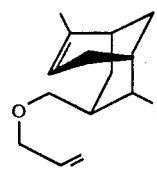

EXAMPLE VII

Preparation of 2,6-Dimethylbicyclo[3.3.1]non-6-ene-3-Methanol Formate

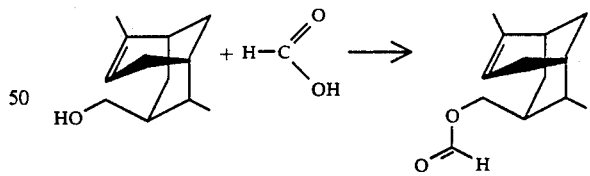

Into a 250 cc reaction vessel equipped with stirrer, thermometer and reflux condenser are placed 41.4 grams (0.81 moles) of formic acid and 84 grams (0.73 moles) of phosphoric acid. The reaction mass is then maintained at 27°-30° C. and over a period of 1.5 hours, 73 grams (0.41 moles) of the compound having the structure:

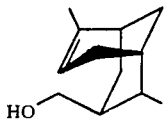

prepared according to Example III is added to the reaction mass.

The reaction mass is then heated to 60° C. and maintained at 60° C. for a period of two hours.

An additional 80 grams of formic acid and 160 grams of phosphoric acid is then added to the reaction mass. The reaction mass is then maintained at 60° C. for a period of three hours.

The organic phase is then separated from the aqueous phase and the aqueous phase is washed with toluene. The toluene extract and the organic phase are combined and the resulting product is then washed with aqueous 5% sodium bicarbonate until neutral.

The resulting product is then dried over anhydrous magnesium sulfate and fractionally distilled yielding the following fractions:

| Fraction No. | Vapor Temp. (°C.) | Liquid Temp. (°C.) | Vacuum mm/Hg. Pressure |
|---|---|---|---|
| 1 | 43/32 | 52/126 | 9.5/11.2 |
| 2 | 135 | 138 | 11.7 |
| 3 | 100 | 165 | 11.3. |

Fractions 2 and 3 are bulked.

The resulting product as confirmed by NMR, IR and mass spectral analysis has the structure:

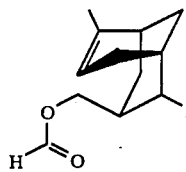

The resulting product (bulked distillation Fractions 2 and 3) has an orris, orivone, greed aroma with piney, camphoraceous, green and orivone topnotes.

FIG. 21 is the NMR spectrum and FIG. 22 is the infrared spectrum for the compound having the structure:

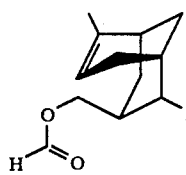

EXAMPLE VIII

Preparation of 2,6-Dimethyl Bicyclo[3.3.1]non-6-ene-3-Methanol Acetate

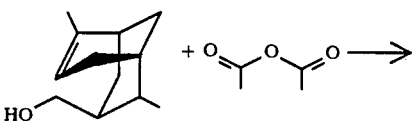

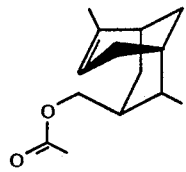

Into a 1 liter reaction vessel equipped with stirrer, thermometer and reflux condenser are placed 250 grams of the compound having the structure:

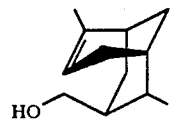

prepared according to Example III (1.39 moles) and 212 grams (2.8 moles) of acetic anhydride. The reaction mass is then heated to reflux with stirring and maintained at reflux (145° C.) for a period of one hour.

The reaction mass is then cooled to room temperature and washed with one liter volume of water. The aqueous phase is separated from the organic phase and the organic pase is dried over anhydrous magnesium sulfate and then fractionally distilled yielding the following fractions:

| Fraction No. | Vapor Temp. (°C.) | Liquid Temp. (°C.) | Vacuum mm/Hg. Pressure |
|---|---|---|---|
| 1 | 115/117 | 140/137 | 3.62/9.60 |
| 2 | 120 | 143 | 3.92 |
| 3 | 120 | 147 | 3.80 |
| 4 | 123 | 145 | 3.56 |
| 5 | 123 | 147 | 3.40 |
| 6 | 123 | 147 | 3.40 |
| 7 | 120 | 136 | 5.04 |
| 8 | 115 | 147 | 3.21 |
| 9 | 115 | 147 | 3.18 |
| 10 | 117 | 150 | 3.16. |

Fractions 3-7 are bulked.

Bulked distillation Fractions 3-7 have an intense and substantive woody, grapefruit-like and sweet aroma.

NMR, IR and mass spectral analysis confirm the fact that the resulting product has the structure:

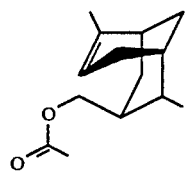

FIG. 24 is the NMR spectrum for the compound having the structure:

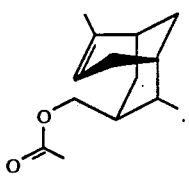

EXAMPLE IX

Preparation of the Methyl Ester of (2,6-Dimethybicyclo[3.3.1]non-6-en-3-yl)Methyl Carbonic Acid

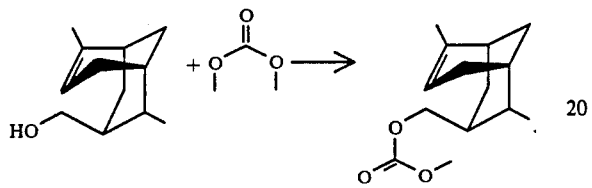

Into a 5 liter reaction vessel equipped with stirrer, thermometer, reflux condenser and heating mantle are placed 500 grams (2.76 moles) of the compound having the structure:

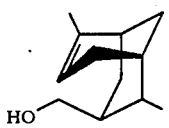

prepared according to Example III and 747 grams (8.29 moles) of dimethyl carbonate. While maintaining the reaction mass at 20°-26° C. over a period of 10 minutes, 60 grams (0.276 moles) of a 25% solution of sodium methoxide is added to the reaction mass.

The reaction mass is then heated to reflux (82° C.) and maintained at reflux for a period of ten minutes.

At the end of the ten minute period, the reaction mass is cooled to room temperature and 1000 ml of 10% aqueous acetic acid is added with stirring. Then 1000 ml of saturated sodium bicarbonate (aqueous) is added. The reaction mass is then washed with 1000 ml portions of saturated sodium chloride and water until neutral. The aqueous phase is separated from the organic phase. The organic phase is then dried with anhydrous magnesium sulfate and filtered. The resulting product is then fractionally distilled yielding the following fractions:

| Fraction No. | Vapor Temp. (°C.) | Liquid Temp. (°C.) | Vacuum mm/Hg. Pressure |
|---|---|---|---|
| 1 | 80/84 | 125/130 | .665/.615 |
| 2 | 85 | 130 | .597 |
| 3 | 92 | 130 | .585 |
| 4 | 96 | 132 | .650 |
| 5 | 94 | 130 | .573 |
| 6 | 94 | 130 | .570 |
| 7 | 94 | 130 | .565 |
| 8 | 96 | 138 | .606 |
| 9 | 97 | 138 | .630 |
| 10 | 97 | 145 | .573 |
| 11 | 96 | 145 | .580 |
| 12 | 96 | 140 | .577 |
| 13 | 96 | 140 | .576 |
| 14 | 96 | 190 | .622 |

-continued

| Fraction No. | Vapor Temp. (°C.) | Liquid Temp. (°C.) | Vacuum mm/Hg. Pressure |
|---|---|---|---|
| 15 | 90 | 205 | .610. |

Fractions 6-12 are bulked.

Bulked distillation Fractions 6-12 have an intense floral aroma.

The resulting product as confirmed by NMR, IR and mass spectral analysis has the structure:

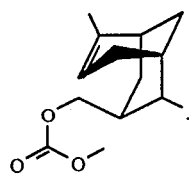

FIG. 26 is the NMR spectrum and FIG. 27 is the infrared spectrum for the compound having the structure:

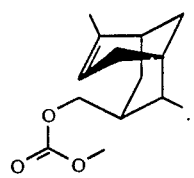

EXAMPLE X

Preparation of 2-(2,6-Dimethylbicyclo[3.3.1]non-6-en-2-yl)-1,3-Dioxolane

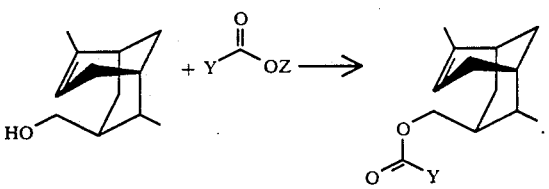

Into a 5 liter reaction vessel equipped with stirrer, thermometer and reflux condenser are placed 360 grams (2 moles) of the compound having the structure:

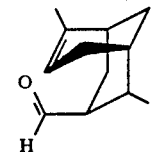

prepared according to Example I; 540 grams of ethylene glycol (1.5 moles); 4 grams of para-toluene sulfonic acid and 800 ml toluene. The reaction mass is stirred and heated to 100° C. and maintained at 100° C. with evolution of water for a period of six hours. At the end of the six hour period 56 ml water is evolved. At the end of the six hour period, the reaction mass is cooled and washed consecuitively as follows:

(i) 500 ml 5% aqueous sodium hydroxide;

(ii) 500 ml saturated sodium chloride solution (aqueous); and (iii) 500 ml water.

The reaction mass is then dried over anhydrous magnesium sulfate and filtered.

The resulting product is then fractionallly distilled yielding the following fractions:

| Fraction No. | Vapor Temp. (°C.) | Liquid Temp. (°C.) | Vacuum mm/Hg. Pressure |
|---|---|---|---|
| 1 | /40 | /11 | 3.00 |
| 2 | 128 | 140 | 2.33 |
| 3 | 131 | 143 | 2.29 |
| 4 | 126 | 142 | 2.27 |
| 5 | 110 | 200 | 2.11. |

Fractions 2–4 are bulked.

The resulting product is confirmed by NMR, IR and mass spectral analysis to have the structure:

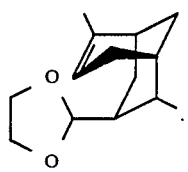

FIG. 29 is the NMR spectrum and FIG. 30 is the IR spectrum for the compound having the structure:

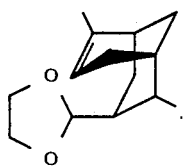

EXAMPLE XI

Pine Fragrance

The following pine fragrance formulations are prepared:

| | EXAMPLES | | | |
|---|---|---|---|---|
| | XI(A) | XI(B) | XI(C) | XI(D) |
| Isobornyl acetate | 100 | 100 | 100 | 100 |
| Camphor | 10 | 10 | 10 | 10 |
| Alpha-terpineol | 25 | 25 | 25 | 25 |
| Fir balsam absolute (50% in diethyl phthalate) | 20 | 20 | 20 | 20 |
| Coumarin | 4 | 4 | 4 | 4 |
| Linalool | 30 | 30 | 30 | 30 |
| Fenchyl alcohol | 10 | 10 | 10 | 10 |
| Anethol | 12 | 12 | 12 | 12 |
| Lemon terpenes washed | 50 | 50 | 50 | 50 |
| Borneol | 5 | 5 | 5 | 5 |
| Galbanum oil | 5 | 5 | 5 | 5 |
| Turpentine Russian | 150 | 150 | 150 | 150 |
| Eucalyptol | 50 | 50 | 50 | 50 |
| 2,2,6-Trimethyl-1-cyclo-hexene-1-carboxaldehyde | 12 | 12 | 12 | 12 |
| Maltol (1% in diethyl phthalate) | 5 | 5 | 5 | 5 |
| The compound having the structure: | 28 | 0 | 0 | 0 |

-continued

| | EXAMPLES | | | |
|---|---|---|---|---|
| | XI(A) | XI(B) | XI(C) | XI(D) |
| HO― prepared according to Example II. The compound having the structure: | 0 | 28 | 0 | 0 |
| HO― prepared according to Example III. The compound having the structure: | 0 | 0 | 28 | 0 |
| ―O― prepared according to Example V. The compound having the structure: | 0 | 0 | 0 | 28 |
| ―O― prepared according to Example VI. | | | | |

The compound having the structure:

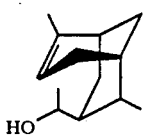

prepared according to Example II imparts to this pine formulation green, early morning forest path undertones. Accordingly, the perfume formulation of Example XI(A) can be described as "a piney aroma with green, early morning forest path undertones".

The compound having the structure:

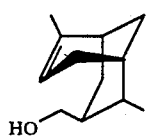

when added to this pine formulation imparts to the pine formulation sandalwood, green and camphoraceous undertones with natural pine, green, woody, sappy and camphoraceous topnotes. Accordingly, the perfume formulation of Example XI(B) can be described as "a pine aroma with sandalwood, green and camphoraceous undertones and natural pine, green, woody, sappy and camphoraceous topnotes".

The compound having the structure:

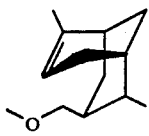

prepared according to Example V imparts to this piney fragrance formulation woody undertones with woody, pine needle topnotes. Accordingly, the perfume composition of Example XI(C) can be described as "a piney aroma with woody undertones and woody and pine needle topnotes".

The compound having the structure:

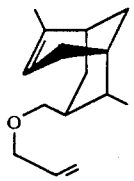

prepared according to Example VI imparts to this piney fragrance, geranium, rhodinol, peppery, woody and "cooling" undertones with rhodinol and peppery topnotes. Accordingly, the fragrance of Example XI(D) can be described as "a piney fragrance with geranium, rhodinol, peppery, woody and "cooling" undertones and rhodinol and peppery topnotes".

EXAMPLE XII

Pine Fragrance

The following pine fragrance formulations are prepared:

| | EXAMPLES | | |
|---|---|---|---|
| | XIIA) | XII(B) | XII(C) |
| Isobornyl acetate | 100 | 100 | 100 |
| Camphor | 10 | 10 | 10 |
| Alpha-terpineol | 25 | 25 | 25 |
| Fir balsam absolute (50% in diethyl phthalate) | 20 | 20 | 20 |
| Coumarin | 4 | 4 | 4 |
| Linalool | 30 | 30 | 30 |
| Fenchyl alcohol | 10 | 10 | 10 |
| Anethol | 12 | 12 | 12 |
| Lemon terpenes washed | 50 | 50 | 50 |
| Borneol | 5 | 5 | 5 |
| Galbanum oil | 5 | 5 | 5 |
| Turpentine Russian | 150 | 150 | 150 |
| Eucalyptol | 50 | 50 | 50 |
| 2,2,6-Trimethyl-cyclo-hexene-1-carboxaldehyde | 12 | 12 | 12 |
| Maltol (1% in diethyl phthalate) | 5 | 5 | 5 |
| The compound having the structure:<br>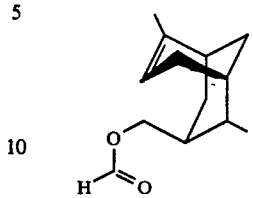<br>prepared according to Example VII. | 28 | 0 | 0 |
| The compound having the structure:<br>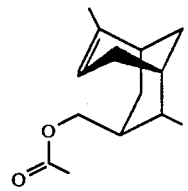<br>prepared according to Example VIII. | 0 | 28 | 0 |
| The compound having the structure:<br>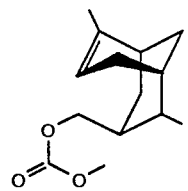<br>prepared according to Example IX. | 0 | 0 | 28 |

The compound having the structure:

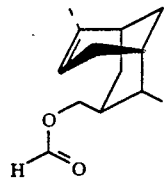

prepared according to Example VII imparts to this piney fragrance formulation orris, orivone and green undertones with camphoraceous, green and orivone topnotes. Accordingly, the fragrance of Example XII(A) can be described as "a piney fragrance having orris, orivone and green undertones and camphoraceous, green and orivone topnotes".

The compound having the structure:

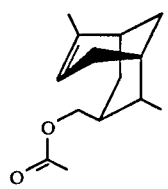

imparts to this piney fragrance formulation woody, grapefruit-like and sweet undertones. Accordingly, the fragrance formulation of Example XII(B) can be described as "a piney aroma having woody, grapefruit-like and sweet undertones".

The compound having the structure:

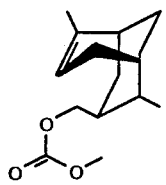

imparts to this piney fragrance formulation floral undertones. Accordingly, the fragrance formulation of Example XII(C) can be described as "a piney fragrance with floral undertones".

EXAMPLE XIII

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: 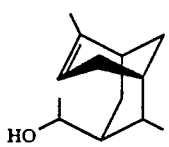 prepared according to Example II. | A green and early morning forest path aroma. |
| The compound having the structure: 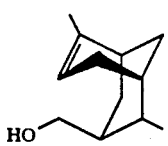 prepared according to Example III. | A sandalwood, green, piney and camphoraceous aroma with natural piney, green, woody, sappy and camphoraceous topnotes. |
| The compound having the structure: 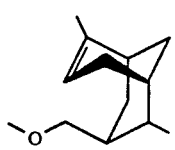 prepared according to Example V. | A woody and piney aroma with woody and pine needle topnotes. |
| The compound having the structure: | A geranium, rhodinol, peppery and woody aroma with rhodinol and peppery topnotes and "cooling" undertones. |
| The compound having the structure: prepared according to Example VI. The compound having the structure: prepared according to Example VII. | An orris, orivone and green aroma with piney, camphoraceous, green and orivone topnotes. |
| The compound having the structure: prepared according to Example VIII. | A woody, grapefruit-like and sweet aroma. |
| The compound having the structure: prepared according to Example IX. | A floral aroma. |
| The perfume composition of Example XI(A). | A piney aroma with green, early morning forest path undertones. |
| The perfume composition of Example XI(B). | A pine aroma with sandalwood, green and camphoraceous undertones and natural pine, green, woody, sappy and camphoraceous topnotes. |
| The perfume composition of Example XI(C). | A piney aroma with woody undertones and woody and pine needle topnotes. |
| The perfume composition of Example XI(D). | A piney fragrance with geranium, rhodinol, peppery, woody and "cooling" undertones and rhodinol and peppery topnotes. |
| The perfume composition of Example XII(A). | A piney fragrance having orris, orivone and green undertones and camphoraceous, green and orivone topnotes. |
| The perfume composition of Example XII(B). | A piney aroma having woody, grapefruit-like and sweet undertones. |

TABLE II-continued

| Substance | Aroma Description |
|---|---|
| The perfume composition of Example XII(C). | A piney fragrance with floral undertones. |

EXAMPLE XIV

Perfumed Liquid Detergent

Concentrated liquid detergents with aromas as set forth in Table II of Example XIII (which detergents are prepared from Lysine salt of n-dodecyl benzene sulfonic acid as more specifically described in U.S. Pat. No. 3,948,818 issued on Apr. 6, 1976, the specification for which is incorporated by reference herein) are prepared containing each of the substances set forth in Table II of Example XIII, supra. They are prepared by adding and homogeneously mixing the appropriate quantity of perfumery substance as set forth in Table II of Example XIII in the liquid detergent. The detergents all possess aromas as set forth in Table II of Example XIII, the intensity increasing with greater concentrations of perfumery substance of Table II of Example XIII, supra.

EXAMPLE XV

Preparation of A Cologne and Handkerchief Perfume

The perfume substances of Table II of Example XIII, supra, are incorporated into colognes at concentrations of 1.5%, 2.0%, 2.5%, 3.0% and 4.0% in 80%, 85% and 90% aqueous ethanol; and into a handkerchief perfume composition at concentrations of 10%, 15%, 20%, 25% and 30% (in 85%, 90% and 95% aqueous ethanol). Distinct and definitive aromas as set forth in Table II of Example XIII are imparted to the cologne and to the handkerchief perfume compositions.

EXAMPLE XVI

Preparation of A Detergent Composition

A total of 100 grams of a detergent powder (a non-ionic detergent powder containing a proteolytic enzyme prepared according to Example I of Canadian Letters Patent No. 985,190 issued on Mar. 9, 1976, the disclosure of which is incorporated by reference herein) is mixed with 0.15 grams of each of the substances until homogeneous compositions are obtained. These compositions have excellent aromas as set forth in Table II of Example XIII.

EXAMPLE XVII

Preparation of Soap

Each of the perfumery substances of Table II of Example XIII are incorporated into soap (LVU-1) at 0.1% by weight of each substance. After two weeks in the oven at 90° F., each of the soaps showed no visual effect from the heat. Each of the soaps manifested an excellent aroma as set forth in Table II of Example XIII, supra.

EXAMPLE XVIII

Preparation of Soap Composition

One hundred grams of soap chips (IVORY ®, registered trademark of the Procter & Gamble Co. of Cincinnati, Ohio) are mixed individually with one gram each of the perfumery substances of Table II of Example XIII, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table II of Example XIII, supra.

EXAMPLE XIX

Preparation of A Solid Detergent Composition

A detergent is prepared from the following ingredients according to Example I of Canadian Letters Patent No. 1,007,948, the specification for which is incorporated by reference herein.

| Ingredients | Parts by Weight |
|---|---|
| "Neodol 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of grams of this detergent is admixed separately with 0.15 grams of each of the perfume substances of Table II of Example XIII, supra. The detergent samples each have excellent aromas as set forth in Table II of Example XIII, supra.

EXAMPLE XX

Utilizing the procedure of Example I at column 15 of U.S. Pat. No. 3,632,396 (the specification for which is incorporated by reference herein), a non-woven cloth substrate useful as a dryer-added fabric softening article of manufacture is prepared, wherein the substrate, the substrate coating and the outer coating and the perfuming material are as follows:

1. a water "dissolvable" paper ("Dissolvo Paper");
2. ADOGEN ® 448 (m.p. about 140° F.) as the substrate coating; and
3. an outer coating having the following formulation (m.p. about 150° F.);
   57%—$C_{20-22}$ HAPS;
   22%—isopropyl alcohol;
   20%—antistatic agent;
   1%—of one of the perfume substances of Table II of Example XIII, supra.

A fabric softening composition prepared as set forth above having the above aroma characteristics as set forth in Table II of Example XIII, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table II of Example XIII is imparted in a pleasant manner to the headspace in the dryer on operation thereof, using said dryer-added fabric softening non-woven fabric.

EXAMPLE XXI

A fabric washing deodorant detergent powder product is prepared by admixing the following ingredients:

| Ingredients | Parts by Weight |
|---|---|
| Linear alkylbenzene sulfonate | 9.0 |

-continued

| Ingredients | Parts by Weight |
| --- | --- |
| $C_{13}-C_{15}$ straight chain alcohols (30:30:40 mixture of $C_{13}$, $C_{14}$ and $C_{15}$ straight chain alcohol) | 4.0 |
| Sodium tripolyphosphate | 16.0 |
| ZEOLIGHT ® | 8.0 |
| Sodium silicate | 4.0 |
| Magnesium silicate | 0.8 |
| Ethylene diamine | 0.6 |
| N,N,N',N'[tetra(methylene phosphonic acid)] sodium carboxy methyl cellulose | 0.9 |
| Anti-foam | 1.5 |
| Sodium Perborate tetrahydrate | 14.0 |
| N,N,N',N'-Tetraacetyl Glycoluril | 4.2 |
| The compound having the structure: 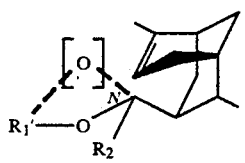 prepared according to Example III. | 5.05 |
| Water | 45.0 |
| Sodium sulfate | 5.0 |

The resulting fabric washing deodorant detergent powder on use gives rise to a very pleasant sandalwood, green, piney and camphoraceous aroma with natural piney, green, woody, sappy and camphoraceous topnotes without any aesthetically displeasing aromas subsequent to washing of fabrics in the standard washing machine cycle.

Deodorant detergent products have also been prepared according to Examples I-IX of U.S. Pat. No. 4,304,679 incorporated by reference herein.

Thus, exemplified herein by reference are the following:

a deodorant detergent product comprising:

(i) from 0.5 to 99.99% by weight of a non-soap detergent active compound; and (ii) from 0.01 to 10% by weight of a deodorant composition comprising from 45 to 100% by weight of at least one of the 2,6-dimethylbicyclo[3.3.1]non-6-ene-3-methanol and substituted derivatives thereof of our invention defined according to the structure:

wherein the dashed lines represent a carbon-oxygen covalent bond or no bond and N is 0 or 1; and wherein $R_1$ is hydrogen, $C_1-C_2$ lower alkyl, lower alkenyl, lower alkylenyl, $C_1-C_2$ acyl, or alkoxycarbonyl; and $R_2$ is lower alkyl or hydrogen; with the provisos that when N is 1, the dashed lines are carbon-oxygen covalent bonds, $R_2$ is hydrogen and $R_1$ is only lower alkylenyl; and when N is 0, the dashed lines are no covalent bonds and $R_1$ is not lower alkylenyl.

These compounds include compounds having the genus:

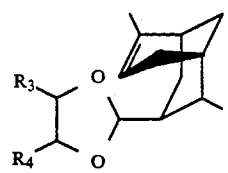

wherein $R_3$ and $R_4$ are the same or different hydrogen or lower alkyl prepared according to the reaction:

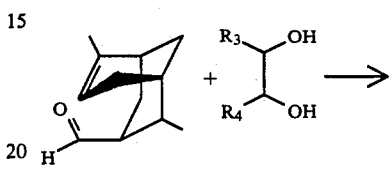

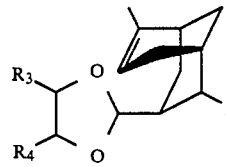

More specifically, $R_3$ and $R_4$ each represent the same or different $C_1-C_4$ lower alkyl or hydrogen, for example, when $R_3$ is methyl and $R_4$ is methyl.

Furthermore, the examples of U.S. Pat. No. 4,663,068 are also incorporated herein by reference, to wit:

(i) from 5 to 40% by weight of a non-soap detergent active compound comprising an anionic detergent active compound;

(ii) from 1 to 90% of a non-soap detergency builder;

(iii) from 1 to 30% by weight a peroxy bleach compound together with an activator therefor; and (iv) from 0.1 up to 10% by weight of a bleach stable perfume which comprises 50-100% by weight of at least one bleach stable 2,6-dimethylbicyclo[3.3.1]-non-6-ene-3-methanol and substituted derivatives thereof of our invention defined according to the structure:

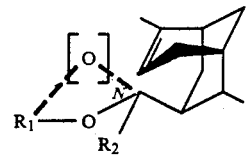

wherein the dashed lines, N, $R_1$ and $R_2$ are defined, supra, having a Lipoxidase-inhibiting capacity of at least 50% or a Raoult variance ratio of at least 1.1 as defined according to U.S. Pat. No. 4,663,068 incorporated by reference herein, with the 2,6-dimethylbicyclo[3.3.1]non-6-ene-3-methanol and substituted derivatives thereof of our invention being stable in the presence of sodium perborate tetrahydrate or any other alkali metal perborate tetrahydrate and N,N,N',N'-tetraacetyl ethylenediamine (TEAD) according to the bleach stability test as defined in said U.S. Pat. No. 4,663,068 incorporated by reference herein, the bleach stable deodorant 2,6-dimethylbicyclo[3.3.1]non-6-ene-3-methanol and substituted derivatives thereof of our invention having a Malodor Reduction Value of from 0.25 up to 3.0 as measured by the Malodor Reduction Value test defined in said U.S. Pat. No. 4,663,068 incorporated by reference herein.

The peroxy bleach activator may be exemplified by the following peroxy bleach activators:
N,N,N',N'-tetraacetyl ethylenediamine;
N,N,N',N'-tetraacetyl glycoluril;
Glucose pentaacetate;
Sodium acetoxybenzene sulphonate;
Sodium nonanolyoxybenzene sulphonate;
Sodium octanoyloxybenzene sulphonate; and mixtures thereof.

The non-soap anionic detergent active compound may be selected from the group consisting of sodium and potassium alkyl sulphates, sodium, potassium and ammonium alkyl benzene sulphonates, sodium alkyl glyceryl ether sulphates, sodium coconut oil fatty acids, monoglyceride sulphates and sulphonates, sodium and potassium salts of sulphuric acid esters of higher ($C_9$–$C_{18}$) fatty alcohol-alkylene oxide, the reaction products of fatty acids esterified with isethionic acid and neuralized with sodium hydroxide, sodium and potassium salts of fatty acid amines of methyl taurine, alkane monosulphonates, olefin sulphonates and mixtures thereof.

The nonionic detergent active compound may be selected from the group consisting of reaction products of alkylene oxides with alkyl ($C_6$–$C_{22}$) phenols, the condensation products of aliphatic ($C_8$–$C_{18}$) primary or secondary linear or branched alcohols with ethylene oxide, products made by condensation of ethylene oxide with the reaction products of propylene oxide and ethylene aliamine, long-chain tertiary amine oxides, long-chain phosphine oxides and dialkyl sulphoxides and mixtures thereof.

What is claimed is:

1. At least one 2,6-dimethylbicyclo[3.3.1]non-6-ene-3-methanol and substituted derivative thereof defined according to the structure:

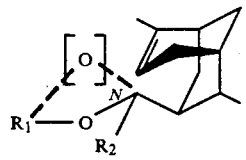

wherein each of the dashed lines represents a carbon-oxygen covalent bond or no bond; N is 0 or 1; $R_1$ represents hydrogen, $C_1$–$C_2$ lower alkyl, lower alkenyl, lower alkylenyl, $C_1$–$C_2$ acyl, alkoxycarbonyl, magnesium halo or lithium; and $R_2$ represents lower alkyl or hydrogen; with the proviso that when N equals 1, each of the dashed lines are carbon-oxygen covalent bonds, $R_2$ is hydrogen and $R_1$ is only lower alkylenyl; and when N is 0, each of the dashed lines are no covalent bonds and $R_1$ is not lower alkylenyl.

2. At least one 2,6-dimethylbicyclo[3.3.1]non-6-ene-3methanol and substituted derivative thereof defined according to the structure:

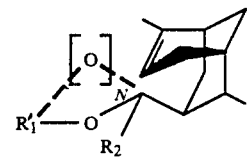

wherein each of the dashed lines represents a carbon-oxygen covalent bond or no bond; N is 0 or 1; $R_1$ represents hydrogen, $C_1$–$C_2$ lower alkyl, lower alkenyl, lower alkylenyl, $C_1$–$C_2$ acyl, or alkoxycarbonyl; and $R_2$ is lower alkyl or hydrogen, with the provisos that when N is 1 each of the dashed lines are carbon-oxygen covalent bonds, $R_2$ is hydrogen and $R_1$ is only lower alkylenyl; and when N is 0, each of the dashed lines are no covalent bonds and $R_1$ is not lower alkylenyl.

3. A 2,6-dimethylbicyclo[3.3.1]non-6-ene-3-methanol derivative defined according to claim 1 having the structure:

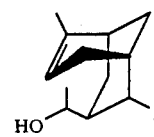

4. A 2,6-dimethylbicyclo[3.3.1]non-6-ene-3-methanol derivative defined according to claim 1 having the structure:

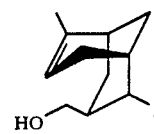

5. A 2,6-dimethylbicyclo[3.3.1]non-6-ene-3-methanol derivative defined according to claim 1 having the structure:

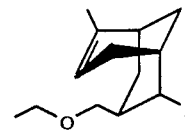

6. A 2,6-dimethylbicyclo[3.3.1]non-6-ene-3-methanol derivative defined according to claim 1 having the structure:

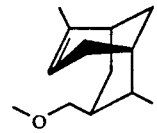

7. A 2,6-dimethylbicyclo[3.3.1]non-6-ene-3-methanol derivative defined according to claim 1 having the structure:

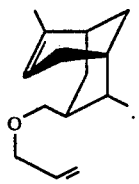

8. A 2,6-dimethylbicyclo[3.3.1]non-6-ene-3-methanol derivative defined according to claim 1 having the structure:

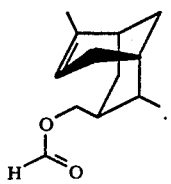

9. A 2,6-dimethylbicyclo[3.3.1]non-6-ene-3-methanol derivative defined according to claim 1 having the structure:

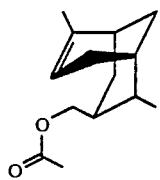

10. A 2,6-dimethylbicyclo[3.3.1]non-6-ene-3-methanol derivative defined according to claim 1 having the structure:

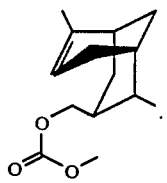

11. A 2,6-dimethylbicyclo[3.3.1]non-6-ene-3-methanol derivative defined according to claim 1 having the structure:

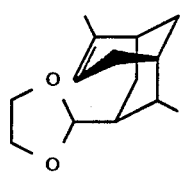

12. The 2,6-dimethylbicyclo[3.3.1]non-6-ene-3--methanol derivative of claim 3 defined according to the structure:

wherein M is selected from the group consisting of Li and MgX and wherein X is selected from the group consisting of chloro and bromo.

13. The 2,6-dimethylbicyclo[3.3.1]non-6-ene-3-methanol derivative of claim 12 wherein M is Li.

14. The 2,6-dimethylbicyclo[3.3.1]non-6-ene-3-methanol derivative of claim 12 having the structure:

wherein X is chloro or bromo.

15. A consumable material selected from the group consisting of perfume compositions, perfumed articles, colognes, deodorizing articles, deodorizing compositions and malodor maskants comprising a perfume base, a perfumed article base, a cologne base, a deodorizing article base, a deodorizing composition base or a malodor maskant base and intimately admixed therewith an aroma augmenting, modifying or enhancing quantity or concentration of a 2,6-dimethylbicyclo[3.3.1]non-6-ene-3-methanol derivative defined according to claim 2.

16. A cologne comprising water, ethanol and at least one 2,6-dimethylbicyclo[3.3.1]non-6-ene-3-methanol derivative defined according to claim 2.

17. A perfume composition consisting essentially of a perfume base and intimately admixed therewith an aroma augmenting, enhancing or modifying quantity or concentration of at least one 2,6-dimethylbicyclo[3.3.1]-non-6-ene-3-methanol derivative defined according to claim 2.

18. A perfumed detergent consisting essentially of a solid or liquid anionic, cationic, nonionic or zwitterionic detergent base and intimately admixed therewith an aroma augmenting, enhancing or modifying quantity or concentration of at least one 2,6-dimethylbicyclo[3.3.1]non-6-ene-3-methanol derivative defined according to claim 2.

19. A perfumed polymer consisting essentially of a microporous polymer and present in the interstices thereof at least one aroma augmenting, enhancing or modifying quantity of at least one 2,6-dimethylbicyclo[3.3.1]non-6-ene-3-methanol derivative defined according to claim 2.

20. A deodorant detergent product comprising:
(i) from 0.5 to 99.99% by weight of a non-soap detergent active compound; and
(ii) from 0.01 to 10% by weight of a deodorant composition comprising from 45 to 100% by weight of at least one 2,6-dimethylbicyclo[3.3.1]non-6-ene-3-methanol derivative defined according to claim 2.

21. A deodorant detergent powder product suitable for use in the washing of fabrics which comprises:
  (i) from 5 to 40% by weight of a non-soap detergent active compound comprising an anionic detergent active compound;
  (ii) from 1 to 90% by weight of a non-soap detergency builder;
  (iii) from 1 to 30% by weight of a peroxy bleach compound together with an activator therefor; and
  (iv) from 0.1 up to 5% of a bleach stable deodorant perfume which comprises 50 to 100% of at least one 2,6-dimethylbicyclo[3.3.1]non-6-ene-3-methanol derivative defined according to claim 2.

22. A process for augmenting, enhancing or modifying a consumable material selected from the group consisting of perfume compositions, perfumed articles, colognes, deodorizing articles, deodorizing compositions and malodor maskants comprising the step of adding to said consumable material an aroma augmenting, modifying or enhancing quantity of at least one 2,6-dimethylbicyclo[3.3.1]non-6-ene-3-methanol derivative defined according to claim 2.

23. The process of claim 22 wherein the consumable material is a perfume composition, perfumed article or cologne.

* * * * *